US006753423B1

(12) United States Patent
Cook et al.

(10) Patent No.: US 6,753,423 B1
(45) Date of Patent: Jun. 22, 2004

(54) COMPOSITIONS AND METHODS FOR ENHANCED BIOSTABILITY AND ALTERED BIODISTRIBUTION OF OLIGONUCLEOTIDES IN MAMMALS

(75) Inventors: Phillip Dan Cook, Escondido, CA (US); Muthiah Manoharan, Carlsbad, CA (US); Clarence Frank Bennett, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/546,596

(22) Filed: Apr. 10, 2000

Related U.S. Application Data

(63) Continuation of application No. 08/928,823, filed on Sep. 12, 1997, and a continuation-in-part of application No. 08/731,299, filed on Oct. 4, 1996, now Pat. No. 6,078,785, which is a continuation-in-part of application No. 08/464,953, filed on Jun. 5, 1995, and a continuation-in-part of application No. 08/344,155, filed on Nov. 23, 1994, now Pat. No. 5,883,082, which is a continuation-in-part of application No. 08/117,363, filed on Sep. 3, 1993, which is a continuation-in-part of application No. 08/063,167, filed on May 17, 1993, now Pat. No. 5,514,788, which is a continuation-in-part of application No. 08/007,997, filed on Jan. 21, 1993, now Pat. No. 5,591,623, which is a continuation-in-part of application No. PCT/US92/09196, filed on Oct. 23, 1992, which is a continuation-in-part of application No. 07/939,855, filed on Sep. 2, 1992, now abandoned, which is a continuation-in-part of application No. 07/782,374, filed on Oct. 24, 1991, now abandoned, which is a continuation-in-part of application No. 07/567,286, filed on Aug. 14, 1990, now abandoned, and a continuation-in-part of application No. 07/566,977, filed on Aug. 13, 1990, now abandoned, which is a continuation-in-part of application No. 07/463,358, filed on Jan. 11, 1990, now abandoned.

(51) Int. Cl.[7] .................. C07H 21/04; A61K 48/00; C12Q 1/68

(52) U.S. Cl. .................. 536/24.5; 536/23.1; 536/24.3; 435/6; 514/44

(58) Field of Search .................. 435/6; 536/23.3, 536/24.3, 24.5

(56) References Cited

U.S. PATENT DOCUMENTS

| | | | |
|---|---|---|---|
| 3,687,808 A | 8/1972 | Merigan, Jr. et al. | 195/28 |
| 4,605,735 A | 8/1986 | Miyoshi et al. | 536/27 |
| 4,689,320 A | 8/1987 | Kaji | 514/44 |
| 4,743,535 A | 5/1988 | Carrico | 435/6 |
| 4,806,463 A | 2/1989 | Goodchild et al. | 435/5 |
| 4,835,263 A | 5/1989 | Nguyen et al. | 536/27 |
| 4,904,582 A | 2/1990 | Tullis | 3435/6 |
| 4,910,300 A | 3/1990 | Urdea et al. | 536/287 |
| 4,958,013 A | 9/1990 | Letsinger | 536/27 |
| 5,015,733 A | 5/1991 | Smith et al. | 536/23 |
| 5,034,506 A | 7/1991 | Summerton et al. | 528/391 |
| 5,087,617 A | 2/1992 | Smith | 514/44 |
| 5,098,890 A | 3/1992 | Gerwirtz et al. | 514/44 |
| 5,108,921 A | 4/1992 | Low et al. | 435/240.1 |
| 5,135,917 A | 8/1992 | Burch | 514/44 |
| 5,138,045 A | 8/1992 | Cook et al. | 536/27 |
| 5,166,195 A | 11/1992 | Ecker | 514/44 |
| 5,194,428 A | 3/1993 | Agrawal et al. | 514/44 |
| 5,212,295 A | 5/1993 | Cook | 536/26.7 |
| 5,218,105 A | 6/1993 | Cook et al. | 536/25.31 |
| 5,223,618 A | 6/1993 | Cook et al. | 544/276 |
| 5,242,906 A | 9/1993 | Pagano et al. | 514/44 |
| 5,264,423 A | 11/1993 | Cohen et al. | 514/44 |
| 5,272,263 A | 12/1993 | Hession | 536/23.5 |
| 5,276,019 A | 1/1994 | Cohen et al. | 514/44 |
| 5,284,931 A | 2/1994 | Springer et al. | 424/85.8 |
| 5,286,717 A | 2/1994 | Cohen et al. | 514/44 |
| 5,324,654 A * | 6/1994 | Bredesen | 435/240.2 |
| 5,378,825 A | 1/1995 | Cook et al. | 536/25.34 |
| 5,386,023 A | 1/1995 | Sanghvi et al. | 536/25.3 |
| 5,457,191 A | 10/1995 | Cook et al. | 536/27.13 |
| 5,459,255 A | 10/1995 | Cook et al. | 536/27.13 |
| 5,466,786 A | 11/1995 | Buhr et al. | 536/26.26 |
| 5,470,967 A | 11/1995 | Huie et al. | 536/24.3 |
| 5,506,351 A | 4/1996 | McGee | 536/55.3 |
| 5,510,239 A | 4/1996 | Baracchini, Jr. et al. | 435/6 |

(List continued on next page.)

FOREIGN PATENT DOCUMENTS

| | | |
|---|---|---|
| EP | 0251283 | 1/1988 |
| WO | WO 86/02929 | 5/1986 |
| WO | WO 89/02931 | 4/1989 |
| WO | WO 89/12060 | 12/1989 |
| WO | WO 91/00243 | 6/1990 |
| WO | WO 90/10448 | 9/1990 |
| WO | WO 90/13300 | 11/1990 |
| WO | WO 91/15500 | 10/1991 |
| WO | WO 91/14696 | 11/1991 |
| WO | WO 92/05186 | 4/1993 |
| WO | WO 95/06659 | 3/1995 |
| WO | WO 96/02556 | 2/1996 |

OTHER PUBLICATIONS

Blum et al, "Inhibition of hepatitis B virus by antisense oligodeoxynucleotides", Lancet 337:1230 (1991).*

Letsinger et al, "Cholesteryl conjugated oligonucleotides: synthesis, properties and activity as inhibitors of replication of human immunodeficiency virus in cell culture", Proc. Natl. Acad. Sci. (1989) 86:6553–6556.*

Branch, A.D., "A hitchhiker's guide to antisense and nonantisense biochemical pathways," *Hepatology,* 1996, 24(6), 1517–1529 (Abstract 1 page).

(List continued on next page.)

*Primary Examiner*—Jeffrey Fredman
(74) *Attorney, Agent, or Firm*—Matthew V. Grumbling; Michael P. Straher; Cozen O'Connor

(57) ABSTRACT

The invention is directed to oligonucleotides and oligonucleosides functionalized to include lipophilic moieties and having improved biostability and altered biodistribution in mammals. In one embodiment, such lipophilic oligonucleotide conjugates are used in a method of targeting antisense oligonucleotides to hepatic tissues and thereby preferentially modulating gene expression in the liver and associated tissues of a mammal.

7 Claims, 15 Drawing Sheets

U.S. PATENT DOCUMENTS

| | | | |
|---|---|---|---|
| 5,514,788 A | 5/1996 | Bennett et al. | 536/23.1 |
| 5,521,302 A | 5/1996 | Cook | 536/25.31 |
| 5,539,082 A | 7/1996 | Nielsen et al. | 530/300 |
| 5,541,307 A | 7/1996 | Cook et al. | 536/23.1 |
| 5,554,746 A | 9/1996 | Ravikumar et al. | 540/200 |
| 5,571,902 A | 11/1996 | Ravikumar et al. | 536/22.1 |
| 5,578,718 A | 11/1996 | Cook et al. | 536/27.21 |
| 5,580,969 A | 12/1996 | Hoke et al. | 536/24.5 |
| 5,585,479 A | 12/1996 | Hoke et al. | 536/24.5 |
| 5,587,361 A | 12/1996 | Cook et al. | 514/44 |
| 5,587,469 A | 12/1996 | Cook et al. | 536/23.1 |
| 5,587,470 A | 12/1996 | Cook et al. | 536/23.1 |
| 5,591,623 A | 1/1997 | Bennett et al. | 435/240.2 |
| 5,596,090 A | 1/1997 | Hoke et al. | 536/24.5 |
| 5,599,797 A | 2/1997 | Cook et al. | 514/44 |
| 5,602,240 A | 2/1997 | De Mesmaeker et al. | 536/22.1 |
| 5,608,046 A | 3/1997 | Cook et al. | 536/23.1 |
| 5,610,289 A | 3/1997 | Cook et al. | 536/25.34 |
| 5,618,704 A | 4/1997 | Sanghvi et al. | 435/91.5 |
| 5,623,070 A | 4/1997 | Cook et al. | 536/27.6 |
| 5,670,633 A | 9/1997 | Cook et al. | |
| 5,677,437 A | 10/1997 | Teng et al. | 536/23.1 |

OTHER PUBLICATIONS

Asseline, U. et al., "Solid–Phase Preparation of 5'–3'–Heterobifunctional Oligodeoxyribonucleotides Using Modified Solid Supports", Tetrahedron 1992, 48, 1233–1254.

Asseline, U. et al., "Nucleic acid–binding molecules with high affinity and base sequence specificity: Intercalating agents covalently linked to oligodeoxynucleotides", *Proc. Natl. Acad. Sci. USA* 1984, 81, 3297–3301.

Atherton,E. et al., *The Peptides,* Gross and Meienhofer, Eds, Academic Press; New York, vol. 9:1–38, 1983.

Baker, B.F., "Decapitation of a 5'–Capped Oligoribonucleotide by o–Phenanthroline: CU(II)", *J. Am. Chem. Soc.* 1993, 115, 3378–3379.

Beaucage, S. et al., "Advances in the Synthesis of Oligonucleotides by the Phosphoramidite Approach", *Tetrahedron* 1992, 48, 2223–2311.

Bennett, C.F. et al., "Cationic Lipids Enhance Cellular Uptake and Activity of Phosphorothioate Antisense Oligonucleotides", *Molecular Pharmacology* 1991, 41, 1023–1033.

Betebenner, D.A., et al., "Hepatobiliary Delivery of Polyaminopolycarboxylate Chelates: Synthesis and Characterization of a Cholic Acid Conjugate of EDTA and Biodistribution and Imaging Studies with Its Indium–111 Chelate", *Bioconjugate Chem.* 1991, 2, 117–123.

Bischoff, R. et al., "Introduction of 5'–Terminal Functional Groups into Synthetic Oligonucleotides for Selective Immobilization", *Analy. Biochem.* 1987, 164, 336–344.

Blackburn, G. et al., "Studies in Phosphorylation. Part XXIX. The Synthesis of Dialkyl Phosphates from Monoalkyl Phosphonates: Direct Oxidative Esterification", *J. Chem. Soc.* 1966, 239–245.

Chiang, M.–Y. et al., "Antisense Oligonucleotides Inhibit Intercellular Adhesion Molecule 1 Expression by Two Distinct Mechanisms", *J. of Biol. Chem.* 1991, 266, 18162–18171.

Chollet, A., "Selective Attachment of Oligonucleotides to Interleukin–1 beta and Targeted Delivery to Cells", *Nucleosides & Nucleotides* 1990, 9, 957–966.

Cohen, J. in *Oligonucleotides: Antisense Inhibitors of Gene Expression,* CRC Press, Inc., Boca Raton, FL, 1989.

Corey, D. et al., "Sequence–Selective Hydrolysis of Duplex DNA by an Oligonucleotide–Directed Nuclease", *J. Am. Chem. Soc.* 1989, 111, 8523–8525.

Corey, D. et al., "Generation of a Hybrid Sequence–Specific Single–Stranded Deoxyribonuclease", *Science* 1987, 238, 1401–1403.

Damha, M. et al., "An Improved Procedure for Derivatization of Controlled–Pore Glass Beads for Solid–Phase Oligonucleotide Synthesis", *Nuc. Acids Res.* 1990, 18, 3813–3821.

Delgado, C. et al., "The Uses and Properties of PEG–Linked Proteins", *Critical Reviews in Therapeutic Drug Carrier Systems* 1992, 9, 249–304.

Dingwall, C., et al., "Protein Import Into the Cell Nucleus", *Ann. Rev. Cell Biol.* 1986, 2, 367–90.

DiZio, J. et al., "Progestin–Thenium Complexes: Metal–Labeled Steroids with High Receptor Binding Affinity, Potential Receptor–Directed Agents for Diagnostic of Therapy", *Bioconjugate Chem.* 1991, 2, 353–366.

Dreyer, G. et al., "Sequence–Specific Cleavage of Single–Stranded DNA: Oligodeoxynucleotide–EDTA.Fe(II)", *PNAS USA* 1985, 82, 968–972.

Egholm, M. et al., "Peptide Nucleic Acids (PNA). Oligonucleotide Analogues with an Achiral Peptide Backbone",*J. Am. Chem. Soc.* 1992, 114, 1895–1897.

Ferentz, A.E. and Verdine, G.L., "Disulfide Cross–Linked Oligonucleotides", *J. Am. Chem. Soc.* 1991, 113, 4000–4003.

Fidanza, J. et al., "Site–Specific Labeling of DNA Sequences Containing Phosphorothioate Diesters", *J. Am. Chem. Soc.* 1992, 114, 5509–5517.

Fidanza, J. et al., "Use of a Thiol Tether for the Site–Specific Attachment of Reporter Groups of DNA", *J. Org. Chem.* 1992, 57, 2340–2346.

Froehler, B. et al., "Synthesis of DNA via Deoxynucleoside H–Phosphonate Intermediates", *Nucleic Acids Research* 1986, 14, 5399–5407.

Gaur, R. et al., "A Simple Method for the Introduction of Thiol Group at 5'–Termini of Oligodeoxynucleotides", *Nuc. Acids Res.* 1989, 17, 4404.

Greene et al., *Protective Groups in Organic Synthesis,* 2nd edition, New York, John Wiley & Sons, pp. 178–223, 1991.

Greenfield, L. et al., "Thiol–Containing Cross–Linking Agent with Enhanced Stearic Hindrance", *Bioconjugate Chem.* 1990, 1, 400–410.

Guerra, F.I. et al., "Synthetic 7–Glucosyl Phospholipid as a Drug Transport System", *Tetrahedron Letters* 1987, 28, 3581–3584.

Haralambidis J., et al., "Preparation of Base–modified Nucleosides Suitable for Non–Radioactive Label Attachment and Their Incorporation Into Synthetic Oligodeoxyribonucleotides", *Nucleic Acids Research* 1987, 15, 4857–4876.

Haralambidis, J. et al., "The Solid Phase Synthesis of Oligonucleotides containing a 3'–Peptide Moiety", *Tetrahedron Letters* 1987, 28, 5199–5202.

Harris, C. et al., "New Strategy for the Synthesis of Oligodeoxynucleotides Bearing Adducts at Exocyclic Amino Sites of Purine Nucleosides", *J. Am. Chem. Soc.* 1991, 113, 4328–4329.

Iyer, R. et al., "3H–1, 2–Benzodithiole–3–one, 1,1,–Dioxide as an Improved Sulfurizing Reagent in the Solid–Phase Synthesis of Oligodeoxyribonucleoside Phosphorothioates", *J. Am. Chem. Soc.* 1990, 112, 1253–1254.

Jablonski, E. et al., "Preparation of Oligodeoxynucleotide-Alkaline Phosphatase Conjugates and Their Use as Hybridization Probes", *Nucleic Acid Research* 1986, 14, 6115–28.

Juby, C.D., et al., "Facile Preparation of 3'Oligonucleotide-Peptide Conjugates", *Tetrahedron Letters* 1991, 32, 879–882.

Krieg, A.M., et al., "Uptake of Oligodeoxyribonucleo–tides by Lymphoid Cells Is Heterogeneous and Inducible", *Antisense Research and Development* 1991 1, 161–171.

Lemaitre, M. et al., "Specific Antiviral Activity of a Poly(L–lysine)–Conjugated Oligodeoxyribonucleotide Sequence Complementary to Vesicular Stomatitis Virus N Protein mRNA Initiation Site", *PNAS USA* 1987, 84, 648–652.

Leonetti, J.P. et al, "Biological Activity of Oligonucleotide-Poly(L–lysine) Conjugates: Mechanism of Cell Uptake", *Bioconjugate Chem.* 1990, 1, 149–153.

Letsinger, R.L., et al., "Cholesteryl–Conjugated Oligonucleotides: Synthesis, Properties, and Activity as Inhibitors of Replication of Human Immunodeficiency Virus in Cell Culture", *Proc. Natl. Acad. Sci. USA* 1989, 86, 6553–6556.

MacMillan, A. et al, "Synthesis of Functionally Tethered Oligodeoxynucleotides by the Convertible Nucleoside Approach", *J. Org. Chem.* 1990, 55, 5931–5933.

Manoharan, M. et al., "Novel Functionalization of the Sugar Moiety of Nucleic Acids For Multiple Labeling in the Minor Groove", Tetra.Ltrs. 32:7171–7174 (1991).

Meyer, R. et al., "Efficient, Specific Cross–Linking and Cleavage of DNA by Stable, Synthetic Complementary Oligodeoxynucleotides", *J. Am. Chem. Soc.* 1989, 111, 8517–8519.

Miller, P.S. et al., "A New Approach to Chemotherapy Based on Molecular Biology and Nucleic Acid Chemistry: Matagen: Masking Tape for Gene Expression", *Anti–Cancer Drug Design* 1987, 2, 117–128.

Mirabelli, C.K. et al., "In vitro and in vivo pharmacologic activities of antisense oligonucleotides", *Anti–Cancer Drug Design* 1991, 6, 647–661.

Mori, K. et al., "Synthesis and Properties of Novel 5'–Linked Oligos", *Nucleosides & Nucleotides* 1989, 8, 649–657.

Nelson, P. et al., "Bifunctional Oligonucleotide Probes Synthesized Using a Novel CPG Support Are Able to Detect Single Base Pair Mutants", *Nuc. Acids Res.* 1989, 17, 7187–7194.

Ouchi, T. et al., "Synthesis and Antitumor Activity of Poly(Ethylene Glycol)s Linked to 5–Fluorouracil Via a Urethan or Urea Bond", *Drug Design and Discovery* 1992, 9, 93–105.

Pidgeon, C. et al., Synthesis and Liposome Encapsulation of Antisense Oligonucleotide–Intercalator Conjugates, *Annals New York Academy of Sciences* pp. 593–596.

Ramirez, F. et al., "Nucleotidophospholipids: Oligonucleotide Derivatives with Membrane–Recognition Groups", *J. Am. Chem. Soc.* 1982, 104, 5483–5486.

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.* 1991, 56, 4329–4333.

Shea, R. et al., "Synthesis, Hybridization Properties and Antiviral Activity of Lipid–Oligodeoxynucleotide Conjugates", *Nuc. Acids Res.* 1990, 18, 3777–3783.

Sigman, D.S., "Chemical Nucleases", *Biochemistry* 1990, 29, 9097–9105.

Sinha, N.D. et al., "The Preparation and Application of Functionalized Synthetic Oligonucleotides: III. Use of H–Phosphonate Derivatives of Protected Amino–Hexanol and Mercapto–Propanol or –Hexanol", *Nucleic Acids Res.* 1988, 16, 2659–2669.

Sluka, J. et al., "Reagents and Methods for the Solid–Phase Synthesis of Protein–EDTA for Use in Affinity Cleaving", *J. Am. Chem. Soc.* 1990, 112, 6369–6374.

Smith–Jones, P. et al., "Antibody Labeling with Copper–67 Using the Bifunctional Marcrocycle 4–((1,4,8,11–Tetraazacyclotetradec–1–yl)methyl)Benzoic Acid", *Bioconjugate Chem.* 1991, 2, 415–421.

Solomons, T.W. et al., *Organic Chemistry*, John Wiley & Sons, New York, pp. 818–819, 1980.

Sproat, B. et al., "The Synthesis of Protected 5'–Mercapto–2', 5'–Dideoxyribonucleoside–3'–O–Phosphoramidites; Uses of 5'–Mercapto–Oligodeoxyribonucleotides", *Nucleic Acids Res.* 1987, 15, 4837–4848.

Stein, C. et al., "Antisense Oligonucleotides as Therapeutic Agents—Is the Bullet Really Magical?" *Science* 1993, 261, 1004–1012.

Telser, J. et al., "Synthesis and Characterization of DNA Oligomers and Duplexes Containing Covalently Attached Molecular Labels: Comparison of Biotin, Fluorescin, and Pyrene Labels by Thermodynamic and Optical Spectroscopic Measurements", *J. Am Chem. Soc.,* 1989, 111, 6966–6976.

Tseng, B. et al., "Antisense Oligonucleotide Technology in the Development of Cancer Therapeutics", *Cancer Gene Therapy* 1994, 1(1), 65–71.

Uhlmann, E. and A. Peyman, "Antisense Oligonucleotides: A New Therapeutic Principle", Chem. Rev. 1990, 90, 543–584.

Vasseur, J. et al., "Oligonucleosides: Synthesis of a Novel Methylhydroxylamine–Linked Nucleosides Dimer and its Incorporation into Antisense Sequences", *J. Am. Chem. Soc.* 1992, 114, 4006–4007.

Veber, D. et al., "Isonicotinyloxycarbonyl, a Novel Amino Protecting Group for Peptide Synthesis", *J. Org. Chem.* 1977, 42, 3286–3288.

Wagner, D. et al., "Preparation and Synthetic Utility of Some Organotin Derivatives of Nucleosides", *J. Org. Chem.* 1974, 39, 24–30.

Wychowski, C. et al., "The Intranuclear Location of Simian Virus 40 Polypeptides VP2 and VP3 Depends on a Specific Amino Acid Sequence", *J. Virol.* 1987, 61, 3862–3869.

Yamana, K. et al., "Synthesis of Oligonucleotide Derivatives with Pyrene Group at Sugar Fragment", *Tetrahedron Lett.* 1991, 32, 6347–6350.

Yamana, K. et al., "Synthesis and Interactive Properties of an Oligonucleotide with Anthraquinone at the Sugar Fragment", *Bioconjugate Chem.* 1990, 1, 319–324.

Yoneda, Y. et al., "Synthetic Peptides Containing a Region of SV40 Large T–Antigen Involved in Nuclear Localization Direct the Transport of Proteins Into the Nucleus", *Experimental Cell Research* 1987, 170, 439.

Zhang, Z. and McCormick, "Uptake of N–(4'–pyridoxyl)amines and Release of Amines by Renal Cells: A Model for Transporter–Enhanced Delivery of Bioactive Compounds", *PNAS USA* 1991, 88, 10407–10410.

Zuckermann, R. et al., "Site–Selective Cleavage of RNA by a Hybrid Enzyme", *J. Am. Chem. Soc.* 1988, 110, 1614–1615.

Zuckermann et al., "Efficient Methods for Attachment of Thiol Specific Probes to The 3'–Ends of Synthetic Oligodeoxyribonucleotides", *Nucleic Acids Research* 1987, 15, 5305–5320.

Zon, G., "Oligonucleotide Analogues as Potential Chemotherapy Agents", *Pharmaceutical Research* 1988, 5(9), 539–549.

Stein, C.A. and Cohen, "Oligodeoxynucleotides as Inhibitors of Gene Expression: A Review", *Cancer Research* 1988, 48, 2659–2668.

Walder, R. and Walder, "Role of RNase H in hybrid–arrested translation by antisense oligonucleotides", *PNAS USA* 1988, 85, 5011–5015.

Walder, J., "Antisense DNA and RNA: Progress and Prospects" *Genes and Development* 1988, 2, 502–504.

Marcus–Sekura, "Techniques for Using Antisense Oligodeoxyribonucleotides to Study Gene Expression", *Anal. Biochemistry* 1988, 172, 289–295.

Marcus–Sekura, C.J. et al., "Comparative inhibition of chloramphenicol acetyltransferase gene expression by antisense oligonucleotide analogues having alkyl phosphotriester, methylphosphonate and phosphorothioate linkages", *Nucleic Acid Research* 1987, 15, 5749–5763.

Matsukura, M. et al., "Phosphorothioate analogs of oligodeoxynucleotides: Inhibitors of replication and cytopathic effects of human immunodeficiency virus", *PNAS USA* 1987, 84, 7706–7710.

Ikehara, M. et al., "Polynucleotides. LII.synthesis and properties of poly (2'–deox–2'–fluoroadenylic acid)", *Nucleic Acids Research* 1978, 5, 1877–1887.

Ikehara, M. et al., "Polynucleotides. LVI. Synthesis and Properties of Poly(2'–deoxy–2'–fluoroinosinic Acid", *Nucleic Acids Research* 1978, 5, 3315–3324.

Ikehara, M. et al., "A Linear Relationship Between Electronegativity of 2'–Substituents and conformation of Adenine Nucleosides", *Tetrahedron Letters* 1979, 42, 4073–4076.

Ikehara, M. et al., "Polynucleotides. L. synthesis and properties of poly (2'chloro–2'–deoxyadenylic acid) and poly (2'–bromo–2'–deoxyadenylic acid)", *Nucleic Acids Research* 1977, 4, 4249–4260.

Eckstein, F. et al., "Polynucleotides Containing 2'–Chloro–2'–Deoxyribose", *Biochemistry* 1972, 11, 4336–4344.

Inoue, H. et al., "Synthesis and hybridization studies on two complementary nona(2'–O–methyl) ribonucleotides", *Nucleic Acids Research* 1987, 15, 6131–6148.

Guschlbauer, W. and Jankowski, "Nucleoside conformation is Determined by the Electronegativity of the Sugar Substituent", *Nucleic Acids Research* 1980, 8, 1421–1433.

Shibahara, S. et al., "Inhibition of Human Immunodeficiency Virus (HIV–1) Replication by Synthetic Oligo–RNA Derivatives", *Nucleic Acids Research* 1987, 17, 239–252.

Stein, C.A. et al., "Physicochemical properties of phosphorothioate oligodeoxynucleotides", *Nucleic Acids Research* 1988, 16, 3209–3221.

Agarwal, K.L. and Riftina, "Synthesis and Enzymatic Properties of Deoxyribooligonucleotides Containing Methyl and Phenylphosphonate Linkages", *Nucleic Acids Research* 1979, 6, 3009–3024.

Agrawal, S. et al., "Oligodeoxynucleoside Phosphoramidates and Phosphorothioates as Inhibitors of Human Immunodeficiency Virus" *PNAS USA* 1988, 85, 7079–7083.

Agris, C.H. et al., "Inhibition of Vesicular Stomatitis Virus Protein Synthesis and Infection by Sequence–Specific Oligodeoxyribonucleoside Methylphosphonates", *Biochemistry* 1986, 25, 6268–6275.

Biggadike, K. et al., "Short convergent route to homochiral carbocyclic 2'–deoxynucleosides and carbocyclic ribonucleosides", *J. Chem. Soc. Chem. Comm.*, 1987, 1083–1084.

Butke, G. et al., *Nucleic Acid Chemistry*, 1986, Part 3, Townsend, L.B. et al., Eds., John Wiley and Sons, New York, 149–152.

Castle, R., "Imidazo[4,5–d]pyridazines. I. Synthesis of 4,7–Disubstituted Derivatives", *J. Org. Chem.*, 1958, 23, 1534–1538.

Cazenave et al., "Enzymatic Amplification of Translation Inhibition of Rabbit β–globin mRNA Mediated by AntiMessenger Oligodeoxynucleotides Cavalently Linked to Intercalating Agents", *Nucl. Acids Res.*, 1987, 15, 4717–4736.

Constant, J.F. et al., "Heterodimeric Molecules Including Nucleic Acid Bases and 9–Aminoacridine Spectroscopic Studies, Conformations and Interactions with DNA", *Biochemistry*, 1988, 27, 3997–4003.

Le Doan, P.L. et al., "Sequence–Targeted Chemical Modifications of Nucleic Acids by Complementary Oligonucleotides Covalently Linked to Porphyrins", *Nucl. Acids Res.*, 1987, 15, 8643–8659.

Gait, M.J., "Oligonucleotide Synthesis", IRL Press, 1985.

Jager, A. et al., "Oligonucleotide N–Alkylphosphoramidates: Synthesis and Binding to Polynucleotides", *Biochemistry*, 1988, 27, 7237–7246.

Jayaraman, K. et al., "Selective inhibition of *Escherichia coli* protein synthesis and growth by nonionic oligonucleotides complementary to the 3' end of 16S rRNA", *PNAS USA* 1981, 78, 1537–1541.

Jones, G. et al., "4'–substituted nucleosides. 5. hydroxymethylation of nucleoside 5'–aldehydes", *J. Org. Chem.* 1979, 44, 1309–1317.

Kazimierczuk, Z. et al., "Synthesis of 2'–deoxytubercidin, 2'–deoxyadenosine, and related 2'–deoxynucleosides via novel direct stereospecific sodium salt glycosylation procedure", *J. Am. Chem. Soc.*, 1984, 106, 6379–6382.

Knorre, D. and Vlassov, "Complementary–Addressed (Sequence–Specific) Modification of Nucleic Acids", *Prog. in Nucl. Acid Res.& Mol. Biol.*, 1985, 32, 291–320.

Miller, P.S. et al., "Nonionic Nucleic Acid Analogues. Synthesis and Characterization of Dideoxyribonucleoside Methylphosphonates", *Biochemistry* 1979, 18, 5134–5143.

Miller, P.S. et al., "Synthesis and Properties of Adenine and Thymine Nucleoside Alkyl Phosphotriesters, the Neutral Analogs of Dinucleoside Monophosphates", *J. Am. Chem. Soc.*, 1971, 93, 6657–6665.

Outten, R. and Daves, "Synthetic 1–methoxybenzo[d]naphtho[1,2–b]pyran–6–one c–glycosides", *J. Org. Chem.*, 1987, 52, 5064–5066.

Revankar et al., "Synthesis and Antiviral/Antitumor of Certain 3–Seazaguanine Nucleosides and Nucleotides", *Journal of Medicinal Chemistry* 1984, 27, 1389–1396.

Robins, M. et al, "Nucleic acid related compounds. 46. A general procedure for the efficient deoxygenation of secondary alcohols. regiospecific and stereoselective conversion of ribonucleosides to 2'–deoxynucleosides", *J. Am. Chem. Soc.* 1983, 105, 4059–4065.

Roelen, HCPF, et al., "Synthesis of nucleic acid methylphos–phonothioates", *Nucleic Acid Research*, 1988, 16, 7633–7645.

Suciu et al., "Synthesis of 9–(2, 5–dideoxy–β–D–glycero–pent–4–enofuranosyl)adenine", *Carbohydr. Res.*, 1975, 44, 112–115.

Tidd, D.M. et al., "Evaluation of N–ras oncogene anti–sense, sense and nonsense sequence methylphosphonate oligonucleotide analogues", *Anti–Cancer Drug Design*, 1988, 3, 117–127.

Smith, C. et al., "Antiviral effect of an oligo(nucleoside methylphosphonate) complementary to the splice junction of herpes simplex virus type 1 immediate early pre–mRNAs 4 and 5", *PNAS USA*, 1986, 83, 2787–2791.

Ruby, S.W. and Abelson, "An early hierarchic role of U1 small nuclear ribonucleoprotein in splicesome assembly", *Science*, 1988, 242, 1028–1035.

Stufkens, D.J., "Dynamic Jahn–Teller Effect in the Excited States of $SeCl^{6^2-}$, $SeBr^{6^2-}$, $TeCl^{6^2-}$ and $TeBr^{6^2-}$", *Rec. Trav. Chim.*, 1970, 89, 1185–1201.

Sigman, D., "Nuclease Activity of 1,10–Phenanthroline–Copper Ion", *Accounts of Chemical Research*, 1986, 19, 180–186.

Weissberger, ed., "The Chemistry of Heterocyclic Compounds, Imidazole and Derivatives", *Part 1*, Interscience, N.Y., 1953.

Yeung, A. et al., "Photoreactives and thermal properties of psoralen cross–links", *Biochemistry*, 1988, 27, 3204–3210.

Zon, G., "Synthesis of backbone–modified DNA analogues for biological applications", *Journal of Protein Chemistry*, 1987, 6, 131–145.

Van der Krol, A.R. et al., "Modulation of Eukaryotic Gene Expression by Complementary RNA or DNA Sequences", *BioTechniques*, 1988, 6, 958–973.

Loose–Mitchell, D., "Antisense Nucleic Acids as a Potential Class of Pharmaceutical Agents", *TIPS*, 1988, 9, 45–47.

Letsinger, R. et al., "Effects of pendant groups at phosphorus on binding properties of d–ApA analogues", *Nucleic Acids Research*, 1986, 14, 3487–3499.

Bhat, C., "2–Deoxy–3, 5–di–O–p–toluoyl–D–*erythro*–pentosyl Chloride" in *Synthetic Procedures in Nucleic Acid Chemistry*, 1968, vol. 1, Zorbach, ed., Interscience Publ., New York, 521–522.

Nair V., "Development of Methodologies for the Strategic Modification of Purine Ribonucleoside Systems", *Nucleosides and Nucleotides*, 1989, 8, 699–708.

Cook et al., "Synthesis and Antiviral and Enzymatic Studies of Certain 3–Deazaguanines and Their Imidazolecarboxamide Precursors", *Journal of Medicinal Chemistry*, 1978, 21, 1212–1218.

Ikehara, M. et al.,"Studies of Nucleosides and Nucleotides–LXXIV$^{1}$", *Tetrahedron*, 1978, 34, 1133–1138.

Ikehara, M. et al., "Studies of Nucleosides and Nucleotides–LXV$^{1}$", *Tetrahedron*, 1975, 31, 1369–1372.

Ikehara, M., "Studies of Nucleosides and Nucleotides–LXXXII.$^{1)}$ cyclonucleosides. (39).$^{2)}$ synthesis and properties of 2'halogen–2'–deoxyadenosines", *Chemistry and Pharmaceutical Bulletin*, 1978, 26, 2449–2453.

Ikehara, M., "Studies of Nucleosides and Nucleotides–LXXIX.1), Purine cyclonucleosides. (37). The total synthesis of an antibiotic 2'–amino–2'deoxyguanosine2)", *Chemistry and Pharmaceutical Bulletin*, 1978, 26, 240–244.

Ikehara, M., "Purine 8–Cyclonucleosides", *Accounts of Chemical Research*, 1969, 2, 47–53.

Ranganathan, R., "Modification of the $2^1$–Position of Purine Nucleosides: Synthesis of $2^1$–a–Substituted–$2^1$–Deoxyadenosine Analogs", *Tetrahedron Letters*, 1977, 15, 1291–1294.

Markiewicz, W. and Wiewiorowski, "Nucleic Acid Chemistry", Part 3, pp. 229–231, Townsend, L. and Tipson, eds., J. Wiley and Sons, New York, 1986.

Schmidt, Richard R. et al., "C–Glycosides from O–Glycosyl Trichloroacetimidates" *Tetrahedron Letters*, 1982, 23, 409–412.

Fox, J. et al., "Nucleosides. XVIII. Synthesis of 2'–Fluorothymidine, 2'–Fluorodeoxyuridine, and Other 2'–Halogeno–2'–Deoxy Nucleosides", *Journal of Organic Chemistry*, 1964, 29, 558–564.

Jarvi, E.T. et al., "Synthesis and biological evaluation of dideoxynucleosides containing a difluoromethylene unit", *Nucleosides and Nucleotides*, 1989, 8, 1111–1114.

Hertel, L.W. et al., "Synthesis of 2–Deoxy–2,2–difluoro––D–ribose and 2–Deoxy–2,2–difluoro–D–ribofuranosyl Nucleosides", *Journal of Organic Chemistry*, 1988, 53, 2406–2409.

Chladek, S. et al., "Facile Synthesis of 2'–Amino–2'–Deoxyadenosine", *Journal of Carbohydrates, Nucleosides & Nucleotides*, 1980, 7, 63–75.

Parkes, K. and Taylor, "A Short Synthesis of 3'–Cyano–3'–Deoxythymidine", *Tetrahedron Letters*, 1988, 29, 2995–2996.

De las Heras, F. et al., "3'–C–Cyano–3'–Deoxythymidine", *Tetrahedron Letters*, 1988, 29, 941–944.

Pfitzner, K.E. and Moffatt, J.G., "The synthesis of nucleoside–5' aldehydes", *Journal of American Chemical Society*, 1963, 85, 3027.

Youssefyeh, R. et al., "Synthetic routes to 4'–hydroxymethlnucleosides", *Tetrahedron Letters*, 1977, 435–438.

Balaban, I. and Pyman, "Bromo–Derivatives of Glyoxaline", *Journal of Chemical Society*, 1922, 121, 947–958.

Mitsunobu, "The Use of Diethyl Azodicarboxylate and Triphenylphosphine in Synthesis and Transformation of Natural Products", *Synthesis*, 1981, 1–28.

Daves, G. and Cheng, "The Chemistry and Biochemistry of C–Nucleosides", *Progress in Medicinal Chemistry*, 1976, 13, 304–349.

Arnott and Hukins, "Optimized Parameters for A–DNA and B–DNA" *Biochemical and Biophysical Research Communication*, 1970, 47, 1504–1510.

Caruthers, M., "Oligonucleotides. Antisense Inhibitors of Gene Expression", Cohen, J.S., ed., pp. 7–24, CRC Press, Inc., Boca Raton, FL 1989.

Beaucage, S. et al., "Deoxynucleoside phosphoramidites—A new class of key intermediates for deoxypolynucleotide synthesis", *Tetrahedron Letters*, 1981, 22, 1859–1862.

Gaffney, B. and Jones, "A New Strategy for the Protection of Deoxyguanosine During Oligonucleotide Synthesis", *Tetrahedron Letters*, 1982, 23, 2257–2260.

Seela, F. and Kehne, "Palindromic Octa– and Dodecanucleotides Containing 2'–Deoxytubercidin: Synthesis, Hairpin Formation, and Recognition by the Endodeoxyribonuclease EcoRI", *Biochemistry*, 1987, 26, 2233–2238.

Ikehara, M. et al., "Improved Synthesis of 2'–Fluoro–2'–Deoxyadenosine and Synthesis and Carbon–13 NMR Spectrum of Its 3',5'–Cyclic Phosphate Derivative", *Nucleosides and Nucleotides*, 1983, 2, 373–385.

Jones, R.A., "Transient protection: Efficient one–flask synthesis of protected deoxynucleosides", *J. Am. Chem. Soc.,* 1982, 104, 1316–1319.

Ogilvie, K., "Solution and Solid Phase Chemical Synthesis of Arabinonucleotides", *Can. J. Chem.,* 1989, 67, 831–839.

Reese, C. et al., "4'(1,2,4–Triazol–1–yl)–and 4'(3'Nitro'1,2,4–triazol–1–yl)–1–(β–D–2,3,5–tri–O–acetylarabinofuranosyl)pyrimidin–2(1H)–ones. Valuable Intermediates in the Synthesis of Derivatives of 1–(β–D–Arabinofuranosyl)cytosine (Ara–C)", J. Chem. Soc. Perkin Trans I, 1982, 1171–1176.

Bhat, V. et al., "A Simple and Convenient Method for the Selective N–Acylations of Cytosine Nucleosides", *Nucleosides and Nucleotides,* 1989, 8, 179–183.

Ikehara, M. et al., "Studies of Nucleosides and Nucleotides–LXXXVII.1), Purine cyclonucleosides. XLII. synthesis of 2'deoxy–2'fluorofunaosine", *Chemical and Pharmaceutical Bulletin,* 1981, 29, 1034–1038.

Ikehara, M. et al, "Studies of Nucleosides and Nucleotides–LXXXIX., Purine cyclonucleosides. (43). synthesis and properties of 2'halogen–2'–deoxyguanosines1)", *Chemical and Pharmaceutical Bulletin,* 1981, 29, 3281–3285.

Robins, M., "2'– and 3'–Ketonucleosides and their *Arabino* and *Xylo* Reduction Products" *Tetrahedron,* 1984, 40, 125–135.

Ogilvie, K., "Prevention of Chain Cleavage in the Chemical Synthesis of 2'–silylated Oligoribonucleotides", *Nucleic Acids Research,* 1989 17, 3501–3517.

Chen, Y. et al., "Studies on Fluoroalkylation and Fluroalkoxylation. Part 33. Direct Trifluoromethylation of Aryl Halides with Fluorosulphonyldifluoromethyl Iodide in the Presence of Copper: an Electron Transfer Induced Process", *J. Chem. Soc. Perkin Transactions,* 1989, 2385–2387.

Sproat, B.S. et al., "New synthetic routes to protected purine 2'–O–methylriboside–3'–O–phosphoramidites using a novel alkylation procedure", *Nucleic Acids Research* 1990, 18, 41–49.

Freskos, J., "Synthesis of 2'Deoxypyrimidine Nucleosides Via Copper (I) Iodide Catalysis", *Nucleosides and Nucleotides* 1989, 8, 1075–1076.

Sproat, B. et al., "Highly Efficient Chemical Synthesis of 2'–O–methyloligoribonucleotides and Tetrabiotinylated Derivatives; Novel Probes that are Resistant to Degradation by RNA or DNA Specific Nucleases", *Nucleic Acids Research* 1989, 17, 3373–3386.

Iyer, R., Beaucage, Serge L. et al., "3H–1,2–benzodithiole–3–one 1,1–dioxide as an improved sulfurizing reagent in the solid–phase synthesis of oligodeoxyribonucleoside phosphorothiioates", *Journal of American Chemical Society* 1990, 112, 1253–1255.

Koole, L. et al., "Synthesis of phosphate–methylated DNA fragments using 9–fluorenylmethoxycarbonyl as transient base protecting group", *Journal of Organic Chemistry* 1989, 54, 1657–1664.

Graham, M.J. et al., "Tritium Labeling of Antisense Oligonucleotides by Exchange wiht Tritiated Water", *Nucleic Acids Res.* 1993, 21(16), 3737–3743.

Daves, G. and Cheng, *Progress in Medicinal Chemistry* 1978, 14, 304–349.

Englisch, et al., "Chemically Modified Oligonucleotides as Probes and Inhibitors" *Angew. Chem. Int. Ed. Eng.* 1991, 30, 613.

Goodchild, "Conjugates of Oligonucleotides and Modified Oligonucleotides: A Reviw of Their Synthesis and Properties" *Bioconjugate Chemistry* 1990, 1, 165.

Mitchell, et al., "Boron trifluoride methanol complex as a non–depurinating detritylating agent in DNA synthesis", *Nucl. Acids Res.,* 1990, 18, 5321.

Manoharan, et al., "Chemical Modifications to Improve Uptake and Bioavailability of Antisense Oligonculeotides" *Database Embase Elsevier Science Publishers* 1992 660, 306 (abstract).

Schwartz et al., "The DNA by Acetylaminofluorene residues and by apurinic sites", *J. Mol. Biol.,* 1989, 207, 445–450.

Adams, "Intercellular Adhesion Molecule 1 on Liver Allografts During Rejection", *Lancet,* Nov. 11, 1989, 1122–1125.

Bevilacqua et al., "Endothelial Leukocyte Adhesion Molecule 1: An Inducible Receptor for Neutrophils related to Complement Regulatory Proteins and Lectins", *Science,* 1989, 243, 1160–1165.

Bevilacqua et al., "Identification of an inducible endothelial–leukocyte adhesion molecule", *Proc. Natl. Acad. Sci.,* 1987, 84, 9238–9242.

Cosimi et al., "In Vivo Effects of Monoclonal Antibody to ICAM–1 (CD54) in Nonhuman Primates with Renal Allografts", *J. Immunol.,* 1990, 144, 4604–4612.

Dustin et al., "Lymphocyte Function–associated Antigen–1 (LFA–1) Interaction with Intercellular Adhesion Molecule–1 (ICAM–1) is One of At Least Three Mechanisms for Lymphocyte Adhesion to Cultured Endothelial Cells", *J. Cell Biol.,* 1987, 107, 321–331.

Faull et al., "Tubular Expression of Intercellular Adhesion Molecule–1 During Renal Alllograft Rejection", *Transplantation,* 1989, 48, 226–230.

Frohman et al., "The Induction of Intercellular Adhesion Molecule–1 (ICAM–1) Expression on Human Fetal Astrocytes by interferon–γ, tumor necrosis factor α, lymphotoxin, and interleukin–1: relevance to intracerebral antigen presentation", *J. Neuroimmunol.,* 1989, 23, 117–124.

Harlan, J.M. et al., "Leukocyte–Endothelial Interactions", *Blood,* 1985, 65, 513–525.

Isobe et al., "Specific Acceptance of Cardiac Allograft After Treatment with Antibodies to ICAM–1 and LFA–1", *Science,* 1992, 255, 1125–1127.

Isobe et al., "Early Detection of Rejection and Assessment of Cyclosporine therapy by $^{111}$In Antimyosin Imaging in Mouse Heart Allografts", *Circulatiom,* 1991, 84, 1246–1255.

Nielsen, P.E. et al., "Sequence–Selective Recognition of DNA by Strand Displacement with a Thymine–Substituted Polyamide", *Science,* 1991, 254, 1497–1500.

Osborn et al., "Direct Expression Cloning of Vascular Cell Adhesion Molecule 1, a Cytokine–Induced Endothelial Protein that Binds of Lymphocytes", *Cell,* 1989, 59, 1203–1211.

Rice et al., "An Inducible Endothelial Cell Surface Glycoprotein Mediates Melanoma Adhesion", *Science,* 1989, 246, 1303–1306.

Rice et al., "Inducible Cell Adhesion Molecule–110 (INCAM–110) is an Endothelial Receptor for Lymphocytes", *J. Exp. Med.,* 1990, 171, 1369–1374.

Staunton, D.E. et al., "Primary Structure of ICAM–1 Demonstrates Interaction between Members of the Immunoglobulin and Intergrin Supergene Families", *Cell,* 1988, 52, 925–933.

Wellicome et al., "A Monoclonal Antibody that Detects A Novel Antigen on Endothelial Cells is Induced by Tumor Necrosis Factior, IL–1, or Lipopolysaccharide", *J. Immunol.*, 1990, 144, 2558–2565.

Zucker, M. et al., "On Finding All Suboptimal Foldings of n RNA Molecule", *Science*, 1989, 244, 48–52.

Petersheim, M. et al., "Base–Stacking and Base–Pairing Contributions to Helix Stability: Thermodynamics of Double Helix Formation with CCGG, CCGGp, CCGGAp, ACCGGp, CCGGUp, and ACCGGUp", *Biochem.*, 1983, 22, 256–263.

Akhtar et al., "Cellular uptake and intracellular fate of antisense oligonucleotides", *Trends in Cell Biol.*, 1992, 2, 139.

Alahari et al., The fission yeast $prp4^+$ gene involved in Pre–mRNA splicing codes for a predicted serine/threonine kinase and is essential for growth, *Nucl. Acids Res.*, 1993, 21, 4079.

Bennett et al., "Cationic Lipids Enhance Cellular Uptake and Activity of Phosphorothioate Antisense Oligonucleotides", *Mol. Pharm.*, 1992, 41, 1023.

Berkow et al., Eds., *The Merck Manual of Diagnosis and Therapy*, 1987, 15th Ed., Rahay, NJ, 1206–1228.

Bradley et al., "P–glycoprotein, multidrug resistance and tumor progression", *Cancer Metastasis Rev.*, 1994, 13, 223.

Brigstock et al., "Species–Specific High Molecular Weight Forms of Basic Fibroblast Growth Factor", *Growth Factors*, 1990, 4, 45.

Chabner et al., "Reversal of Multidrug Resistance", *J. Clin. Oncol.*, 1991, 9, 4.

Chen et al., "Genomic Organization of the Human Multidrug Resistance (MDR1) Gene and Origin of P–glycoproteins", *J. Biol. Chem.*, 1990, 265, 506.

Corrias et al., "An Oligomer Complementary to the 5' End Region of MDR1 Gene Decreases Resistance to Doxorubicin of Human Adenocarcinoma–Resistant Cells", *Anticancer Res.*, 1992, 12, 1431.

Crooke et al., "Pharmacokinetic Properties of Several Novel Oligonucleotide Analogs in mice", *J. Pharmacol. Exp. Ther.*, 1996, 277, 923.

Dean et al., "Inhibition of Protein Kinase C–α Expression in Human A549 Cells by Antisense Oligonucleotides Inhibits Induction of Intercellular Adhesion Molecule 1 (ICAM–1) mRNA by Phorbol Esters", *J. Biol. Chem.*, 1994, 269, 16416.

DeVirgilio et al., "Cloning and Disruption of a Gene Required for Growth on Acetate but not on Ethanol: the Acetyl–Coenzyme A Synthetase Gene of *Saccharomyces cerevisiae*", *Yeast*, 1992, 8, 1043.

Efferth et al., "Modulation of P–Glycoprotein–Mediated Multidrug Resistance by Monoclonal Antibodies, Immunotoxins of Antisense Oligodeoxynucleotides in Kidney Carcinoma and Normal Kidney Cells", *Oncology*, 1993, 50, 303.

French et al., "Expression of Two Related Nonstructural Proteins of Bluetongue Virus (BTV) Type 10 in Insect Cells by a Recombinant Baculovirus: Production of Polyclonal Ascitic Fluid and Characterizatrion of the Gene Product in BTV–Infected BHK Cells", *J. Virology*, 1989, 63, 3270.

Gao et al., "Cloning and Characterization of a Mouse Gene with Homology to the Human von Hippel–Lindau Disease Tumor Surpressor Gene: Implications for the Potential Organization of the Human von Hippel–Lindau Disease Gene", *Cancer Res.*, 1995, 55, 743.

Gelbert et al., "Analysis of GPT Activity in Mammalian Cells with a Chromosomally Integrated Shuttle Vector Containing Altered gpt Genes", *Cell. Mol. Genet.*, 1990, 16, 173.

Gold et al., *Escherichia coli and Salmonella typhimurium: Cellular and Molecular Biology*, 1987, vol. 2, Neidhardt et al., eds., American Society for Microbiology, Washington, D.C., 1303.

Gottesman et al., "The Multidrug Transporter, a Double–edged Sword", *J. Biol. Chem.*, 1988, 263, 12163.

Ho et al., "Potent Antisense oligonucleotides to the human multidrug resistance–1 mRNA are rationally selected by mapping RNA accessible sites with oligonucleotide libraries", *Nucl. Acids Res.*, 1996, 24, 1901.

Ishida et al., "Multidrug Resistance in Cultured Human Leukemia and Lymphoma Cell Lines Detected by a Monoclonal Antibody, MRK16", *Jpn. J. Cancer Res.*, 1989, 80, 1006.

Kabanov, A.V., "A new class of antivirals: antisense olgonucleotides combined with a hydrophobic substituent effectively inhibit influenza virus reproduction and synthesis of virus–specific proteins in MDCK cells", *FEBS Letts.*, 1990, 259, 327–330.

Kanagasundaram, V. et al., "Isolation and Characterization of the gene encoding gluconolactonase from *Zymomonas mobilis*", *Biochimica et Biophysica Acta*, 1992, 1171, 198–200.

Kane et al., "A new vector using the human multidrug resistance gene as a selectable marker enables overexpression of foreign genes in eukaryotic cells", *Gene*, 1989, 84, 439.

Kaji et al., "Structurally Distinct MDR Modulators Show Specific Patterns of Reversal Against P–Glycoproteins Bearing Unique Mutations at Serine$^{939/941}$", *Biochemistry*, 1994, 33, 5041.

Kiehntopf et al., "Ribozyme–mediated cleavage of the MDR–1 transcript restores chemosensitivity in previously resistant cancer cells", *EMBO J.*, 1994, 13, 4645.

Kobayashi et al., "Reversal of Drug Sensitivity in Multidrug–Resistant Tumor Cells by an MDR1 (PG1) Ribozyme", *Cancer Res.*, 1994, 54, 1271.

Krieg, A.M. et al., "Modification of antisense phosphodiester oligonucleotides by a 5' cholesteryl moiety increases cellular association and improves efficacy", *Proc. Nat'l. Acad. Sci.*, 1993, 90, 1048–1052.

MacKellar, C. et al., "Synthesis and physical properties of anti–HIV antisense oligonucleotides bearing terminal lipophilic groups", *Nucl. Acids Res.*, 1992, 20, 3411–3417.

Manoharan, M. et al., "Lipidic Nucleic Acids", *Tetrahedron Letts.*, 1995, 36, 3651–3654.

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770.

Manoharan M. et al., "Cholic Acid–Oligonucliotide Conjugates for Antisense Applications", *Bioorganic Med. Chem. Letts.*, 1994, 4, 1053–1060.

Manoharan M. et al.,"Oligonucleotide Conjugates: Alteration of the Pharmacokinetic Properties of Antisense Agents", *Nucleosides and Nucleotides*, 1995, 14, 969–973.

Martin, P., "Ein neuer Zugang zu 2'–O–Alkylribonucleosiden und Eigenschaften deren Oligonucleotide", *Helvetica Chemica Acta*, 1995, 78, 486–504.

Markussen et al., "Translational control of *oskar* generates a Short OSK, the isoform that induces pole plasm assembly", *Development*, 1995, 121, 3723.

McDermott et al., "Structure and lens expression of the gene encoding chicken βA3/A1–crystallin", *Gene*, 1992, 117, 193.

Mishra, R.K. et al., "Improved leishmanicidal effect of phosphorotioate antisense oligonucleotides by LDL–medicated delivery", *Biochim. Et Biophysica*, 1995, 1264, 229–237.

Monaco, L. et al., "Structure of Two Rat Genes Coding for Closely Related Rolipram–sensitive cAMP Phosphodiesterases", *J. Biol. Chem.*, 1994, 269, 347–357.

Oberhauser, B. et al., "Effective incorporation of 2'–O–methyl–oligonucleotides into liposomes and enhanced cell association through modification with thiocholesterol", *Nucl. Acids Res.*, 1992, 20, 533–538.

Olsen, S.R. et al., "Inhibition of Protein Kinase–A by Overexpression of the Cloned Human Protein Kinase Inhibitor", *Mol. Endocrinol.*, 1991, 5, 1246–1256.

Palfner et al., "Improvement of Hammerhead Ribozymes Cleaving mdr–1 RNA", *Biol. Chem. Hoppe–Seyler*, 1995, 376, 289.

Perri et al., "Interactions of Plasmid–encoded Replication Initiation Proteins with the Origin of DNA Replication in the Broad Host Range Plasmid RK2", *J. Biol. Chem.*, 1991, 266, 12536.

Pushpa–Reka, T.R. et al., "Rat Phospholipid–hydroperoxide Glutathione Peroxidase", *J. Biol. Chem.*, 1995, 270, 26993–26999.

Richert et al., "Stability and Covalent Modification of P–Glycoprotein in Multidrug–Resistant KB Cells", *Biochemistry*, 1988, 28, 7607.

Rogers. R.P. et al., "Alternative splicing dictates translational start in Epstein–Barr virus transcripts", *EMBO J.*, 1990, 9, 2273–2277.

Roninson, "The Role of the MDR1 P–Glycoprotein Gene in Multidrug Resistance In Vitro and In Vivo", *Biochem. Pharmacol.*, 1992, 43, 95.

Saison–Behmoaras, T. et al., "Short modified antisense oligonucleotides directed against Ha–*ras* point mutation induce selective cleavage of the mRNA and inhibit T24 cells proliferation", *EMBO J.*, 1991, 10, 1111–1118.

Sambrook et al. (eds.), "Preparation of Radiolabeled DNA and RNA Probes", *Molecular Cloning: A Laboratory Manual*, 1989, 2d. Ed., Chapter 10, 10.59.

Saul, D.J. et al., "*cel*B, a Gene Coding for a Bifunctional Cellulase from the Extreme Thermophile *Caldocellum saccharolyticum*", *Applied & Env. Microbiol.*, 1990, 56, 3117–3124.

Scanlon et al., "*Ribo*zyme–mediated reversal of the multidrug–resistant phenotype", *Proc. Natl. Acad. Sci.*, 1994, 91, 11123.

Shoji et al., "Mechanism of cellular uptake of modified oligodeoxynucleotides containing methylphosphonate linkages", *Nucl. Acids Res.*, 1991, 19, 5543.

Svinarchuk, F.P. et al., "Inhibition of HIV proliferation in MT–4 cells by antisense oligonucleotide conjugated to lipophilic groups", *Biochimie*, 1993, 79, 49–54.

Thierry et al., "Overcoming multidrug resistance in human tumor cells using free and liposomally encapsulated antisense oligodeoxynucleotides", *Biochem. Biophys. Res. Comm.*, 1993, 190, 952.

Twentyman et al., "A Comparison of Thodamine 123 Accumulation and Efflux in Cells with P–Glycoprotein–mediated and MRP–associated Multidrug Resistance Phenotypes", *Eur. J. Cancer*, 1994, 30, 1360.

Vasanthakumar et al., "Modulation of Drug Resistance in Daunorubicin Resistant Subline with Oligonucleoside Methylphosphonates", *Cancer Comm.*, 1989, 1, 225.

Yaoita, Y. et al., "*Xenopus laevis* α and β thyroid hormone receptor", *Proc. Natl. Acad. Sci.*, 1990, 87, 7090–7094.

Weiss, R., "Upping the Antisense Ante: Scientists bet on profits from reverse genetics", *Science News*, 1991, 139, 108–109.

Westermann, P. et al., "Inhibition of expression of SV40 virus large T–antigen by antisensse oligodeoxyribonucleotides", *Biomed. Biochim. Acta.*, 1989, 48, 85–93.

Tseng, B.Y. et al., "Antisense oligocucleotide technology in the development of cancer therapeutics", *Cancer Gene Therapeutics*, 1994, 1, 65–71.

Uhlmann, E. et al., "Antisense Oligonucleotides: A New Therapeutic Principle", *Chem. Reviews*, 1990, 90, 544–584.

James, W., "Towards gene–inhibition therapy: a review of progress and prospects in the field of antiviral antisense nucleic acids and ribozymes", *Antiviral Chem. & Chemotherapy*, 1991, 2, 191–214.

Chen et al., "Mechanism of Action of the Novel Anticancer Agent 6–Fluoro–2–(2'–fluoro–1,1'–biphenyl–4–yl)–3methyl–4quinolinecarboxylic Acid Sodium Salt (NSC 368390): Inhibition of *de Novo* Pyrimidine Nucleotide Biosynthesis", *Cancer Res.*, 1986, 46, 5014–5019.

Chiang, M–Y. et al., "Antisense Oligonucleotides Inhibit Intercellular Adhesion Molecule 1 Expression by Two Distince Mechanisms", *J. Biol. Chem.*, 1991, 266, 18162–18171.

Chou, T–C et al., "Quantitative Analysis of Dose–Effect Relationships: The Combined Effects of Multiple Drugs or Enzyme Inhibitors", *Adv. Enz. Regul.*, 1984, 22, 27–55.

Haug et al., "A Phase I Trial of Immunosuppression with Anti–ICAM–1 (CD54) mAb in Renal Allograft Recipients", *Transplantation*, 1993, 55, 766–773.

Kahan, B.D. et al., "The Synergistic Interaction is vitro and in vivo of Brequinar Sodium with Cyclosporine or Rapamycin Alone and in Triple Combination", *Transplantation*, 1993, 55, 894–900.

Kitajima et al., "Ablation of Transplanted HTLV–I Tax–Transformed Tumors in Mice by Antisense Inhibition of NF–κB", *Science*, 1992, 258, 1792–1795.

Liu, J. et al., "Calcineurin Is a Common Target of Cyclophilin–Cyclosporin A and FKBP–FK506 Complexes", *Cell*, 1991, 66, 807–815.

Monaco et al., "Studies on Heterologous Anti–Lymphocyte serum in Mice", *J. Immunol.*, 1966, 96, 229–238.

Morice et al., "Rapamycin–induced Inhibition of p34$^{cdc2}$ Kinase Activation is Associated with $G_1S$–Phase Growth Arrest in Lynphocytes", *J. Biol. Chem.*, 1993, 268, 3734–3738.

Nickoloff et al., "Accessory Cell Function of Keratinocytes for Superantigens", *J. Immunol.*, 1993, 150, 2148–2159.

Simons et al., "Antisense c–*myb* oligonucleotides inhibit intimal arterial smooth muscle cell accumulation in vivo", *Nature*, 1992, 359, 67–70.

Anderson et al., "Leukocyte Adhesion Deficiency: An Inherited Defect in the Mac–1, LFA–1, and p150,95 Glycoproteins", *Ann. Rev. Med.*, 1987, 38, 175–194.

Campbell et al., "Intercellular adhesion molecule 1 is induced on isolated endocrine islet cells by cytokines but not by retrovirus infection", *Proc. Natl. Acad. Sci.,* 1989, 86, 4282–4286.

Cooney, M. et al., "Site–Specific Oligonucleotide Binding Represses Transcription of the Human c–myc Gene in Vitro", *Science,* 1988, 241, 456–459.

Eder, P.S. et al., "Substrate Spcificity and Kinetics of Degradation of Antisense Oligonucleotides by a 3' Exonuclease in Plasma", *Antisense Res. & Dev.,* 1991, 1, 141–151.

Gibbs, W.W. et al., "State of Shock: Sepsis can be fatal to firms as wall as to patients", *Scientific American,* Oct. 1994, 133–134.

Goodchild, J. et al., "Inhibition of human immunodeficiency virus replication by antisense oligodeoxynucleotides", *Proc. Natl. Acad. Sci.,* 1988, 85, 5507–5511.

Greve et al., "The Major Human Rhinovirus Receptor is ICAM–1", *Cell,* 1989, 56, 839–847.

Griffiths et al., "Keratinocyte Intercellular Adhesion Molecule–1 (ICAM–1) Expression Preceedes Derman T Lymphocyte Infiltration in Allergic Contact Dermatitis (*Rhus dermatitis*)", *Am. J. Pathology.,* 1989, 135, 1045–1053.

Hale et al., "Immunohistologic Analysis of the Distribution of Cell Adhesion Molecules within the Inflammatory Synovial Microenvironment", *Arth. Rheum.,* 1989, 32, 22–30.

Ho et al., "Treatment of severe lichen planus with cyclosporine", *J. Am. Acad. Dermatol.,* 1990, 22, 64–68.

Kibler–Herzog, L. et al., "Duplex stabilities of phophorothioate, methylphosphonate, and RNA analogs of two DNA 14–mers", *Nucl. Acids Res.,* 1991, 19, 2979–2986.

Lisby et al., "Intercellular adhesion molecule–1 (ICAM–1) expression correlated to inflammation", *Br. J. Dermatol.,* 1989, 120, 479–484.

Marlin et al., "A soluble form of intercellular adhesion molecule–1 inhibits rhinovirus infection", *Nature,* 1990, 344, 70–72.

Miller, P.S. et al., "A New approach to chemotherapy based on molecular biology and nucleic acid chemistry: Matagen (masking tape for gene expression)", *Anti–Cancer Drug Des.,* 1987, 2, 117–128.

Miller, D.E. et al., "Cytokine Modulation of Intercellular Adhesion Molecule–1 Surface Expression of Human Melanoma Cells; Correlation with Adhesion of Peripheral Blook Leukocytes", *Proc. Am. Assoc. Cancer Res.,* 1990, 31, 60, Abstract 353.

Mirabelli, C. et al., "In vitro and in vivo pharmacologic activities of antisense oligonucleotides", *Anti–Cancer Drug Des.,* 1991, 6, 647–661.

Okayasu, I. et al., "A Novel Method in the Induction of Reliable Experimental Acute and Chronic Ulcerative Colitis in Mice", *Gastroenterology,* 1990, 98, 694–702.

Rice, G.E. et al., "An Inducible Endothelial Cell Surface Glycoprotein Mediates Melanoma Adhesion", *Science,* 1989, 246, 1303–1306.

Rothenberg, M. et al., "Oligodeoxynucleotides as AntiSense Inhibitors of Gene Expression: Therapeutic Implications",*J. Natl. Cancer Inst.,* 1989, 81, 1539–1544.

Staunton, D.E. et al., "Primary Structure of ICAM–1 Demonstrates Interaction between Members of the Immunoglobulin and Intergrin Supergene Families",*Cell,* 1988, 52, 925–933.

Stein, C.A. et al., "Oligodeoxynucleotides as Inhibitors of Gene Expression: A Review", *Cancer Res.,* 1988, 48, 2659–2668.

Stein, C. et al., "Antisense Oligonucleotides as Therapeutic Agents—Is the Bullet Really Magical?", *Science,* 1993, 261, 1004–1012.

Staunton et al., "A Cell Adhesion Molecule, ICAM–1, is the Major Surface Receptor for Rhinoviruses", *Cell,* 1989, 56, 849–853.

Staunton et al., "The Arrangement of the Immunoglobin––like Domains of ICAM–1 and the Binding Sites for LFA–1 and Rhinovirus", *Cell,* 1990, 61, 243–354.

Shiohara et al., "Fixed Drug Eruption: Expression of Epidermal Keratinocyte Intercellular Adhesion Molecule–1 (ICAM–1)", *Arch. Dermatol.,* 1989, 125, 1371–1376.

Tseng, B. et al., "Antisense oligonucleotide technology in the development of cancer therapeutics", *Cancer Gene Therapeutics,* 1994, 1, 65–71.

Uhlmann, E. et al., "Antisense Oligonucleotides: A New Therapeutic Principle", *Chem. Rev.,* 1990, 90, 543–584.

Weetman et al., "Expression of an intercellular adhesion molecule, ICAM–1, by human thyroid cells", *J. Endocrinol.,* 1989, 122, 185–191.

Wegner et al., "Intercellular Adhesion Molecule–1 (ICAM–1) in the Pathogenesis of Asthma", *Science,* 1990, 247, 456–459.

Weiss, R., "Upping the Antisense Ante: Scientists bet on profits from reverse genetics", *Science News,* 1991, 139, 108–109.

Westerman, P. et al., "Inhibition of expression of SV40 virus large T–antigen by antisense oligodeoxyribonucleotides", *Biomed. Biochim. Acta,* 1989, 48, 85–93.

Zhang, R. et al., "Hematopoietic development of vav$^{-/}$ mouse embryonic stem cells", *Proc. Natl. Acad. Sci.,* 1994, 91, 12755–12759.

Zon, G., "Oligonucleotide Analogues as Potential Chemotherapeutic Agents", *Pharm. Res.,* 1988, 5, 539–547.

Ohtsuka, I. et al., "Recognition by Restriction Endonuclease *Eco*RI of Deoxyoctanucleotides Containing Modified Sugar Moieties", *European Journal of Biochemistry* 1984, 139, 447–450.

Brill, W. et al., "Synthesis of of oligodeoxynucleoside phosphorodithioates via thioamidites", *J. Am. Chem. Soc.,* 1989, 111, 2321–2322.

Miller, P.S. et al., "Biochemical and Biological Effects of Nonionic Nucleic Acid Methylphosphonates", *Biochemistry,* 1981, 20, 1874–1880.

Graham, M.J. et al., "Tritium Labeling of Antisense Oligonucleotides by Exchange with Tritiated Water", *Nucleic Acids Res.,* 1993, 21(16), 3737–3743.

Agrawal, S., "Functionalization of Oligonucleotides with Amino Groups and Attachment of Amino Specific Reporter Groups", *Methods in Molecular Biology,* 1994, vol. 26, Chapter 3, Human Press Inc., Totowa, NJ, 93–120.

Bochner, B.S. et al., "Adhesion of Human Basophils, Eosinophils, and Neutrophils to Interleukin 1–activated Human Vascular Endothelial Cells: Contributions of Endothelial Cell Adhesion Molecules", *J. Exp. Med.,* 1991, 173, 1553–1556.

Boutorin, A.S. et al., "Synthesis of akylating oligonucleotide derivatives containing cholesterol or phenazinium residues at their 3'–terminus and their interaction with DNA within mammalian cells", *FEBS Letts.,* 1989, 254, 129–132.

Carlos, T. et al., "Human Monocytes Bind to Two Cytokine–Induced Adhesive Ligands on Cultured Human Endothelial Cells: Endothelial–Leukocyte Adhesion Molecule–1 and Vascular Cell Adhesion Molecule–1", *Blood,* 1991, 77, 2266–2271.

Chen, C. et al., "Internal Duplication and Homology with Bacterial Transport Proteins in the mdr1 (P–Glycoprotein) Gene from Multidrug–Resistant Human Cells", *Cell,* 1986, 47, 381–389.

Chirgwin, J.M. et al., "Isolation of Biologically Active Ribonucleic Acid from Sources Enriched in Ribonuclease", *Biochemistry,* 1979, 18, 5294–5299.

Crooke, S.T. et al., "Progress in the development and patenting of antisense drug discovery technology", *Exp. Opin. Ther. Patents,* 1996, 6, 855–870.

de Smidt, P.C. et al., "Association of antisense oligonucleotides with lipoproteins prolongs the plasma half–life and modifies the tissue distribution", *Nucl. Acids Res.,* 1991, 19, 4695–4700.

Gmeiner, W.H et al., "Development of and Efficient Oligonucleotide Derivation Protocol", *Bioorg. & Med. Chem. Letts.,* 1991, 1, 487–490.

Hotoda, H. et al., "Biologically Active Oligodeoxyribonucleotides—II: Structure Activity Relationships of Anti–HIV–1 Pentadecadeoxyribonucleotides Bearing 5'–End–Modifications", *Nucleosides & Nucleotides,* 1994, 13, 1375.

Ing, N.H. et al., "In vivo transcription of a progesterone–responsive gene is specifically inhibited by a triplex–forming oligonucleotide", *Nucl. Acids Res.,* 1993, 21, 2789.

Kishimoto, T.K. et al., "The Leukocyte Integrins", *Adv. Immunol.,* 1989, 46, 149–182.

Iyer, R. al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.,* 1990, 112, 1253–1254.

Reed, M.W. et al., "Acridine– and Cholesterol–Derivatized Solid Supports for Improved Synthesis of 3'–Modified Oligonucleotides", *Bioconjugate Chem..,* 1991, 2, 217.

* cited by examiner

COMPOSITIONS AND METHODS FOR ENHANCED BIOSTABILITY AND ALTERED BIODISTRIBUTION OF OLIGONUCLEOTIDES IN MAMMALS

CROSS REFERENCE TO RELATED APPLICATIONS

This Application is a continuation of U.S. provisional application Ser. No. 08/928,823 filed Sep. 12, 1997, which is a continuation-in-part of (I) application Ser. No. 08/464,953, filed Jun. 5, 1995, which is a continuation-in-part of application Ser. No. 08/117,363, filed Sep. 3, 1993, which is a continuation-in-part of application Ser. No. PCT/US92/09196, filed Oct. 23, 1992 (now application Ser. No. 08/211,882, filed Apr. 22, 1994), which is a continuation-in-part of application Ser. No. 07/782,374, filed Oct. 24, 1991 (now abandoned), which is a continuation-in-part of (A) application Ser. No. 07/463,358, filed Jan. 11, 1990 (now abandoned), and (B) a CIP of application Ser. No. 07/566,977, filed Aug. 13, 1990 (now abandoned); and a CIP of (II) application Ser. No. 08/344,155, filed Nov. 23, 1999 now U.S. Pat. No. 5,883,082, which is a continuation-in-part of application Ser. No. 08/063,167, filed May 17, 1993 (now U.S. Pat. No. 5,514,788), which is a continuation-in-part of application Ser. No. 08/007,997 (now U.S. Pat. No. 5,591,623), filed Jan. 21, 1993, which is a continuation-in-part of application Ser. No. 07/939,855, filed Sep. 2, 1992 (now abandoned), which is a continuation-in-part of application Ser. No. 07/567,286, filed Aug. 14, 1990 (now abandoned); and is a CIP of (III) application Ser. No. 08/731,299, filed Oct. 4, 1996 now U.S. Pat. No. 6,078,785. The entire disclosures of each of these applications, which are assigned to the assignee of this application, are incorporated herein by reference.

FIELD OF THE INVENTION

This application is directed to oligonucleotides and oligonucleosides functionalized to include lipophilic moieties. Relative to their unfunctionalized parent compounds, such lipophilic oligonucleotide conjugates have improved biostability and altered biodistribution in mammals. In one embodiment, such lipophilic oligonucleotide conjugates are used in a method of targeting antisense oligonucleotides to hepatic tissues and thereby preferentially modulating gene expression in the liver and associated tissues of a mammal.

BACKGROUND OF THE INVENTION

Messenger RNA (mRNA) directs protein synthesis. Antisense methodology is the complementary hybridization of relatively short oligonucleotides to mRNA or DNA such that the normal, essential functions of these intracellular nucleic acids are disrupted. Hybridization is the sequence-specific hydrogen bonding via Watson-Crick base pairs of oligonucleotides to RNA or single-stranded DNA. Such base pairs are said to be complementary to one another.

The naturally occurring events that provide the disruption of the nucleic acid function, discussed by Cohen in *Oligonucleotides: Antisense Inhibitors of Gene Expression*, CRC Press, Inc., Boca Raton, Fla. (1989) are thought to be of two types. The first, hybridization arrest, denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides (Miller, et al., *Anti-Cancer Drug Design*, 1987, 2, 117) and α-anomer oligonucleotides are examples of antisense agents which are thought to disrupt nucleic acid function by hybridization arrest.

The second type of terminating event for antisense oligonucleotides involves the enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

Considerable research is being directed to the application of oligonucleotides and oligonucleotide analogs as antisense agents for diagnostics, research reagents and potential therapeutic purposes. At least for therapeutic purposes, and for research purposes involving whole cells, tissues or animals, the antisense oligonucleotides and oligonucleotide analogs must be transported across cell membranes or otherwise taken up by cells in order to exhibit activity. One method for generally increasing membrane or cellular transport is by the attachment of a pendant lipophilic group. More specifically, Ramirez et al. (*J. Am. Chem. Soc.*, 1982, 104, 5483) introduced the phospholipid group 5'-O-(1,2-di-O-myristoyl-sn-glycero-3-phosphoryl) into the dimer TpT independently at the 3' and 5' positions. Subsequently Shea et al. (*Nuc. Acids Res.*, 1990, 18, 3777) disclosed oligonucleotides having a 1,2-di-O-hexyldecyl-rac-glycerol group linked to a 5'-phosphate on the 5'-terminus of the oligonucleotide. Certain of the Shea et. al. authors also disclosed these and other compounds in patent application PCT/US90/01002. A further glucosyl phospholipid was disclosed by Guerra et al. (*Tetrahedron Letters*, 1987, 28, 3581).

In other work, a cholesteryl group was attached to the inter-nucleotide linkage between the first and second nucleotides (from the 3' terminus) of an oligonucleotide. This work is disclosed in U.S. Pat. No. 4,958,013 and further by Letsinger et al. (*Proc. Natl. Acad. Sci. USA*, 1989, 86, 6553). The aromatic intercalating agent anthraquinone was attached to the 2' position of a sugar fragment of an oligonucleotide as reported by Yamana et al. (*Bioconjugate Chem.*, 1990, 1, 319). The same researchers placed pyrene-1-methyl at the 2' position of a sugar (Yamana et. al., *Tetrahedron Lett.*, 1991, 32, 6347).

Lemaitre et al. (*Proc. Natl. Acad. Sci. USA*, 1986, 84, 648) and Leonetti et al. (*Bioconjugate Chem.*, 1990, 1, 149). The 3' terminus of the oligonucleotides each include a 3'-terminal ribose sugar moiety. The poly(L-lysine) was linked to the oligonucleotide via periodate oxidation of this terminal ribose followed by reduction and coupling through a N-morpholine ring. Oligonucleotide-poly(L-lysine) conjugates are described in European Patent application 87109348.0. In this instance the lysine residue was coupled to a 5' or 3' phosphate of the 5' or 3' terminal nucleotide of the oligonucleotide. A disulfide linkage has also been utilized at the 3' terminus of an oligonucleotide to link a peptide to the oligonucleotide (Corey et al., *Science*, 1987, 238, 1401; Zuckermann, et al., *J. Am. Chem. Soc.*, 1988, 110, 1614; and Corey et al., *J. Am. Chem. Soc.*, 1989, 111, 8524).

Nelson et al. (*Nuc. Acids Res.*, 1989, 17, 7187) describe a linking reagent for attaching biotin to the 3'-terminus of an oligonucleotide. This reagent, N-Fmoc-O-DMT-3-amino-1,2-propanediol is now commercially available from Clontech Laboratories (Palo Alto, Calif.) under the name 3'-Amine on. It is also commercially available under the name 3'-Amino-Modifier reagent from Glen Research Corporation (Sterling, Va.). This reagent was also utilized to link a peptide to an oligonucleotide as reported by Judy et al. (*Tetrahedron Letters,* 1991, 32, 879). A similar commercial reagent (actually a series of such linkers having various lengths of polymethylene connectors) for linking to the 5'-terminus of an oligonucleotide is 5'-Amino-Modifier C6. These reagents are available from Glen Research Corporation (Sterling, Va.). These compounds or similar ones were utilized by Krieg et al. (*Antisense Research and Development,* 1991, 1, 161) to link fluorescein to the 5'-terminus of an oligonucleotide. Other compounds of interest have also been linked to the 3'-terminus of an oligonucleotide. Asseline et al. (*Proc. Natl. Acad. Sci. USA,* 1984, 81, 3297) described linking acridine on the 3'-terminal phosphate group of an poly (Tp) oligonucleotide via a polymethylene linkage. Haralambidis et al. (*Tetrahedron Letters,* 1987, 28, 5199) report building a peptide on a solid state support and then linking an oligonucleotide to that peptide via the 3' hydroxyl group of the 3' terminal nucleotide of the oligonucleotide. Chollet (*Nucleosides & Nucleotides,* 1990, 9, 957) attached an Aminolink 2 (Applied Biosystems, Foster City, Calif.) to the 5' terminal phosphate of an oligonucleotide. Chollet then used the bifunctional linking group SMPB (Pierce Chemical Co., Rockford, Ill.) to link an interleukin protein to the oligonucleotide.

An EDTA iron complex has been linked to the 5 position of a pyrimidine nucleoside as reported by Dreyer et al. (*Proc. Natl. Acad. Sci. USA,* 1985, 82, 968). Fluorescein has been linked to an oligonucleotide in the same manner as reported by Haralambidis, et al. (*Nucleic Acid Research,* 1987, 15, 4857) and biotin in the same manner as described in PCT application PCT/US/02198. Fluorescein, biotin and pyrene were also linked in the same manner as reported by Telser et al. (*J. Am. Chem. Soc.,* 1989, 111, 6966). A commercial reagent, Amino-Modifier-dT, from Glen Research Corporation (Sterling, Va.) can be utilized to introduce pyrimidine nucleotides bearing similar linking groups into oligonucleotides.

Cholic acid linked to EDTA for use in radioscintigraphic imaging studies was reported by Betebenner et al. (*Bioconjugate Chem.,* 1991, 2, 117); however, it is not known to link cholic acid to nucleosides, nucleotides or oligonucleotides.

Despite these efforts and other research in the field, it is not known in the art to use lipophilic conjugation to alter the pharmacodynamic properties of an antisense compound, i.e., an agent that works via a nucleotide sequence-dependent antisense mechanism.

OBJECTS OF THE INVENTION

It is one object of this invention to provide oligonucleotides and oligonucleosides functionalized to include lipophilic moieties in order to produce lipophilic oligonucleotide and oligonucleoside conjugates which, relative to their unfunctionalized parent compounds, have improved biostability and altered biodistribution in mammals.

It is a further object of the invention to provide methods of modulating gene expression in cells, tissue(s) or organ(s) of a mammal using the lipophilic oligonucleotide and oligonucleoside conjugates of the invention.

It is a particular object of the invention to provide compositions for and methods of targeting antisense oligonucleotides to hepatic tissues and thereby preferentially modulating gene expression in the liver and associated tissues of a mammal.

BRIEF DESCRIPTION OF THE INVENTION

These and other objects are satisfied by the present invention, which provides oligonucleotides and oligonucleosides functionalized to include lipophilic moieties. In one aspect, the invention provides nucleosides having base portions and ribofuranosyl sugar portions. Such nucleosides bear at a 2'-O-position, a 3'-O-position, or a 5'-O-position a substituent having formula:

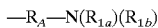

where:

$R_A$ is alkyl having from 1 to about 10 carbon atoms or $R_A$ is $(CH_2-CH_2-Q-)_x$;

$R_{1a}$ and $R_{1b}$, independently, are H, $R_A$, $R_2$, or an amine protecting group or have formula $C(X)-R_2$, $C(X)-R_A-R_2$, $C(X)-Q-R_A-R_2$, $C(X)-Q-R_2$;

$R_2$ includes a steroid molecule, a reporter molecule, a lipophilic molecule, a reporter enzyme, a peptide, a protein, or has formula $-Q-(CH_2CH_2-Q-)_x-R_3$;

X is O or S;

each Q is, independently, is NH, O, or S;

x is 1 to about 200;

$R_3$ is H, $R_A$, C(O)OH, C(O)$OR_A$, C(O)$R_4$, $R_A-N_3$, $R_A-NH_2$, or $R_A-SH$; and $R_4$ is Cl, Br, I, $SO_2R_5$ or has structure:

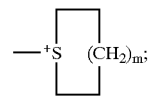

m is 2 to 7; and $R_5$ is alkyl having 1 to about 10 carbon atoms.

In another aspect, the invention provides oligonucleotides and oligonucleosides comprising a plurality of linked nucleosides, wherein each nucleoside includes a ribofuranosyl sugar portion and a base portion and at least one (preferably more than one) of the nucleosides bears at a 2'-O-position, a 3'-O-position, or a 5'-O-position a substituent having formula $-R_A-N(R_{1a})(R_{1b})$.

In another aspect the invention provides methods for preparing oligonucleotides and oligonucleosides comprising the steps of contacting nucleosides according to the invention for a time and under reaction conditions effective to form a covalent bond therebetween. In preferred embodiments, at least one of the nucleosides bears a phosphoramidate group at its 2'-O-position or at its 3'-O-position.

In other embodiments, compounds according to the invention are prepared by contacting a nucleoside, oligonucleotide or oligonucleoside with derivatizing reagents. For example, a nucleoside, oligonucleotide or oligonucleoside bearing a 2'-hydroxy group, a 3'-hydroxy group, or a 5'-hydroxy group under basic conditions with a compound having formula $L_1-R_A-N(R_{1a})(R_{1b})$ wherein $L_1$ is a leaving group such as a halogen and at least one of $R_{1a}$ and $R_{1b}$ is an amine protecting group.

The present invention also provides methods for inhibiting the expression of particular genes in the cells of an organism, comprising administering to said organism a compound according to the invention. Also provided are methods for inhibiting transcription and/or replication of particular genes or for inducing degradation of particular regions of double stranded DNA in cells of an organism by administering to said organism a compound of the invention. Further provided are methods for killing cells or virus by contacting said cells or virus with a compound of the invention. The compound can be included in a composition that further includes an inert carrier for the compound.

BRIEF DESCRIPTION OF THE DRAWINGS

The numerous objects and advantages of the present invention may be better understood by those skilled in the art by reference to the accompanying figures, in which.

DETAILED DESCRIPTION OF THE INVENTION

Figure 1:
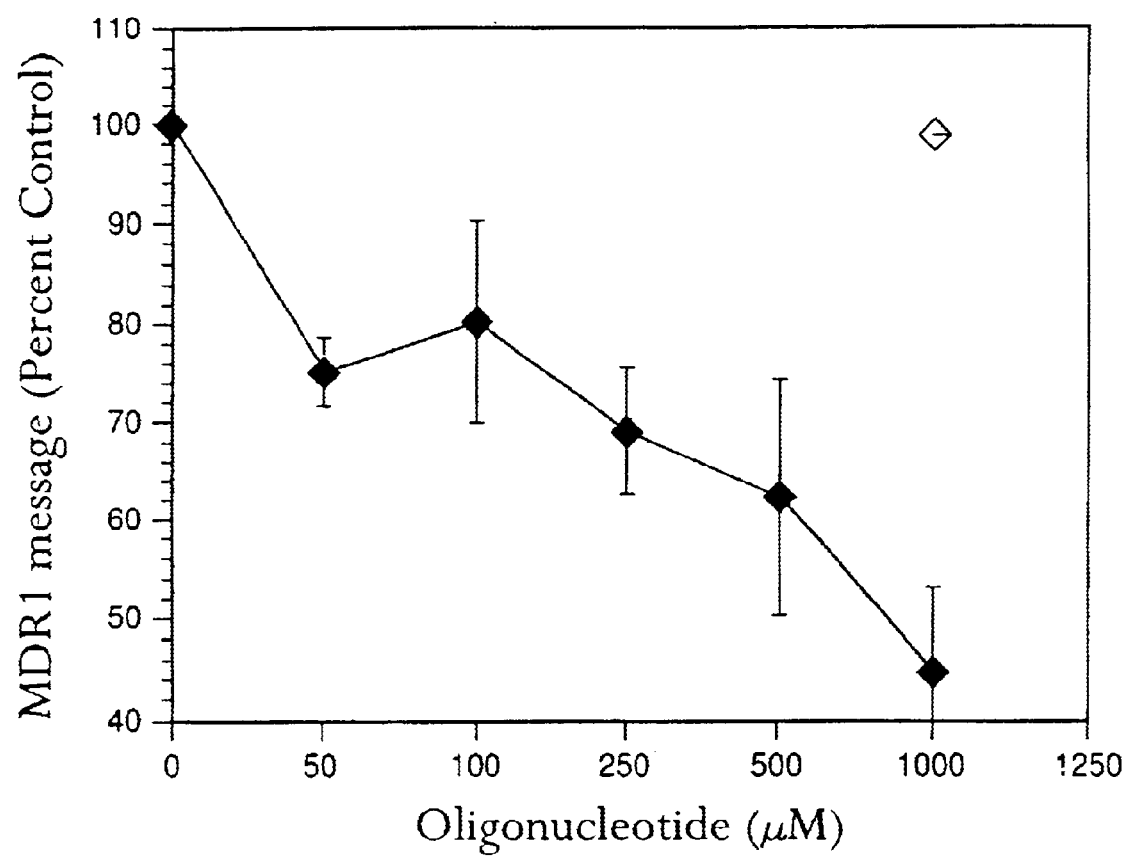
FIG. 1 shows the dose response for oligonucleotide inhibition of MDR1 message in transfected 3T3 cells. The MDR-3T3 cells were treated with 50 nM, 100 nM, 250 nM, 500 nM or 1000 nM concentrations of ISIS 5995 oligomer, or 1000 nM of ISIS 10221 scrambled control oligomer, for 24 hours in the presence of LIPOFECTIN$^R$. RNA was isolated, separated and probed with a 1.0 kB MDR1 cDNA fragment. The same blots were stripped and probed with a beta-actin probe to ensure uniform loading. Levels of MDR1 mRNA from the blots were quantitated using a PHOSPHO-RIMAGER™ (Molecular Dynamics, Sunnyvale, Calif.) and the values are expressed as percent of control. The results represent mean values and standard errors of the mean from 5 independent experiments. Filled diamond, ISIS 5995; closed diamond, ISIS 10221.

This invention provides nucleosides, oligonucleotides and oligonucleosides functionalized to include lipophilic moieties in order to produce lipophilic oligonucleotide and oligonucleoside conjugates which, relative to their unfunctionalized parent compounds, have improved biostability and altered biodistribution in mammals. The nucleoside subunits can be "natural" or "synthetic" moieties. Each nucleoside is formed from a naturally occurring or synthetic base and a naturally occurring or synthetic pentofuranosyl sugar group.

The term "oligonucleotide" refers to a polynucleotide formed from a plurality of linked nucleotide units. The nucleotide units each include a nucleoside unit. In the context of this invention, the term "oligonucleoside" refers to a plurality of nucleoside units that are linked together. In a generic sense, since each nucleotide unit of an oligonucleotide includes a nucleoside therein, the term "oligonucleoside" can be considered to be inclusive of oligonucleotides (i.e., nucleosides linked together via phosphate linking groups). In a further sense, the term "oligonucleoside" also refers to a plurality of nucleosides that are linked together via linkages other than phosphate linkages. The term "oligonucleoside" thus effectively includes naturally occurring species or synthetic species formed from naturally occurring subunits. For brevity, the term "oligonucleoside" will be used as encompassing both phosphate linked (oligonucleotides) and non-phosphate linked polynucleoside species.

Oligonucleosides according to the invention also can include modified subunits. Representative modifications include modification of a heterocyclic base portion of a nucleoside or a sugar portion of a nucleoside. Exemplary modifications are disclosed in the following U.S. patent applications: Ser. No. 07/835,932, filed Mar. 5, 1992, now U.S. Pat. No. 5,670,633, entitled Sugar Modified Oligonucleotides That Detect And Modulate Gene Expression; Ser. No. 558,663, filed Jul. 27, 1990, now U.S. Pat. No. 5,138,045, entitled Novel Polyamine Conjugated Oligonucleotides; Ser. No. 558,806, filed Jul. 27, 1991, entitled Nuclease Resistant Pyrimidine Modified Oligonucleotides that Detect and Modulate Gene Expression and Ser. No. PCT/US91/00243, filed Jan. 11, 1991, entitled Compositions and Methods for Detecting and Modulating RNA Activity. Teachings regarding the synthesis of particular modified oligonucleotides may also be found in the following U.S. patents or pending patent applications, each of which is commonly assigned with this application: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, issued Jun. 29, 1993, and 5,608,046, both drawn to conjugated 4'-desmethyl nucleoside analogs; U.S. Pat. Nos. 5,602,240, and 5,610,289, drawn to backbone modified oligonucleotide analogs; and U.S. patent application Ser. No. 08/383,666, filed Feb. 3, 1995, and U.S. Pat. No. 5,459,255, drawn to, inter alia, methods of synthesizing 2'-fluoro-oligonucleotides.

The term oligonucleoside thus refers to structures that include modified portions, be they modified sugar moieties or modified base moieties, that function similarly to natural bases and natural sugars. Representative modified bases include deaza or aza purines and pyrimidines used in place of natural purine and pyrimidine bases; pyrimidines having substituent groups at the 5 or 6 position; and purines having altered or replacement substituent groups at the 2, 6 or 8 positions. Representative modified sugars include carbocyclic or acyclic sugars, sugars having substituent groups at their 2' position, and sugars having substituents in place of one or more hydrogen atoms of the sugar. Other altered base moieties and altered sugar moieties are disclosed in U.S. Pat. No. 3,687,808 and PCT application PCT/US89/02323.

Altered base moieties or altered sugar moieties also include other modifications consistent with the spirit of this invention. Such oligonucleosides are best described as being structurally distinguishable from yet functionally interchangeable with naturally occurring or synthetic wild type oligonucleotides. All such oligonucleosides are comprehended by this invention so long as they function effectively to mimic the structure of a desired RNA or DNA strand.

For use in antisense methodology, the oligonucleosides of the invention preferably comprise from about 10 to about 30 subunits. It is more preferred that such oligonucleosides comprise from about 15 to about 25 subunits. As will be appreciated, a subunit is a base and sugar combination suitably bound to adjacent subunits through, for example, a phosphorus-containing (e.g., phosphodiester) linkage or some other linking moiety. The nucleosides need not be linked in any particular manner, so long as they are covalently bound. Exemplary linkages are those between the 3'- and 5'-positions or 2'- and 5'-positions of adjacent nucleosides. Exemplary linking moieties are disclosed in the following references: Beaucage, et al., *Tetrahedron*, 1992, 48, 2223 and references cited therein; and U.S. Patents and applications: Ser. No. 07/703,619, filed May 21, 1991 (now U.S. Pat. No. 5,378,825); Ser. No. 07/903,160, filed Jun. 24, 1992 (now U.S. Pat. No. 5,623,070); Ser. No. 039,979, filed Mar. 20, 1993 (currently pending as continuation application Ser. No. 08/317,289, filed Oct. 3, 1994); Ser. No. 08/039,846, filed Mar. 30, 1993 and Ser. No. 08/392,675 filed Feb. 23, 1995, (now U.S. Pat. No. 5,677,437; and Ser. No. 08/040,933, filed Mar. 31, 1993 (now U.S. Pat. No. 5,618, 704). Each of the foregoing Patents or applications is assigned to the assignee of this invention, and the disclosure of each is incorporated herein by reference.

It is preferred that the RNA or DNA portion which is to be modulated using oligonucleosides of the invention be preselected to comprise that portion of DNA or RNA which codes for the protein whose formation or activity is to be modulated. The targeting portion of the composition to be employed is, thus, selected to be complementary to the preselected portion of DNA or RNA, that is, to be an antisense oligonucleoside for that portion.

In accordance with one preferred embodiment of this invention, the compounds of the invention hybridize to mRNA encoding ICAM-1 (intercellular adhesion molecule 1). ICAM-1 is a cell surface glycoprotein expressed primarily in endothelial cells that binds other cells, such as neutrophils, expressing cell surface antigens such as LFA-1 (Kishimoto et al., *Adv. Immunol.*, 1989, 46, 149). Several lines of experimentation indicate that ICAM-1 plays an important role during various inflammatory responses (Bochner et al., *J. Exp. Med.*, 1991, 173, 1553; Carlos et al., *Blood*, 1991, 77, 2266). By modulating such responses according to the compositions and methods of the present invention, undesirable inflammatory responses are mediated. In another preferred embodiment of the invention, the compounds of the invention hybridize to MDR1 (multidrug resistance) mRNA encoding a membrane protein (P-glycoprotein) that functions as an ATP driven efflux pump. Hyperproliferative cells may become resistant to anticancer agents due to an overabundance of one or more nucleic acids (i.e., mRNA or DNA) encoding one or more such MDR proteins. By modulating this resistance according to the compositions and methods of the present invention, resistant cells are resensitized to such anticancer agents. Accordingly, the compositions and methods of the invention act to enhance the treatment of abnormal cell proliferation and tumor formation with anticancer agents. In further embodiments of the invention, the compounds of the invention hybridize to HIV mRNA encoding the tat protein, or to the TAR region of HIV mRNA. Other preferred compounds are complementary to sequences for herpes, papilloma and other viruses, or to sequences corresponding to cellular oncogenes, mediators of the immune response of an animal and other host-encoded functions.

The nucleosides and oligonucleosides of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated since they include both DNA-RNA transcription and RNA-protein translation as integral parts of their cellular activity. Many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides. As used herein, therapeutics is meant to include the eradication of a disease state, by killing an organism or by control of erratic or harmful cellular growth or expression. The invention is also drawn to the administration of biologically active oligonucleotides having biological activity to cultured cells, isolated tissues and organs and animals. By being "biologically active," it is meant that the oligonucleotide functions to modulate the expression of one or more genes in cultured cells, isolated tissues or organs and/or animals. Such modulation can be achieved by an antisense oligonucleotide by a variety of mechanisms known in the art, including but not limited to transcriptional arrest; effects on RNA processing (capping, polyadenylation and splicing) and transportation; enhancement of cellular degradation of the target nucleic acid; and translational arrest (Crooke et al., *Exp. Opin. Ther. Patens*, 1996, 6:855).

The formulation of therapeutic compositions and their subsequent administration is believed to be within the skill of those in the art. In general, for therapeutics, a patient in need of such therapy is administered an oligonucleotide in accordance with the invention, commonly in a pharmaceutically acceptable carrier, in doses ranging from 0.01 µg to 100 g per kg of body weight depending on the age of the patient and the severity of the disorder or disease state being treated. Further, the treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the oligonucleotide may either be increased in the event the patient does not respond significantly to current dosage levels, or the dose may be decreased if an alleviation of the symptoms of the disorder or disease state is observed, or if the disorder or disease state has been ablated.

In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years.

In one aspect, the present invention is directed to nucleosides and oligonucleosides that bear at least one amine-containing substituent at a position. Such substituents preferably have formula —$R_A$—$N(R_{1a})(R_{1b})$ and are appended at 2'-O-, 3'-O-, and/or 5'-O-positions.

Each $R_A$ according to the invention is an alkyl moiety independently selected to having 1 to about 10 carbon atoms or $R_A$ is a polyether, a polythioether or polyalkylamine. The term "alkyl" is intended to include straight chain and branched hydrocarbons. The preferred length of these hydrocarbons is 1 to about 7 carbon atoms.

$R_{1a}$ and $R_{1b}$ according to the invention are H, $R_A$, $R_2$, an amine protecting group, or have formula $C(X)$—$R_2$, $C(X)$—$R_A$—$R_2$, $C(X)$—Q—$R_A$—$R_2$, $C(X)$—Q—$R_2$. Protecting groups are known per se as chemical functional groups that can be selectively appended to and removed from functionalities, such as amine groups. These groups are present in a chemical compound to render such functionality inert to chemical reaction conditions to which the compound is exposed. See, e.g., Greene and Wuts, Protective Groups in Organic Synthesis, 2d edition, John Wiley & Sons, New York, 1991. Numerous amine protecting groups are known in the art, including, but not limited to: phthalimide (PHTH), trifluoroacetate (triflate), allyloxycarbonyl (Alloc), benzyloxycarbonyl (CBz), chlorobenzyloxycarbonyl, t-butyloxycarbonyl (Boc), fluorenylmethoxycarbonyl (Fmoc), and isonicotinyloxycarbonyl (i-Noc) groups. (see, e.g., Veber and Hirschmann, et al., *J. Org. Chem.*, 1977, 42, 3286 and Atherton, et al., The Peptides, Gross and Meienhofer, Eds, Academic Press; New York, 1983; Vol. 9 pp. 1–38).

$R_2$ can include a steroid molecule, a reporter molecule, a lipophilic molecule, a reporter enzyme, a peptide, a protein (i.e., a substituent consisting essentially of same), or a molecule having formula —Q—$(CH_2CH_2$—Q—$)_x$—$R_3$. For the purposes of this invention the terms "reporter molecule" and "reporter enzyme" are inclusive of those molecules or enzymes that have physical or chemical properties that allow them to be identified in gels, fluids, whole cellular systems, broken cellular systems and the like utilizing physical properties such as spectroscopy, radioactivity, colorimetric assays, fluorescence, and specific binding. Steroids include those chemical compounds that contain a perhydro-1,2-cyclopentanophenanthrene ring system. Proteins and peptides are utilized in their usual sense as polymers of amino acids. Normally peptides comprise such polymers that contain a smaller number of amino acids per unit molecule than do the proteins. Lipophilic molecules include naturally-occurring and synthetic aromatic and non-aromatic moieties such as fatty acids, esters, alcohols and other lipid molecules, substituted aromatic groups such as dinitrophenyl groups, cage structures such as adamantane and buckminsterfullerenes, and aromatic hydrocarbons such as benzene, perylene, phenanthrene, anthracene, naphthalene, pyrene, chrysene, and naphthacene.

Particularly useful as steroid molecules are the bile acids including cholic acid, deoxycholic acid and dehydrocholic acid; steroids including cortisone, digoxigenin, testosterone and cholesterol and even cationic steroids such as cortisone having a trimethylaminomethyl hydrazide group attached via a double bond at the 3 position of the cortisone rings. Particularly useful as reporter molecules are biotin, dinitrophenyl, and fluorescein dyes. Particularly useful as lipophilic molecules are alicyclic hydrocarbons, saturated and unsaturated fatty acids, waxes, terpenes and polyalicyclic hydrocarbons including adamantane and buckminsterfullerenes. Particularly useful as reporter enzymes are alkaline phosphatase and horseradish peroxidase. Particularly useful as peptides and proteins are sequence-specific peptides and proteins including phosphodiesterase, peroxidase, phosphatase and nuclease proteins. Such peptides and proteins include SV40 peptide, RNaseA, RNase H and Staphylococcal nuclease. Particularly useful as terpenoids are vitamin A, retinoic acid, retinal and dehydroretinol.

$R_2$ also can have formula —Q—$(CH_2CH_2$—Q—$)_x$—$R_3$, where Q is O, S, or NH. Subscript x can be 1 to about 200, preferably about 20 to about 150, more preferably about 10 to about 50. Preferably, Q are selected to be O, such that $R_2$ constitutes a poly(ethyleneglycol) (PEG) group (i.e., $R_3$=H) or a functionalized derivative thereof (e.g., $R_3$=C(O)Cl). $R_3$ can be H, $R_A$, C(O)OH, C(O)O$R_A$, C(O)$R_4$, $R_A$—$N_3$, $R_A$—$NH_2$ or $R_A$—SH where $R_4$ is F, Cl, Br, I, $SO_2R_5$ or a small thio-containing heterocycle having structure:

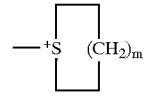

where m is 2 to 7. Representative PEG-containing $R_2$ groups are disclosed by Ouchi, et al., *Drug Design and Discovery*, 1992, 9, 93, Ravasio, et al., *J. Org. Chem.*, 1991, 56, 4329, and Delgardo et. al., *Critical Reviews in Therapeutic Drug Carrier Systems*, 1992, 9, 249.

Oligonucleosides according to the invention can be assembled in solution or through solid-phase reactions, for example, on a suitable DNA synthesizer utilizing nucleosides according to the invention and/or standard nucleotide precursors. The nucleosides and nucleotide precursors can already bear alkylamino groups or can be later modified to bear such groups.

In the former case, compounds according to the invention are prepared by, for example, reacting nucleosides bearing at least one free 2'-, 3'-, or 5'-hydroxyl group under basic conditions with a compound having formula $L_1$—$(CH_2)_n$—$N(R_{1a})(R_{1b})$ where $L_1$ is a leaving group and at least one of $R_{1a}$ and $R_{1b}$ is an amine protecting group. Displacement of the leaving group through nucleophilic attack of an oxygen anion produces the desired amine derivative. Leaving groups according to the invention include but are not limited to halogen, alkylsulfonyl, substituted alkylsulfonyl, arylsulfonyl, substituted arylsulfonyl, hetercyclcosulfonyl or trichloroacetimidate. A more preferred group includes chloro, fluoro, bromo, iodo, p-(2,4-dinitroanilino) benzenesulfonyl, benzenesulfonyl, methylsulfonyl (mesylate), p-methylbenzenesulfonyl (tosylate), p-bromobenzenesulfonyl, trifluoromethylsulfonyl (triflate), trichloroacetimidate, acyloxy, 2,2,2-trifluoroethanesulfonyl, imidazolesulfonyl, and 2,4,6-trichlorophenyl, with bromo being preferred.

Suitably protected nucleosides can be assembled into an oligonucleosides according to known techniques. See, e.g., Beaucage, et al., *Tetrahedron*, 1992, 48, 2223.

Oligonucleosides according to the invention also can be prepared by assembling an oligonucleoside and appending alkylamino functionality thereto. For example, oligonucleosides having free hydroxyl groups can be assembled according to known techniques and then reacted with a reagent having formula $L_1$—$(CH_2)_n$—$N(R_{1a})(R_{1b})$. As will be recognized, however, greater selectivity can be achieved in terms of placement of alkylamino functionality within an oligonucleoside by introducing such functionality, as discussed above, on selected nucleosides and then using both the selected nucleosides and other nucleosides to construct an oligonucleoside.

Once assembled, an oligonucleoside bearing one or more groups having formula —$R_A$—$N(R_{1a})(R_{1b})$ wherein at least one of $R_{1a}$ and $R_{1b}$ is a protecting group is treated with reagents effective to remove the protecting group. Once deprotected, the oligonucleoside can be contacted with electrophilic moieties such as, for example, succinimidyl esters and other activate carboxylic acids including C(=O)—O-succinimide and C(=O)—O-pentafluorophenyl, isothiocyanates, sulfonyl chlorides, halacetamides, phospholipid carbocyclic acid active esters, o-phenanthroline-5-iodoacetamide, fluorescein isothiocyanate, 1-pyrene butyric acid-N-hydroxy succinimide ester and carboxylic acid derivatives of PNA (carboxylic acid derivatives of peptide nucleic acids). Preferred electrophilic moieties include cholesteryl-3-hemisuccinate-N-hydroxy succinimide ester, pyrene-1-butyric acid-N-hydroxy succinimide ester and polyethylene glycol-propionic acid-N-hydroxy succimide ester.

Thus, the invention first builds the desired linked nucleoside sequence in the normal manner on the DNA synthesizer. One or more (preferably two or more) of the linked nucleosides are then functionalized or derivatized with the lipophilic steroid, reporter molecule, lipophilic molecule, reporter enzyme, peptide or protein.

The following Examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention. For example, those skilled in the art will appreciate that it is also possible to synthesize modified oligonucleotides appropriate for use in the methods of the invention, such as, for example, cholesterol-conjugated oligonucleotides, by using modified amidites that have become available subsequent to the earliest priority date of the present application to prepare commercially available modified amidites and controlled-pore glass (CPG) products such as those available from Glen Research (Sterling, Va.; see, for example, Agrawal, Chapter 3 In: *Methods in Molecular Biology, Vol. 26: Protocols for Oligonucleotide Conjugates*, Agrawal, ed., Humana Press Inc., Totowa, N.J. (1994) pages 93–120.

EXAMPLES

Example 1

Preparation of Oligonucleotides a having 2'-Protected-Amine Terminating Linking Group A. Preparation of 5'-Dimethoxytrityl-2'-(O-Pentyl-N-phthalimido)-2'-Deoxyadenosine Phosphoramidite.

To introduce a functionalization at the 2' position of nucleotides within desired oligonucleotide sequences, 5'-dimethoxytrityl-2'-(O-pentyl-N-phthalimido)-2'-deoxyadenosine phosphoramidite was utilized to provide a linking group attached to the 2' position of nucleotide components of an oligonucleotide. This compound was synthesized generally in accordance with the procedures of parent application Ser. Nos. US91/00243 and 07/463,358 starting from adenosine. Briefly, this procedure treats adenosine with NaH in dimethylformamide (DMF) followed by treatment with N-(5-bromopentyl)phthalimide. Further treatment with $(CH_3)_3SiCl$, Ph—C(O)—Cl and $NH_4OH$ yields N6-benzyl protected 2'-pentyl-N-phthalimido functionalized adenosine. Treatment with DIPA and $CH_2Cl_2$ adds a DMT blocking group at the 5' position. Finally phosphitylation gives the desired phosphoramidite compound. This compound was utilized in the DNA synthesizer as a 0.09M solution in anhydrous $CH_3CN$. Oligonucleotide synthesis was carried out in either an ABI 390B or an ABI 394 synthesizer employing the standard synthesis cycles with an extended coupling time of 10 minutes during coupling of Compound 2 into the oligonucleotide sequence. Coupling efficiency of greater than 98% was observed.

B. 2'-Protected-Amine Linking Group Containing Phosphodiester Oligonucleotides

The following oligonucleotides having phosphodiester inter-nucleotide linkages were synthesized (throughout the disclosure, unless otherwise indicated, all oligonucleotide sequences are listed in a standard 5' to 3' order from left to right):

Oligomer 9: 5'-TA*G-3';
Oligomer 10: 5'-CCA*G-3';
Oligomer 11: 5'-GGC-TGA*-CTG-CG-3' (SEQ ID NO:1);
Oligomer 12: 5'-CTG-TCT-CCA*-TCC-TCT-TCA-CT (SEQ ID NO:2);
Oligomer 13: 5'-CTG-TCT-CCA*-TCC-TCT-TCA*-CT (SEQ ID NO:2), wherein A* represents a nucleotide functionalized to incorporate a pentyl-N-phthalimido functionally. Oligomers 12 and 13 are antisense compounds to the E2 region of the bovine papilloma virus-1 (BPV-1). Oligomers 12 and 13 have the same sequence as Oligomer 3 in parent application Ser. No. 07/782,374, except for the 2' modification. The oligonucleotides were synthesized in either a 10 µmol scale or a 3×1 µmol scale in the "Trityl-On" mode. Standard deprotection conditions (30% $NH_4OH$, 55° C., 24 hours) were employed. The oligonucleotides were purified by reverse phase HPLC (Waters Delta-Pak $C_4$ 15 µm, 300A, 25×100 mm column equipped with a guard column of the same material). They were detritylated and further purified by size exclusion using a Sephadex G-25 column. NMR analyses by both proton and phosphorus NMR confirmed the expected structure for the Oligomers 9 and 10.

C. 2'-Protected-Amine Linking Group Containing Phosphorothioate Oligonucleotides The following oligonucleotides having phosphorothioate inter-nucleotide linkages were synthesized:

Oligomer 14: $T_sT_sG_s$-$C_sT_sT_s$-$C_sC_sA^*_s$-$T_sC_sT_s$-$T_sC_sC_s$-$T_sC_sG_s$-$T_sC$ (SEQ ID NO:3);

Oligomer 15: $T_sG_sG_s$-$G_sA_sG_s$-$C_sC_sA_s$-$T_sA_sG_s$-$C_sG_sA^*_s$-$G_sG_sC$ (SEQ ID NO:4); and Oligomer 16: $T_sG_sG_s$-$G_sA^*_sG_s$-$C_sC_sA^*_s$-$T_sA^*_sG_s$-$C_sG_sA^*_s$-$G_sG_sC$ (SEQ ID NO:4), wherein A* represents a nucleotide functionalized to incorporate a pentyl-N-phthalimido functionality and the subscript "s" represents a phosphorothioate inter-nucleotide backbone linkage. Oligomer 14 is an antisense compound directed to the E2 region of the bovine papilloma virus-1 (BPV-1). Oligomers 15 and 16 are antisense compounds to ICAM. Oligomer 14 has the same sequence as Oligomer 3 in parent application Ser. No. 07/782,374, except for the 2' modification whereas Oligomers 15 and 16 have the same sequence as Oligomer 4 in parent application Ser. No. 07/782,374 except for the 2' modification. These oligonucleotides were synthesized as per the method of Example 1(B) except during the synthesis, for oxidation of the phosphite moieties, the Beaucage reagent (i.e., 3H-1,2-benzodithioate-3-one, 1,1-dioxide; Radhakrishnan et al., *J. Am. Chem. Soc.,* 1990, 112, 1253) was used as a 0.24 M solution in anhydrous $CH_3CN$ solvent. The oligonucleotides were synthesized in the "Trityl-On" mode and purified by reverse phase HPLC utilizing the purification procedure of Example 1(B).

D. 2'-O-Methyl Derivatized, 2'-Protected-Amine Linking Group Containing RNA Oligonucleotides The following oligonucleotides having 2'-O-methyl groups on each nucleotide not functionalized with a 2'-protected amine functionalization were synthesized:

Oligomer 17: 5'-CCA-A*GC-CUC-AGA (SEQ ID NO:24), and

Oligomer 18: 5'-CCA-GGC-UCA-GA*T (SEQ ID NO:25), wherein A* represents a nucleotide functionalized to incorporate a pentyl-N-phthalimido functionality and where the remaining nucleotides except the 3'-terminus nucleotide are each 2'-O-methyl derivatized nucleotides. The 3'-terminus nucleotide in both Oligomers 17 and 18 is a 2'-deoxy nucleotide. Both Oligomers 17 and 18 are antisense compounds to the HIV-1 TAR region. The oligonucleotides were synthesized as per the method of Example 6 in parent application Ser. No. 07/782,374 (utilizing Compound 2 thereof) for introduction of the nucleotides containing the pentyl-N-phthalimido functionality and appropriate 2-O-methyl phosphoramidite nucleotides from Chemgenes Inc. (Needham, Mass.) for the remaining RNA nucleotides. The 3'-terminus terminal 2'-deoxy nucleotides were standard phosphoamidites utilized for the DNA synthesizer. The oligonucleotides were deprotected and purified as per the method of Example 1(B).

Example 2

Functionalization of Oligonucleotides at the 2' Position

A. Functionalization with Biotin

1. Single Site Modification

About 10 O.D. units ($A_{260}$) of Oligomer 12 (approximately 60 nmols based on the calculated extinction coefficient of $1.6756 \times 10^5$) was dried in a microfuge tube. The oligonucleotide was dissolved in 200 µl of 0.2 M $NaHCO_3$ buffer and D-biotin-N-hydroxysuccinimide ester (2.5 mg, 7.3 µmols) (Sigma, St. Louis, Mo.) was added followed by 40 µl DMF. The solution was let stand overnight. The solution was applied to a Sephadex G-25 column (0.7×15 cm) and the oligonucleotide fractions were combined. Analytical HPLC showed nearly 85% conversion to the product. The product was purified by HPLC (Waters 600E with 991 detector, Hamilton PRP-1 column 0.7×15 cm; solvent A: 50 mM TEAA pH 7.0; B: 45 mM TEAA with 80% acetonitrile: 1.5 ml flow rate: Gradient: 5% B for first 5 minutes, linear (1%) increase in B every minute thereafter) and further desalted on Sephadex G-25 to give the oligonucleotide:

Oligomer 19: 5'-CTG-TCT-CCA*-TCC-TCT-TCA-CT (SEQ ID NO:2), wherein A* represents a nucleotide functionalized to incorporate a biotin functionality linked via a 2'-O-pentyl-amino linking group to the 2' position of the designated nucleotide. HPLC retention times are shown in Table 1 below.

2. Multiple Site Modification

About 10 O.D. units ($A_{260}$) of Oligomer 13 (approximately 60 nmols) was treated utilizing the method of Example 8(A)(1) in parent application Ser. No. 07/782,374 with D-biotin-N-hydroxysuccinimide ester (5 mg) in 300 µl of 0.2 M $NaHCO_3$ buffer/50 µl DMF. Analytical HPLC showed 65% of double labeled oligonucleotide product and 30% of single labeled products (from the two available reactive sites). HPLC and Sephadex G-25 purification gave the oligonucleotide:

Oligomer 20: 5'-CTG-TCT-CCA*-TCC-TCT-TCA*-CT (SEQ ID NO:2), wherein A* represents nucleotides functionalized to incorporate a biotin functionality linked via a 2'-O-pentyl-amino linking group to the 2' position of the designated nucleotide. HPLC retention times for this product (and its accompanying singly labeled products) are shown in Table 1 below.

B. Functionalization with Fluorescein

1. Single Site Modification

A 1M $Na_2CO_3$/1M $NaHCO_3$ buffer (pH 9.0) was prepared by adding 1M $NaHCO_3$ to 1 M $Na_2CO_3$. A 200 µl portion of this buffer was added to 10 O.D. units of Oligomer 12 in a microfuge tube. A 10 mg portion of fluorescein-isocyanate in 500 µl DMF was added to give a 0.05 M solution. A 100 µl portion of the fluorescein solution was added to the oligonucleotide solution in the microfuge tube. The tube was covered with aluminum foil and let stand overnight. The reaction mixture was applied to a Sephadex G-25 column (0.7×20 cm) that had been equilibrated with 25% (v/v) ethyl alcohol in water. The column was eluted with the same solvent. Product migration could be seen as a yellow band well separated from dark yellow band of the excess fluorescein reagent. The fractions showing absorption at 260 nm and 485 nm were combined and purified by HPLC as per the purification procedure of Example 2(A)(1). Analytical HPLC indicated 81% of the desired doubly functionalized oligonucleotide. The product was lyophilized and desalted on Sephadex to give the oligonucleotide:

Oligomer 21: 5'-CTG-TCT-CCA*-TCC-TCT-TCA-CT (SEQ ID NO:2), wherein A* represents a nucleotide functionalized to incorporate a fluorescein functionality linked via a 2'-O-pentylamino linking group to the 2' position of the designated nucleotide. HPLC retention times are shown in Table 1 below.

2. Multiple Site Modification

A 10 O.D. unit ($A_{260}$) portion of Oligomer 13 (from Example 1) was dissolved in 300 μl of the 1M $Na_2HCO_3$/1M $Na_2CO_2$ buffer of Example 2(B)(1) and 200 μl of the fluorescein-isothiocyanate stock solution of Example 2(B)(1) was added. The resulting solution was treated as per Example 2(B)(1). Analytical HPLC indicated 61% of doubly labeled product and 38% of singly labeled products. Work up of the reaction gave the oligonucleotide:

Oligomer 22: 5'-CTG-TCT-CCA*-TCC-TCT-TCA*-CT (SEQ ID NO:2), wherein A* represents nucleotides functionalized to incorporate a fluorescein functionality linked via a 2'-O-pentyl-amino linking group to the 2' position of the designated nucleotide. HPLC retention times are shown in Table 1 below.

C. Functionalization with Cholic Acid

1. Single Site Modification

A 10 O.D. unit ($A_{260}$) portion of Oligomer 12 was treated with cholic acid-NHS ester (Compound 1 in parent application Ser. No. 07/782,374, 5 mg, 9.9 μmols) in 200 μl of 0.2 M $NaHCO_3$ buffer/40 μl DMF. The reaction mixture was heated for 16 hours at 45° C. The product was isolated as per the method of Example 2(B)(1). Analytical HPLC indicated greater than 85% product formation. Work up of the reaction gave the oligonucleotide:

Oligomer 23: 5'-CTG-TCT-CCA*-TCC-TCT-TCA-CT (SEQ ID NO:2), wherein A* represents a nucleotide functionalized to incorporate a cholic acid functionality linked via a 2'-O-pentyl-amino linking group to the 2' position of the designated nucleotide. HPLC retention times are shown in Table 1 below.

2. Multiple Site Modification

A 10 O.D. unit ($A_{260}$) portion of Oligomer 13 (see, Example 1) was treated with cholic acid-NHS ester (Compound 1 in application Ser. No. 782,374, 10 mg, 19.8 μmols) in 300 μl of 0.2 M $NaHCO_3$ buffer/50 μl DMF. The reaction mixture was heated for 16 hours at 45° C. The product was isolated as per the method of Example 2(A)(1). Analytical HPLC revealed 58% doubly labeled product, 17% of a first singly labeled product and 24% of a second singly labeled product. Work up as per Example 2(A)(1) gave the oligonucleotide:

Oligomer 24: 5'-CTG-TCT-CCA*-TCC-TCT-TCA*-CT (SEQ ID NO:2), wherein A* represents nucleotides functionalized to incorporate a cholic acid functionality linked via a 2'-O-pentyl-amino linking group to the 2' position of the designated nucleotide. HPLC retention times are shown in Table 1 below.

D. Functionalization with Digoxigenin

1. Single Site Modification

A 10 O.D. unit ($A_{260}$) portion of Oligomer 12 (see, Example 1) was treated with digoxigenin-3-O-methylcarbonyl-ε-aminocaproic N-hydroxy succinimide ester (Boehringer Mannheim Corporation, Indianapolis, Ind.) in 200 μl of 0.1 M borate pH 8.3 buffer/40 μl DMF. The reaction mixture was let stand overnight. The product was isolated as per the method of Example 2(A)(1). Work up of the reaction gave oligonucleotide:

Oligomer 25: 5'-CTG-TCT-CCA*-TCC-TCT-TCA-CT (SEQ ID NO:2), wherein A* represents nucleotide functionalized to incorporate a digoxigenin functionality linked via a 2'-O-pentyl-amino linking group to the 2' position of the designated nucleotide. HPLC retention times are shown in Table 1 below.

2. Multiple Site Modification

A 10 O.D. unit ($A_{260}$) portion of Oligomer 13 (see, Example 1) was treated with digoxigenin-3-O-methylcarbonyl-ε-aminocaproic N-hydroxy succinimide ester (Boehringer Mannheim Corporation, Indianapolis, Ind.) in 300 μl of 0.1 M borate pH 8.3 buffer/50 μl DMF. The reaction mixture was let stand overnight. The product was isolated as per the method of Example 2(A)(1). Work up as per Example 2(A)(1) gave the oligonucleotide:

Oligomer 26: 5'-CTG-TCT-CCA*-TCC-TCT-TCA*-CT (SEQ ID NO:2), wherein A* represents nucleotides functionalized to incorporate a cholic acid functionality linked via a 2'-O-pentyl-amino linking group to the 2' position of the designated nucleotide. HPLC retention times are shown in Table 1 below.

TABLE 1

HPLC RETENTION TIMES OF OLIGONUCLEOTIDES FUNCTIONALIZED AT THE 2' POSITION

| | Retention Time (Minutes) | | |
|---|---|---|---|
| Oligomer | Mono Substitution | Multiple | Substitution |
| Oligomer 12[1] | 21.78 | | |
| Oligomer 13[1] | | 22.50 | |
| Oligomer 19[2] | 23.58 | | |
| Oligomer 20[2] | | 24.16[a] | 25.19[b] |
| Oligomer 21[3] | 26.65 | | |
| Oligomer 22[3] | | 26.99[a] | 29.33[b] |
| | | 27.55[a] | |
| Oligomer 23[4] | 30.10 | | |
| Oligomer 24[4] | | 30.38[a] | 37.00[b] |
| | | 32.22[a] | |
| Oligomer 25[5] | 28.06 | | |
| Oligomer 26[5] | | 28.14[a] | 33.32[b] |
| | | 29.24[a] | |

Conditions: Waters 600E with 991 detector, Hamilton PRP-1 column 0.7 × 15 cm; solvent A: 50 mM TEAA pM 7.0; B: 45 mM TEAA with 80% acetonitrile: 1.5 ml flow rate: Gradient: 5% B for first 5 minutes, linear (1%) increase in B every minute thereafter;
a Mono conjugated minor product;
b Doubly conjugated major product;
1 Parent oligonucleotide - no 2' functionalization;
2 2' Biotin functionalization;
3 2' Fluorescein functionalization;
4 2'Cholic Acid functionalization; and
5 2'Digoxigenin functionalization.

Example 3

Characterization of Functionalized Oligonucleotides
PROCEDURE A: Confirmation of Structure of Functionalized Oligonucleotides Containing a Tethered 2'-Amino Moiety Oligonucleotides of the invention were digested with snake venom phosphodiesterase and calf-intestine alkaline phosphatase to their individual nucleosides. After digestion, the nucleoside composition was analyzed by HPLC. The HPLC analysis established that functionalized nucleotide compounds having the tethered 2'-amino moiety thereon were correctly incorporated into the oligonucleotide.

Snake venom phosphodiesterase [Boehringer-Mannheim cat. #108260, 1 mg (1.5 units)/0.5 ml] and alkaline phosphatase from calf intestine (1 unit/microliter, Boehringer-Mannhein cat. #713023) in Tris-HCl buffer (pH 7.2, 50 mM) were used to digest the oligonucleotides to their component nucleosides. To 0.5 O.D. Units of oligonucleotide in 50 μl buffer (nearly 40 μM final concentration for a 20 mer) was added 5 μl of snake venom phosphodiesterase (nearly 0.3 units/mL, final concentration) and 10 μl of alkaline phosphatase (app. 150 units/mL, final concentration). The reaction mixture was incubated at 37° C. for 3 hours. Following incubation, the reaction mixture was analyzed by HPLC using a reverse phase analytical column (app. 30×2.5 cm); solvent A: 50 mM TEAA pH 7; solvent B: acetonitrile; gradient 100% for 10 minutes, then 5% B for 15 minutes, then 10% B and then wash. The results of these digestion are shown in Table 2 for representative oligonucleotides.

TABLE 2

OLIGONUCLEOTIDE ANALYSIS VIA ENZYMATIC DIGESTION

| | Observed Ratios** | | | | |
|---|---|---|---|---|---|
| Oligomer | Abs. max. 267 C | 252 G | 267 T | 260 A* | A |
| Oligomer 10 | 2 | 1 | | 1 | |
| Oligomer 11 | 3 | 5 | 2 | 1 | |
| Oligomer 12 | 9 | 1 | 8 | 1 | 1 |
| Oligomer 13 | 9 | 1 | 8 | 2 | |

*Nucleotide having 2'-O-linker attached thereto; and
**Corrected to whole numbers.

As is evident from comparing the results in Table 2 to the Oligomer structures (see, Example 1), the correct nucleoside ratios are observed for the component nucleotides of the test oligonucleotides.

PROCEDURE B: Determination of Melting Temperatures (Tm's) of Cholic Acid Oligonucleotide Conjugates The relative ability of oligonucleotides to bind to their complementary strand is compared by determining the melting temperature of the hybridization complex of the oligonucleotide and its complementary strand. The melting temperature (Tm), a characteristic physical property of double helices, denotes the temperature in degrees centigrade at which 50% helical versus coil (un-hybridized) forms are present. Tm is measured by using the UV spectrum to determine the formation and breakdown (melting) of hybridization. Base stacking, which occurs during hybridization, is accompanied by a reduction in UV absorption (hypochromicity). Consequently, a reduction in UV absorption indicates a higher $T_m$. The higher the Tm, the greater the strength of the binding of the strands. Non-Watson-Crick base pairing has a strong destabilizing effect on the Tm. Consequently, absolute fidelity of base pairing is necessary to have optimal binding of an antisense oligonucleotide to its targeted RNA.

1. Terminal End Conjugates a. Synthesis

A series of oligonucleotides were synthesized utilizing standard synthetic procedures (for unfunctionalized oligonucleotides) or the procedure of Example 3(A) in parent application Ser. No. 07/782,374 for oligonucleotides having a 5'-terminus amino linker bearing oligonucleotide or the procedure of Example 3(B) in patent application Ser. No. 07/782,374 for 5'-terminus cholic acid-bearing oligonucleotides. Each of the oligonucleotides had the following 5-LO antisense sequence: 5'-TCC-AGG-TGT-CCG-CAT-C-3' (SEQ ID NO:6). The nucleotides were synthesized on a 1.0 μmol scale. Oligomer 32 was the parent compound having normal phosphodiester inter-nucleotide linkages. Oligomer 33 incorporated phosphorothioate inter-nucleotide linkages in the basic oligonucleotide sequence. Oligomer 34 is an intermediate oligonucleotide having a 5'-aminolink at the 5'-terminus of the basic oligonucleotide sequence and Oligomer 35 was a similar 5'-aminolink compound incorporating phosphorothioate inter-nucleotide linkages. Oligomer 36 is a 5'-terminus cholic acid conjugate of the basic phosphodiester oligonucleotide sequence while Oligomer 37 is a similar 5'-cholic acid conjugate incorporating phosphorothioate inter-nucleotide linkages. Oligomers 32 and 33 were synthetized in a "Trityl-On" mode and were purified by HPLC. Oligomers 34 and 35 were synthesized as per Example 3(A) in parent application Ser. No. 07/782,374 without or with Beaucage reagent treatment, to yield phosphodiester or phosphorothioate inter-nucleotide linkages, respectively. Oligomers 36 and 37 were prepared from samples of Oligomers 34 and 35, respectively, utilizing a solution of cholic acid N-hydroxysuccinimide ester (Compound 1) 1 dissolved in DMF as per Example 3(B) in parent application Ser. No. 07/782,374. Oligomers 36 and 37 were purified by HPLC. The products were concentrated and desalted in a Sephadex G-25 column. Gel electrophoresis analyses also confirmed a pure product with the pure conjugate moving slower than the parent oligonucleotide or 5'-amino functionalized oligonucleotide.

b. Melting Analysis

The test oligonucleotides (either the phosphodiester, phosphorothioate, cholic acid conjugated phosphodiester, cholic acid conjugated phosphorothioate or 5'-aminolink intermediate phosphodiester or phosphorothioate oligonucleotides of the invention or otherwise) and either the complementary DNA or RNA oligonucleotides were incubated at a standard concentration of 4 μM for each oligonucleotide in buffer (100 mM NaCl, 10 mM Na-phospate, pH 7.0, 0.1 mM EDTA). Samples were heated to 90 degrees C and the initial absorbance taken using a Guilford Response II sepctro-photometer (Corning, Inc., Corning, N.Y.). Samples were then slowly cooled to 15° C. and then the change in absorbance at 260 nm was monitored during the heat denaturation procedure. The temperature was elevated 1 degree/absorbance reading and the denaturation profile analyzed by taking the 1st derivative of the melting curve. Data was also analyzed using a two-state linear regression analysis to determine the Tm's. The results of these tests are shown in Table 3 as are the HPLC retention times of certain of the test compounds.

TABLE 3

MELTING TEMPERATURE OF THE HYBRIDIZATION COMPLEX
OF THE OLIGONUCLEOTIDE AND ITS COMPLEMENTARY
STRAND

| | Tm** | | HPLC Ter. Time* |
|---|---|---|---|
| Oligomer No. | DNA | RNA | (min.) |
| 32 | 62.6 | 62.0 | — |
| 33 | 55.4 | 54.9 | — |
| 34 | ND | ND | 13.6 |
| 35 | ND | ND | 17.0 |

TABLE 3-continued

MELTING TEMPERATURE OF THE HYBRIDIZATION COMPLEX
OF THE OLIGONUCLEOTIDE AND ITS COMPLEMENTARY
STRAND

| Oligomer No. | Tm** | | HPLC Ter. Time* (min.) |
|---|---|---|---|
| | DNA | RNA | |
| 36 | 63.4 | 62.4 | 22.0 |
| 37 | 56.3 | 55.8 | 22.5 |

*HPLC conditions: Walters Delta Pak C-18 RP 2.5u column, at 0 min 100% 0.1 TEAA; at 30 min 50% TEAA and 50% Acetonitrile: Flow rate 1.0 ml/min.
**Tm at 4 μM each strand from fit of duplicate melting curves to 2-state model with linear sloping base line. Conditions: 100 mM NaCl, 10 mM Phosphate, 0.1 mM EDTA, pH 7.0.
ND = not determined As is evident from the data presented in Table 3, conjugation of cholic acid at the end of the oligonucleotides does not affect the Tm of the oligonucleotides.

2. Strands Incorporating 2'-O-Pentylamino Linker a. Synthesis

An oligonucleotide of the sequence GGA*-CCG-GA*A*-GGT-A*CG-A*G (Oligomer 38, SEQ ID NO:7), wherein A* represents a nucleotide functionalized to incorporate a pentylamino functionality at its 2'-position was synthesized in a one micromole scale utilizing the method of Example 1(B). The oligonucleotide was purified by reverse phase HPLC, detritylated and desalted on Sephadex G-25. PAGE gel analysis showed a single band. A further oligonucleotide, Oligomer 39, having the same sequence but without any 2'-O-amino linker was synthesis in a standard manner. A complementary DNA oligonucleotide of the sequence 5'-CCT-GGC-CTT-CCA-TGC-TC (Oligomer 40, SEQ ID NO:8) was also synthesized in a standard manner as was a complementary RNA oligonucleotide of the sequence 5'-CCU-GGC-CUU-CCA-UGC-UC (Oligomer 41, SEQ ID NO:9).

b. Melting Analysis

Melting analysis was conducted as per the method of Procedure B(1) b. The results are shown in Table 4.

TABLE 4

MELTING TEMPERATURE OF THE HYBRIDIZATION COMPLEX
OF THE OLIGONUCLEOTIDE AND ITS COMPLEMENTARY STRAND

| Oligomer No. | Tm* | |
|---|---|---|
| | DNA[1] | RNA[2] |
| 38 | 54.5 | 58.0 |
| 39 | 60.6 | 56.9 |
| ($\Delta_{38-39}$) | (6.1) | (1.1) |

*Tm at 4 μM each strand from fit of duplicate melting curves to 2-state model with linear sloping base line;Conditions: 100 mM NaCl, 10 mM Phosphate, 0.1 mM EDTA, pH 7.0.
[1]Against DNA complementary strand, oligomer 40.
[2]Against RNA complementary strand, oligomer 41

As is evident from Table 4, against the RNA complementary strand the change in Tm's between the strand having 2'-amino linkers thereon and the unmodified strand is 1.1 degrees (0.22 change per modification). Against the DNA strand, the change is −6.1 degrees (−1.2 change per modification). When compared to the parent unmodified oligonucleotide the 2'-amino linker-containing strand has a stabilizing effect upon hybridization with RNA and a destabilizing effect upon hybridization with DNA.

Compounds of the invention were tested for their ability to increase cellular uptake. This was determined by judging either their ability to inhibit the expression of bovine papilloma virus-1 (BPV-1) or an assay involving luciferase production (for HIV-1).

PROCEDURE C: Determination of Cellular Uptake Judged by the Inhibition of Expression of Bovine Papilloma Virus-1 (bpv-1) as Measured by an E2 Transactivation Assay For this test, a phosphorothioate oligonucleotide analog of the sequence 5'-CTG-TCT-CCA-TCC-TCT-TCA-CT (Oligomer 42, SEQ ID NO:2) was used as the basic sequence. This sequence is designed to be complementary to the translation initiation region of the E2 gene of bovine papilloma virus type 1 (BPV-1). Oligomer 42 served as the positive control and standard for the assay. Oligomer 3 (from Example 4 in parent application Ser. No. 07/782,374) served as a second test compound. It has the same nucleobase sequence as Oligomer 42 but is a phosphorothioate oligonucleotide and, further, has a cholic acid moiety conjugated at the 3'-end of the oligonucleotide. Oligomer 2 (from Example 2 in parent application Ser. No. 07/782,374) served as a third test compound. It is also of the same sequence and is a phosphorothioate oligonucleotide, but has a cholic acid moiety conjugated at the 5'-end. Oligomer 5 (from Example 5 in parent application Ser. No. 07/782,374) served as a fourth test compound. It also has the same nucleobase sequence and is a phosphorothioate oligonucleotide but has cholic acid moiety conjugated at both the 3'- and 5'-ends. Compounds five, six and seven served as negative controls for the assay. The fifth test compound was a phosphorothioate oligonucleotide with no significant sequence homology with BPV-1. A sixth test compound was a further phosphorothioate oligonucleotide with no significant sequence homology with BPV-1. The seventh test compound, was a phosphorothioate oligonucleotide with cholic acid conjugated to the 3'-end but having no significant sequence homology with BPV-1.

For each test I-38 cells were plated at $5 \times 10^4$ cells per cm$^2$ in 60 mm petri dishes. Eight hours after plating, medium was aspirated and replaced with medium containing the test oligonucleotide and incubated overnight. Following incubation, medium was aspirated and replaced with fresh medium without oligonucleotide and incubated for one hour. Cells were then transfected by the CaPO$_4$ method with 2 μg of pE2RE-1-CAT. After a four hour incubation period cells were glycerol shocked (15% glycerol) for 1 minute followed by washing 2 times with PBS. Medium was replaced with DMEM containing oligonucleotide at the original concentration. Cells were incubated for 48 hours and harvested. Cell lysates were analyzed for chloramphenicol acetyl transferase by standard procedures. Acetylated and nonacetylated $^{14}$C-chloramphenicol were separated by thin layer chromatography and quantitated by liquid scintillation. The results are expressed as percent acetylation.

Two lots of the positive control compound were found to acetylate at a level of 29% and 30%. The negative controls, test compounds five, six and seven, were found to acetylate at 59%, 58% and 47%, respectively. The 3'-cholic acid conjugate test compound, Oligomer 3, was found to acetylate to 23%, the 5'-cholic acid conjugate test compound, Oligomer 2, was found to acetylate to 36% and the test compound conjugated at both the 3'-end and the 5'-end, Oligomer 5, was found to acetylate to 27%.

The results of this test suggests that placement of a cholic acid moiety at the 3'-terminus of an oligonucleotide increase the activity. This in turn suggests that the increased activity was the result of increased cellular membrane transport.

PROCEDURE D: Determination of Cellular Uptake Judged by Inhibition of pHIVluc with Cholic Acid Linked 2'-O-Methyl Substituted Oligonucleotides For this test the absence of an oligonucleotide in a test well served as the control. All oligonucleotides were tested as 2'-O-methyl analogs. For this test an oligonucleotide of the sequence 5'-CCC-AGG-CUC-AGA (Oligomer 43, SEQ ID NO:10), where each of the nucleotides of the oligonucleotide includes a 2'-O-methyl substituent group served as the basic test compound. The second test compound of the sequence 5'-CHA-CCC-AGG-CUC-AGA (Oligomer 44, SEQ ID NO:10), wherein CHA represents cholic acid and where each of the nucleotides of the oligonucleotide includes a 2'-O-methyl substituent group, was also of the same sequence as the first test compound. This second test compound included cholic acid conjugated to its 5'-end and was prepared as per the method of Example 3 in parent application Ser. No. 07/782,374 utilizing 2'-O-methyl phosphoramidite intermediates as identified in Example 1(C). The third test compound of the sequence 5'-CCC-AGG-CUC-AGA-3'-CHA (Oligomer 45, SEQ ID NO:10), wherein CHA represents cholic acid and where each of the nucleotides of the oligonucleotide includes a 2'-O-methyl substituent group was also of the same sequence as the first test compound. The third test compound included cholic acid conjugated to its 3'-end and was prepared as per the method of Example 4 in parent application Ser. No. 07/782,374 utilizing 2'-O-methyl phosphoramidite intermediates as identified in Example 1(C). The fourth test compound was a 2'-O-Me oligonucleotide of a second sequence 5'-GAG-CUC-CCA-GGC (Oligomer 46, SEQ ID NO:11), where each of the nucleotides of the oligonucleotide includes a 2'-O-methyl substituent group. The fifth test compound was of sequence 5'-CHA-GAG-CUC-CCA-GGC (Oligomer 47, SEQ ID NO:11), wherein CHA represents cholic acid and where each of the nucleotides of the oligonucleotide includes a 2'-O-methyl substituent group. It was of the same sequence as the fifth test compound. This test compound included cholic acid conjugated to its 5'-end and was prepared as per the method of Example 3 in parent application Ser. No. 07/782,374 utilizing 2'-O-methyl phosphoramidite intermediates as identified in Example 1(C).

A sixth test compound was a randomized oligonucleotide of the sequence 5'-CAU-GCU-GCA-GCC (Oligomer 48, SEQ ID NO:12).

HeLa cells were seeded at $4 \times 10^5$ cells per well in 6-well culture dishes. Test oligonucleotides were added to triplicate wells at 1 μmM and allowed to incubate at 37° C. for 20 hours. Medium and oligonucleotide were then removed, cells washed with PBS and the cells were $CaPO_4$ transfected. Briefly, 5 μg of pHIVluc, a plasmid expressing the luciferase cDNA under the transcriptional control of the HIV LTR constructed by ligating the KpnI/HindIII restriction fragments of the plasmids pT3/T7luc and pHIVpap (NAR 19(12)) containing the luciferase cDNA and the HIV LTR respectively, and 6 μg of pcDEBtat, a plasmid expressing the HIV tat protein under the control of the SV40 promoter, were added to 500 μl of 250 mM $CaCl_2$, then 500 μl of 2xHBS was added followed by vortexing. After 30 minutes, the $CaPO_4$ precipitate was divided evenly between the six wells of the plate, which was then incubated for 4 hours. The media and precipitate were then removed, the cells washed with PBS, and fresh oligonucleotide and media were added. Incubation was continued overnight. Luciferase activity was determined for each well the following morning. Media was removed, then the cells washed 2x with PBS. The cells were then lysed on the plate with 200 μl of LB (1% Trit X-100, 25 mM Glycylglycine pH 7.8, 15 mM $MgSO_4$, 4 mM EGTA, 1 mM DTT). A 75 μl aliquot from each well was then added to a well of a 96 well plate along with 75 μl of assay buffer (25 mM Glycylglycine pH 7.8, 15 mM $MgSO_4$, 4 mM EGTA, 15 mM $KPO_4$, 1 mM DTT, 2.5 mM ATP). The plate was then read in a Dynatec multiwell luminometer that injected 75 μl of Luciferin buffer (25 mM Glycylglycine pH 7.8, 15 mM $MgSO_4$, 4 mM EGTA, 4 mM DTT, 1 mM luciferin) into each well, immediately reading the light emitted (light units).

The random sequence compound (Oligomer 48) and the other non-cholic acid-conjugated test compounds (Oligomers 43 and 46) had comparable activity. The 5'-conjugate of the first sequence (Oligomer 44) also had activity comparable to the non-conjugated compounds. The 5'-conjugate of the second sequence (Oligomer 47) showed a three-fold increase in activity compared to the non-conjugated compounds and the 3'-conjugate of the first sequence (Oligomer 45) showed a further 3-fold increase in activity compared to Oligomer 47.

All the test cholic acid-bearing oligonucleotides showed significant inhibition of luciferase production compared to non-cholic acid-bearing oligonucleotides. This suggests that the increased activity was the result of increased cellular membrane transport of the cholic acid-bearing test oligonucleotides.

Example 4

Preparation of Modified Nucleosides and Nucleotides, and Phosphoramidite and Controlled Pore Glass (CPG) Derivatives Thereof A. Preparation of 5'-O-[Dimethoxytrityl]-2'-O-[dimethoxytrityl]-3'-O-[hexyl(Ω-N-phthalimidoamino) uridine.

2',3'-O-Dibutyl stannylene-uridine was synthesized according to the procedure of Wagner et. al. (*J. Org. Chem.*, 1974, 39, 24). This compound was dried over $P_2O_5$ under vacuum for 12 hours. To a solution of this compound (29 g, 42.1 mmols) in 200 ml of anhydrous DMF were added (16.8 g, 55 mmols) of 6-bromohexyl phthalimide and 4.5 g of sodium iodide and the mixture was heated at 130° C. for 16 hours under argon. The reaction mixture was evaporated, co-evaporated once with toluene and the gummy tar residue was applied on a silica column (500 g). The column was washed with 2 L of ethyl acetate (EtOAc) followed by eluting with 10% methanol (MeOH):90% EtOAc. The product, 2'- and 3'-isomers of O-hexyl-Ω-N-phthalimido uridine, eluted as an inseparable mixture ($R_f$=0.64 in 10% MeOH in EtOAc). By $^{13}C$ NMR, the isomeric ration was about 55% of the 2' isomer and about 45% of the 3' isomer. The combined yield was 9.2 g (46.2%). This mixture was dried under vacuum and re-evaporated twice with pyridine. It was dissolved in 150 mL anhydrous pyridine and treated with 7.5 g of dimethyocytrityl chloride (22.13 mmols) and 500 mg of dimethylaminopyridine (DMAP). After 2 hour, thin layer chromatography (TLC; 6:4 EtOAc:Hexane) indicated complete disappearance of the starting material and a good separation between 2' and 3' isomers ($R_f$=0.29 for the 2' isomer and 0.12 for the 3' isomer). The reaction mixture was quenched by the addition of 5 mL of $CH_3OH$ and evaporated under reduced pressure. The residue was dissolved in 300 mL $CH_2Cl_2$, washed successively with saturated $NaHCO_3$ followed by saturated NaCl solution. It was dried over $Mg_2SO_4$ and evaporated to give 15 g of a brown foam which was purified on a silica gel (500 g) to give 6.5 g of the 2'-isomer and 3.5 g of the 3' isomer.

B. Preparation of 5'-O-Dimethoxytrityl-2'-O-[hexyl-(Ω-N-phthalimido)amino]uridine-3'-O-(2-cyanoethyl-N,N-diisopropyl)-phosphoramidite The 5'-dimethoxytrityl-2'-[O-hexyl-(Ω-N-phthalimido)-amino]uridine (4 g, 5.2 mmole) was dissolved in 40 mL of anhydrous CH₂Cl₂. To this solution diisopropylaminetetrazolide (0.5 g, 2.9 mmol) was added and stirred overnight. TLC (1:1 EtoAC/hexane) showed complete disappearance of starting material. The reaction mixture was transferred with CH₂Cl₂ and washed with saturated NaHCO₃ (100 mL) followed by saturated NaCl solution. The organic layer was dried over anhydrous Na₂SO₄ and evaporated to yield 6.4 g of a crude product which was purified in a silica column (200 g) using 1:1 hexane/EtOAc to give 4.6 g (4.7 mmol, 90%) of the desired phosphoramidite.

C. Preparation of 5'-O-(Dimethoxytrityl)-3'-O-[hexyl-(Ω-N-phthalimido)amino]uridine-2'-O-succinyl-aminopropyl controlled pore glass Succinylated and capped aminopropyl controlled pore glass (CPG; 500 Å pore diameter, aminopropyl CPG, 1.0 grams prepared according to Damha et. al. (*Nucl. Acids Res.*, 1990, 18, 3813.) was added to 12 ml anhydrous pyridine in a 100 ml round-bottom flask. 1-(3-Dimethylaminopropyl)-3-ethyl-carbo-diimide (DEC; 0.38 grams, 2.0 mmol)], triethylamine (TEA; 100 μl, distilled over CaH₂), dimethylaminopyridine (DMAP; 0.012 grams, 0.1 mmol) and nucleoside 5'-O-dimethoxytrityl-3'-O-[hexyl-(Ω-N-phthalimidoamino)]uridine (0.6 grams, 0.77 mmol) were added under argon and the mixture shaken mechanically for 2 hours. More nucleoside (0.20 grams) was added and the mixture shaken an additional 24 hours. CPG was filtered off and washed successively with dichloromethane, triethylamine, and dichloromethane. The CPG was then dried under vacuum, suspended in 10 ml piperidine and shaken 15 minutes. The CPG was filtered off, washed thoroughly with dichloromethane and again dried under vacuum. The extent of loading (determined by spectrophotometric assay of dimethoxytrityl cation in 0.3 M p-toluenesulfonic acid at 498 nm) was approximately 28 μmol/g. The 5'-O-(dimethoxytrityl)-3'-O-[hexyl-(Ω-N-phthalimidoamino]uridine-2'-O-succinyl-aminopropyl controlled pore glass was used to synthesize the oligomers 5'-GACU*-3' and 5'-GCC-TTT-CGC-GAC-CCA-ACA-CU*-3' (SEQ ID NO:13, where the * indicates the derivatized nucleotide) in an ABI 380B DNA synthesizer using phosphoramidite chemistry standard conditions. 45 and 200 O.D.'s of the 4-mer and 20-mer, respectively, were obtained from two and three 1 μmol syntheses after purification by RP-HPLC and desalting.

The oligomer 5'-GACU*-3' was used to confirm the structure of 3'-O-hexylamine tether introduced into the oligonucleotide by NMR. As expected a multiplet signal was observed between 1.0–1.8 ppm in ¹H NMR. The oligomer 5'-GCC-TTT-CGC-GAC-CCA-ACA-CU*-3' (SEQ ID NO:13) belongs to a HCV sequence and it was used to show the nuclease resistance properties of the 3'-O-amino tether (see, Example 5).

D. Preparation of 5'-O-(Dimethoxytrityl)-2'-O-[hexyl-(Ω-N-phthalimido)amino] 3'-O-succinylaminopropyl controlled pore glass The procedure of Example 4(C) was repeated, except that 5'-O-(Dimethoxytrityl)-2'-O-[hexyl-(Ω-N-phthalimidoamido)amino] uridine was used in the loading process.

E. Preparation of 5'-O-(Dimethoxytrityl)-2'-O-(hexylamino)-uridine

5'-O-(dimethoxytrityl)-2'-O-[hexyl-(Ω-N-phthalimido amino)]uridine (4.5 grams, 5.8 mmol) was dissolved in 200 ml methanol in a 500 ml flask. Hydrazine (1 ml, 31 mmol) was added to the stirring reaction mixture. The mixture was heated to 60–65° C. in an oil bath and refluxed 14 hours. Solvent was evaporated in vacuo. The residue was dissolved in dichloromethane (250 ml) and extracted twice with an equal volume NH₄OH. The organic layer was evaporated to yield 4.36 grams of crude product, and NMR indicated that the product was not completely pure. R$_f$=0 in 100% ethyl acetate. The product was used in subsequent reactions without further purification.

F. Preparation of 5'-O-(dimethoxytrityl)-3'-O-[hexylamino] uridine

The procedure of Example 4(E) was repeated, except that 5'-O-(dimethoxytrityl)-3'-O-[hexyl-(Ω-N-phthalimidoamino)] uridine was used as the starting material.

G. Preparation of 5'-O-(dimethoxytrityl)-2'-O-[hexyl-N-(1-pyrene propyl carbonyl)amino]uridine 5'-O-Dimethoxytrityl-2'-O-(hexylamino)uridine (0.5 g, 0.78 mmol) was dissolved in anhydrous DMF (15 mL). 1-Hydroxybenzotriazole (0.16 grams, 1.17 mmol) and 1-pyrene-butyric acid pentafluorophenyl ester (0.53 grams, 1.17 mmol) were added to the reaction mixture. The mixture was stirred under argon at room temperature for 2 hours, after which it was concentrated in vacuo. Residual DMF was coevaporated with toluene. The residue was dissolved in dichloromethane (50 mL) and washed with an equal volume saturated NaHCO₃. The aqueous layer was washed with dichloromethane and the combined organic extracts washed with an equal volume saturated NaCl. The aqueous layer was washed with dichloromethane and the combined organic layers dried over MgSO₄ and concentrated. The residue was chromatographed on a silica gel column, eluting with a gradient of 50% ethyl acetate in hexanes to 100% ethyl acetate. The desired product (0.83 grams, 58%) eluted with 100% ethyl acetate (R$_f$ 0.46 by thin-layer chromatography (TLC)).

H. Preparation of 5'-O-[Dimethoxytrityl]-2'-O-[hexyl-N-(1-pyrene propyl carbonyl)amino]uridine-3'-O-(2-cyanoethyl-N, N-diisopropyl)phosphoramidite 5'-O-[Dimethoxytrityl]-2'-O-[hexyl-N-(1-pyrene propyl carbonyl)amino] uridine (0.80 grams, 0.87 mmol) was dissolved in 20 mL dry dichloromethane. 2-Cyanoethyl N,N, N',N'-tetraisopropylphosphorodiamidite (purchased from Sigma Chemical Co; 800 μL, 2.4 mmol) and diisopropylamine tetrazolide (0.090 grams, 0.52 mmol) were added to the mixture, which was stirred under argon for 20 hours The reaction mixture was then concentrated in vacuo and the residue dissolved in dichloromethane (75 mL). The solution was washed with an equal volume of saturated NaHCO₃. The aqueous layer was washed with dichloromethane (20 mL) and the combined organic layers washed with an equal volume of saturated NaCl. The aqueous layer was washed with dichloromethane (20 mL) and the combined organic layers dried over MgSO₄ and concentrated. The residue was chromatographed on a silica gel column, eluting with a gradient of 50% ethyl acetate in hexanes to 100% ethyl acetate. The desired product (750 mg, 78% yield, R$_f$ 0.54 by TLC in 100% ethyl acetate) eluted with 100% ethyl acetate.

I. Preparation of 2'-O-[hexyl-N-(1-pyrene-propyl-carbonyl) amino] uridine

5'-O-dimethoxytrityl-2'-O-[hexyl-N-(1-pyrene-propyl-carbonyl)amino]uridine (1.0 g) was dissolved in 20 mL CH₂Cl₂ and kept in ice-bath for 10 minutes. To the cold solution, 5 mL of 80% acetic acid in water was added and the solution was left to stand for 30 minutes. It was then evaporated to dryness and loaded into a silica column and eluted with 10% methanol in methylene chloride to give 2'-O-[hexyl-N-(1-pyrene-propyl-carbonyl)amino]uridine.

J. Preparation of 5'-O-(dimethoxytrityl)-2'-O-[hexyl-N-(1-pyrene propyl carbonyl)amino]uridine-3'-O-[succinylaminopropyl-controlled pore glass Succinylated/capped aminopropyl controlled pore glass was dried under vacuum for 3 hours immediately before use. A portion (0.3 g) was added to 3 ml anhydrous pyridine in a 50 ml round-bottom flask. DEC (0.12 grams, 0.63 mmol), TEA (25 µl, distilled over CaH$_2$), DMAP (0.005 grams, 0.04 mmol) and 5'-O-(dimethoxytrityl)-3'-O-[hexyl-N-(1-pyrene propyl carbonyl] amino]uridine (0.21 grams, 0.22 mmol) were added under argon and the mixture shaken mechanically for 19 hours. More nucleoside (0.025 grams) was added and the mixture shaken an additional 5.5 hours. Pentachlorophenol (0.045 grams, mmol) was added and the mixture shaken 18 hours. CPG was filtered off and washed successively with dichloromethane, triethylamine, and dichloromethane. The resulting CPG was then dried under vacuum, suspended in 15 ml piperidine and shaken 30 minutes. CPG was filtered off, washed thoroughly with dichloromethane and again dried under vacuum. The extent of loading (determined by spectrophotometric assay of dimethoxytrityl cation in 0.3 M p-toluenesulfonic acid at 498 nm) was approximately 27 µmol/g. The product solid support was subsequently used to synthesize the oligomers.

K. Preparation of 5'-O-dimethoxytrityl-3'-O-[hexyl-N-(1-pyrene propyl carbonyl] amino] uridine-2'-O-(succinyl amino propyl) controlled pore glass The procedure of Example 4(J) is repeated, except that 5'-O-dimethoxytrityl-3'-O-[hexyl-N-(1-pyrene propyl carbonyl] amino] uridine is used.

L. Preparation of 5'-O-(dimethoxytrityl)-2'-O-[hexyl-N-(5-thio carbonyl-3,6-dipivolyl-fluorescein)amino]uridine Fluorescein isothiocyanate (Isomer I, available from Cal Biochem, La Jolla, Calif.) was treated with 12 equivalents of pivolyl chloride in Et$_3$N/THF to give di-O-pivolyl fluorescein isothiocyanate. This compound was purified in silica gel column using 3:1 hexane:ethyl acetate. Nucleoside 5'-O-(dimethoxytrityl)-2'-O-(hexylamino)uridine was then condensed with dipivolyl fluorescein isothiocyanate in CH$_2$Cl$_2$/pyrimidine. The resultant compound 5'-O-(dimethoxytrityl)-2'-O-[hexyl-N-(5-thiocarbonyl-3,6-dipivolyl-fluorescein)amino]uridine is then purified by using 100% ethyl acetate, in a silica column.

M. Preparation of 5'-O-dimethoxytrityl-2'-O-[hexyl-N-(5-thiocarbonyl-3,6-di-pivolyl fluorescein) amino] uridine-3'-O-(2-cyanoethyl, N-N-diisopropyl phosphoramidite 5'-O-(dimethoxytrityl)-2'-O-[hexyl-N-(5-thiocarbonyl-3,6-dipivolyl fluorescein)amino]uridine (0.75 grams, 0.672 mmol) was dissolved in dry dichloromethane (20 mL). 2-Cyanoethyl N,N,N',N'-tetraisopropylphosphorodiamidite (700 µL, 2.2 mmol) and diisopropylamine tetrazolide were added to the mixture, which was stirred under argon for 16 hours. The reaction mixture was then concentrated in vacuo and the residue dissolved in dichloromethane (75 mL) followed by washing with an equal volume of saturated NaHCO$_3$. The aqueous layer was washed with dichloromethane (50 mL) and the combined organic layers washed with an equal volume of saturated NaCl. The aqueous layer was washed with dichloromethane (50 mL) and the combined organic layers dried over MgSO$_4$ and concentrated. The residue was chromatographed on a silica gel column, eluting with a gradient of 25% ethyl acetate in hexanes to 100% ethyl acetate. The desired product (670 mg, 77% yield, R$_f$ 0.79 by TLC) eluted with 100% ethyl acetate.

N. Preparation of 5'-O-(dimethoxytrityl)-2'-O-[hexyl-N-(5-thiocarbonyl-3,6-di-pivolyl fluorescein)amino]uridine-3'-O-(succinylaminopropyl) controlled pore glass Succinylated and capped aminopropyl controlled pore glass (CPG) is dried under vacuum for 3 hours immediately before use. CPG (0.3 grams) is added to 3 ml anhydrous pyridine in a 50 ml round-bottom flask. DEC (0.12 grams, 0.63 mmol), TEA (25 µl, distilled over CaH$_2$, DMAP (dimethyl amino pyridine) (0.005 grams, 0.04 mmol) and 5'-O-dimethoxytrityl-2'-O-[hexyl-N-(5-thiocarbonyl-3,6-dipivolyl fluorescein) amino] uridine (0.21 grams, 0.19 mmol) are added under argon and the mixture shaken mechanically for 19 hours. More nucleoside (0.025 grams) is added and the mixture shaken an additional 5.5 hours. Pentachlorophenol (0.045 grams, 0.17 mmol) is added and the mixture shaken 18 hours. CPG is filtered off and washed successively with dichloromethane, triethylamine, and dichloromethane. CPG then is dried under vacuum, suspended in 15 mL piperidine and shaken 30 minutes. CPG is filtered off, washed thoroughly with dichloromethane, and again dried under vacuum. The extent of loading is then determined by spectrophotometric assay of dimethoxytrityl cation in 0.3 M p-toluenesulfonic acid at 498 nm.

O. Preparation of 5'-O-(dimethoxytrityl)-2'-O-[hexyl-N-(3-oxycarbonyl-cholesteryl)amino]uridine Nucleoside 5'-O-(dimethoxytrityl)-2'-O-[hexylamino]-uridine (3.85 g, 6.0 mmol) was dissolved in anhydrous pyridine/dichloromethane 50/50 (v/v) (20 mL). Cholesteryl chloroformate (Fluka, 3.0 g, 6.68 mmol) was dissolved in anhydrous dichloromehthane (20 ml) and added slowly under argon with a syringe to the stirring reaction mixture. The mixture was stirred under argon at room temperature for 2 h after which it was concentrated in vacuo. Residual DMF was coevaporated with toluene. The residue was dissolved in dichloromethane (50 mL) and washed with an equal volume saturated NaHCO$_3$. The aqueous layer was washed with dichloromethane and the combined organic extracts washed with an equal volume saturated NaCl. The aqueous layer was washed with dichloromethane and the combined organic layers dried over MgSO$_4$ and concentrated. The residue was chromatographed on a silica gel column with a gradient of 25% ethyl acetate in hexanes to 100% ethyl acetate. The desired product (3.78 g, 60%) eluted with 100% ethyl acetate (R$_f$ 0.41 by TLC).

P. Preparation of 5'-O-(dimethoxytrityl)-2'-O-[hexyl-N-(3-oxycarbonyl-cholesteryl)amino]uridine-3'-O-[2-cyanoethyl-N,N-diisopropyl]phosphoramidite Nucleoside 5'-O-(dimethoxytrityl)-2'-O-[hexyl-N-(3-oxycarbonyl-cholesteryl)amino]uridine (3.44 g, 3.3 mmol) was dissolved in dry dichloromethane (75 mL). 2-cyanoethyl N,N,N'N'-tetraisopropylphosphorodiamidite (Sigma, 2.1 ml, 6.6 mmol) and diisopropylamine tetrazolide (0.29 g, 1.7 mmol) were added to the mixture, which was stirred under argon for 16 H. Dichloromethane (75 mL) was added to the solution, which was washed with an equal volume of saturated NaHCO$_3$. The aqueous layer was washed with an equal volume of dichloromethane. The aqueous layer was washed with dichloromethane (30 ml) and the combined organic layers washed with an equal volume of saturated NaCl. The aqueous layer was washed with dichloromethane (30 mL) and the combined organic layers dried over Mg$_2$SO$_4$ and concentrated in vacuo. The residue was chromatographed on a silica gel column with a gradient of 25% ethyl acetate in hexanes to 70% ethyl acetate. The desired product (3.35 g, 82% yield, R$_f$=0.71 by TLC in 50% ethyl acetate in hexanes) eluted with 50% ethyl acetate.

Q. Preparation of 5'-O-(dimethoxytrityl)-2'-O-[hexyl-N-(3-oxycarbonyl-cholesteryl)amino]uridine-3'-O-(succinyl aminopropyl)-controlled pore glass Succinylated and capped controlled pore glass (0.3 grams) is added to 2.5 ml anhydrous pyridine in a 15 ml pear-shaped flask. DEC (0.07 grams, 0.36 mmol), TEA (100

μl, distilled over CaH₂), DMAP (0.002 grams, 0.016 mmol) and 5'-O-(dimethoxytrityl)-2'-O-[hexyl-N-(3-oxycarbonyl-cholesteryl)-amino]uridine (0.25 grams, 0.23 mmol) are added under argon and the mixture shaken mechanically for 16 hours. More nucleoside (0.20 grams) is added and the mixture shaken an additional 18 hours. Pentachlorophenol (0.03 grams, 0.11 mmol) is added and the mixture shaken 9 hours. CPG is filtered off and washed successively with dichloromethane, triethylamine, and dichloromethane. CPG is then dried under vacuum, suspended in 10 ml piperidine and shaken 15 minutes. CPG is filtered off, washed thoroughly with dichloromethane and again dried under vacuum. The extent of loading is determined by spectrophotometric assay of dimethoxytrityl cation in 0.3 M p-toluenesulfonic acid at 498 nm as approximately 39 μmol/g.

R. Preparation of 5'-O-(dimethoxytrityl)-2'-O-[hexyl-N-(2,4-dinitrophenyl)amino]uridine 5'-O-(dimethoxytrityl)-2'-O-(hexylamino)uridine (0.88 grams, 1.37 mmol) was dissolved in methanol (20 mL). 2,4-Dinitrofluorobenzene (DNFB, 0.25 grams, 1.37 mmol) was added and the mixture shaken on a mechanical shaker. The reaction was monitored by TLC. After 90 minutes, another 0.25 grams of DNFB was added and the reaction mixture shaken an additional 30 minutes, followed by addition of another 0.25 grams of DNFB. After shaking 2.5 hours, the mixture was concentrated in vacuo and chromatographed on a silica gel column, eluting with a gradient of 25% ethyl acetate in hexanes to 100% ethyl acetate. The desired product (0.51 grams, 46%) eluted with 100% ethyl acetate ($R_f$ 0.85 by TLC).

S. Preparation of 5'-O-(dimethoxytrityl)-2'-O-[hexyl-N-(2,4-dinitrophenyl)amino]uridine-3'-O-(2-cyanoethyl-N,N-diisopropyl)phosphoramidite 5'-O-(dimethoxytrityl)-2'-O-[hexyl-N-(2,4-dinitrophenyl)amino]uridine (0.45 grams, 0.55 mmol) was dissolved in dry dichloromethane (12 mL). 2-Cyanoethyl N,N,N',N'-tetraisopropylphosphorodiamidite (380 μL, 1.2 mmol) and diisopropylamine tetrazolide (0.041 grams, 0.024 mmol) were added to the mixture, which was stirred under argon for 16 hours. The reaction mixture was then concentrated in vacuo and the residue dissolved in dichloromethane (75 mL) followed by washing with an equal volume of saturated NaHCO₃. The aqueous layer was washed with dichloromethane (25 mL) and the combined organic layers washed with an equal volume of saturated NaCl. The aqueous layer was washed with dichloromethane (25 mL) and the combined organic layers dried over MgSO₄ and concentrated. The residue was chromatographed on a silica gel column, eluting with a gradient of 20% ethyl acetate in hexanes to 100% ethyl acetate. The desired product (510 mg foam, 93% yield, $R_f$ 0.70 by TLC) eluted with 100% ethyl acetate. ³¹PNMR (CDCl₃):150.56 and 150.82 ppm.

T. Preparation of 5'-O-(dimethoxytrityl)-2'-O-[hexyl-N-(2,4-dinitrophenyl)amino]uridine-3'-O-(succinyl aminopropyl) controlled pore glass Succinylated and capped controlled pore glass (0.3 grams) is added to 3 ml anhydrous pyridine in a 50 ml round-bottom flask. DEC (0.12 grams, mmol), TEA (25 μl, distilled over CaH₂), DMAP (0.005 grams, 0.041 mmol) and 5'-O-(di-methoxytrityl)-2'-O-[hexyl-N-(2,4-dinitrophenyl)amino]uridine (0.21 grams, 0.26 mmol) are added under argon and the mixture shaken mechanically for 19 hours. More nucleoside (0.025 grams) is added and the mixture shaken an additional 5.5 hours. Pentachlorophenol (0.045 grams, 0.16 mmol) is added and the mixture shaken 18 hours. CPG is filtered off and washed successively with dichloromethane, triethylamine, and dichloromethane. CPG then is dried under vacuum, suspended in 15 ml piperidine and shaken for 15 minutes. CPG is filtered off, washed thoroughly with dichloromethane, and again dried under vacuum. The extent of loading is determined by spectrophotometric assay of dimethoxytrityl cation in 0.3 M p-toluenesulfonic acid at 498 nm, as approximately 29 μmol/gm.

U. Preparation of 5'-O-(dimethoxytrityl)-2'-O-[hexyl-N-(Nα-Nimid-Di-FMOC-L-Histidyl)amino]uridine Nucleoside 5'-O-(dimethoxytrityl)-2'-O-(hexylamino)uridine (0.97 g, 1.51 mmol) was dissolved in dichloromethane (25 mL) and cooled to 0° C. in an ice bath. Nα,Nimid-Di-FMOC-L-histine pentafluorophenyl ester (2.4 g, 3.1 mmol, purchased from Sigma) and 1-hydroxybenzotriazole (0.32 g, 0.24 mmol, purchased from Fluka) were added to the stirred reaction mixture stirred under argon. After 15 minutes, the ice bath was removed and the mixture stirred under argon at room temperature for 72 h. The mixture was concentrated in vacuo and chromatographed on a silica gel column, eluting with a gradient of 50% ethyl acetate in hexanes to 70% ethyl acetate in hexanes. The desired product (0.53 g, 28%) eluted with 70% ethyl acetate ($R_f$ 0.53 by TLC in 100% ethyl acetate).

V. Preparation of 5'-O-(dimethoxytrityl)-2'-O-[hexyl-N-(Nα-Nimid-Di-FMOC-L-histidyl)-amino]-uridine-3'-O-[2-cyanoethyl-N,N-diisopropyl]phosphoramidite 5'-O-Dimethoxytrityl-2'-O-[hexyl-N-(Nα-Nimid-Di-FMOC-L-histidyl)amino]uridine (1.9 g, 1.6 mmol) is dissolved in dry dichloromethane (20 mL). 2-Cyanoethyl N,N,N',N'-tetraisopropylphosphorodiamidite (800 μL, 2.4 mmol) and diisopropylamine tetrazolide (0.090 grams, 0.52 mmol) are added to the mixture, which is stirred under argon for 20 hours. The reaction mixture then is concentrated in vacuo and the residue dissolved in dichloromethane (75 mL). The solution is washed with an equal volume of saturated NaHCO₃. The aqueous layer is washed with dichloromethane (20 mL) and the combined organic layers washed with an equal volume of saturated NaCl. The aqueous layer is washed with dichloromethane (20 mL) and the combined organic layers dried over MgSO₄ and concentrated. The residue is chromatographed on a silica gel column, eluting with a gradient of 50% ethyl acetate in hexanes to 100% ethyl acetate. The desired product elutes with 100% ethyl acetate.

W. Preparation of 5'-O-(dimethoxytrityl)-2'-O-[hexyl-N-(Nα-Nimid-Di-FMOC)-L-histidyl)amino]uridine-3'-O-[succinylaminopropyl] controlled pore glass Succinylated and capped controlled pore glass (dried under vacuum for 3 hours immediately before use; 0.3 grams) is added to 3 ml anhydrous pyridine in a 50 ml round-bottom flask. DEC (0.12 grams, 0.63 mmol), TEA (25 μl, distilled over CaH₂), DMAP (0.005 grams, 0.04 mmol) and 5'-O-(dimethoxytrityl)-2'-O-[hexyl-N-(Nα-Nimid-Di-FMOC)-L-histidyl)amino]-uridine (0.21 grams, 0.17 mmol) are added under argon and the mixture shaken mechanically for 19 hours. More nucleoside (0.025 grams) is added and the mixture shaken an additional 5.5 hours. Pentachlorophenol (0.045 grams, 0.17 mmol) is added and the mixture shaken 18 hours. CPG is filtered off and washed successively with dichloromethane, triethylamine, and dichloromethane. CPG then is dried under vacuum, suspended in 15 ml piperidine and shaken 15 minutes. CPG is filtered off, washed thoroughly with dichloromethane and again dried under vacuum. The extent of loading is determined by spectrophotometric assay of dimethoxytrityl cation in 0.3 M p-toluenesulfonic acid at 498 nm. to be approximately 27 μmol/g.

X. Preparation of 5'-O-(dimethoxytrityl)-2'-O-[hexyl-N-(Ω-methyl-polyethylene glycolpropionoyl)amino]uridine Nucleoside 5'-O-(dimethoxytrityl)-2'-O-[hexylamino]-uridine, (1 g, 1.55 mmol) is dissolved in anhydrous DMF (15 mL). 1-Hydroxybenzotriazole (0.24 g, 1.75 mmol) and polyethylene glycol-propionic acid-NHS-ester (1.23 g, 1.75 mmol) are added to the reaction mixture. The mixture is stirred under argon at room temperature for 2 hours after which it is concentrated in vacuo. Residual DMF is coevaporated with toluene. The residue is dissolved in dichloromethane (50 mL) and then washed with an equal volume saturated NaHCO$_3$. The aqueous layer is washed with dichloromethane and the combined organic extracts washed with an equal volume saturated NaCl. The aqueous layer is washed with dichloromethane and the combined organic layers dried over MgSO$_4$ and concentrated. The residue is chromatographed on a silica gel column, eluting with a gradient of 50% ethyl acetate in hexanes to 100% ethyl acetate. The desired product (1.08 g, 58%) eluted with 100% ethyl acetate.

Y. Preparation of 5'-O-(dimethoxytrityl)-2'-O-[hexyl-N-(Ω-methyl-polyethylene glycol-propionoyl)amino]uridine-3'-O-(2-cyanoethoxy-N,N-diisopropyl)phosphoramidite 5'-O-(Dimethoxytrityl)-2'-O-[hexyl-N-(Ω-methyl-polyethylene glycol-propionoyl)amino]uridine (1.04 grams, 0.87 mmol) is dissolved in dry dichloromethane (20 mL). 2-Cyanoethyl N,N,N'-tetraisopropylphosphorodiamidite (800 μL, 2.4 mmol) and diisopropylamine tetrazolide (0.090 grams, 0.52 mmol) are added to the mixture, which is stirred under argon for 20 hours. The reaction mixture then is concentrated in vacuo and the residue dissolved in dichloromethane (75 mL). The solution is washed with an equal volume of saturated NaHCO$_3$. The aqueous layer is washed with dichloromethane (20 mL) and the combined organic layers washed with an equal volume of saturated NaCl. The aqueous layer is washed with dichloromethane (20 mL) and the combined organic layers dried over MgSO$_4$ and concentrated. The residue is chromatographed on a silica gel column, eluting with a gradient of 50% ethyl acetate in hexanes to 100% ethyl acetate. The desired product elutes with 100% ethyl acetate.

Z. Preparation of 5'-O-(dimethoxytrityl)-2'-O-[hexyl-N-(Ω-methyl-polyethylene glycol-propionoyl)amino]uridine-3'-O-(succinyl-aminopropyl) controlled pore glass Succinylated and capped controlled pore glass (CPG) is dried under vacuum for 3 hours immediately before use. Controlled pore glass (0.3 grams) is added to 3 ml anhydrous pyridine in a 50 ml round-bottom flask. DEC (0.12 grams, 0.67 mmol), TEA (25 μl, distilled over CaH$_2$), DMAP (0.005 grams, mmol) and 5'-O-(dimethoxytrityl)-2'-O-[hexyl-N-(w-methyl-polyethylene glycol-propionoyl)amino]uridine (0.21 grams, 0.175 mmol) are added under argon and the mixture shaken mechanically for 19 hours. More nucleoside (0.025 grams) is added and the mixture shaken an additional 5.5 hours. Pentachlorophenol (0.045 grams, 0.17 mmol) is added and the mixture shaken 18 hours. CPG is filtered off and washed successively with dichloromethane, triethylamine, and dichloromethane. CPG then is dried under vacuum, suspended in 15 ml piperidine, and shaken 15 minutes. CPG is filtered off, washed thoroughly with dichloromethane, and again dried under vacuum. The extent of loading is determined by spectrophotometric assay of dimethoxytrityl cation in 0.3 M p-toluenesulfonic acid at 498 nm. to be approximately 18 μmol/g.

AA. Preparation of macrocycle derivatized nucleoside

5'-O-(dimethoxytrityl)-2'-O-(hexylamine)uridine is treated as per the procedure of Example 3 with the macrocycle 4-{1,4,8,11-tetraza-[tri-(trifluoroacetyl)cyclotetradec-1-yl]}methyl benzoic acid-N-hydroxy succinimide ester (prepared according to Simon Jones et. al. (*Bioconjugate Chem.* 1991, 2, 416) to yield the product.

AB. Preparation of macrocycle derivatized uridine phosphoramidite

The nucleoside product of Example 4(AA) is treated as per the procedure of Example 4(B) to yield the product.

AC. Preparation of CPG derivatized with macrocycle derivatized nucleoside

The nucleoside product of Example 4(AA) is treated as per the procedure of Example 4(C) to yield the product.

AD. Preparation of 5'-O-(dimethoxyltrityl)-2'-O-(hexyl-N-(folate)amino)uridine

5'-O-(Dimethoxytrityl)-2'-O-(hexylamine)uridine is treated as per the procedure of Example 4(A) with folic acid pentafluorophenyl ester (protected with an isobutyryl protecting group) to yield the product.

AE. Preparation of 5'-O-(dimethoxyltrityl)-2'-O-[hexyl-N-(folate)amino]uridine-3'-O-(2-cyanoethoxy-N,N-diisopropyl)phosphoramidite The nucleoside product of Example 4(AB) is treated as per the procedure of Example 4(B) to yield the product.

AF. Preparation of CPG derivatized with 5'-O-(dimethoxyltrityl)-2'-O-(hexyl-N-(folate)amino)-uridine nucleoside The nucleoside product of Example 4(AE) is treated as per the procedure of Example 4(C) to yield the product.

AG. Preparation of 5'-O-(dimethoxytrityl)-2'-O-{hexyl-N-[2-methoxy-6-chloro-9-(Ω-amino-caproyl)acridine]amino}uridine 6,9-Dichloro-2-methoxyacridine (Alrich, 10 g, 36 mmol) and phenol (2.5 g) were placed together on a round-bottom flask with a stirring bar and to this 6-amino-hexanoic acid (9.3 g, 71 mmol) was added and the flask was heated to 100° C. (oil bath) for 2 hours. TLC (10% methanol in methylene chloride) showed complete disappearance of starting material. The reaction mixture was cooled and poured into 200 mL of methanol. The product isolates out as a yellow solid (about 10 g). This compound was then converted into its pentafluorophenol ester.

5'-O-(Dimethoxytrityl)-2'-(hexylamino)uridine (0.5 g, 0.78 mmol) is dissolved in anhydrous DMP (15 mL). 1-Hydroxy-benzotriazole (0.16 grams, 1.17 mmol) and 2-methoxy-6-chloro-9-(Ω-caproyl-amino) acridine pentafluorophenyl ester (0.53 grams, 1.17 mmol) are added to the reaction mixture. The mixture is stirred under argon at room temperature for 2 h, after which it is concentrated in vacuo. Residual DMF is coevaporated with toluene. The residue is dissolved in dichloromethane (50 mL) and washed with an equal volume saturated NaHCO$_3$. The aqueous layer is washed with dichloromethane and the combined organic extracts washed with an equal volume saturated NaCl. The aqueous layer is washed with dichloromethane and the combined organic layers dried over MgSO$_4$ and concentrated. The residue is chromatographed on a silica gel column, eluting with a gradient of 50% ethyl acetate in hexanes to 100% ethyl acetate. The desired product elutes with 100% ethyl acetate.

AH. Preparation of 5'-O-(dimethoxytrityl)-2'-O-{hexyl-N-[2-methoxy-6-chloro-9-(Ω-amino-caproyl)acridine]amino}uridine-3'-O-(2-cyanoethyl-N-N-diisopropyl) phosphoramidite 5'-O-Dimethoxytrityl-2'-O-{hexyl-N-[2-methoxy-6-chloro-9-(w-amino-caproyl)acridine]amino}uridine (0.80 grams, 0.77 mmol) is dissolved in dry dichloromethane (20 mL). 2-Cyanoethyl N,N,N',N'- tetraisopropylphosphorodiamidite (800 μL, 2.4 mmol) and diisopropylamine tetrazolide (0.090 grams, 0.52 mmol) are added to the mixture, which is stirred under argon for 20 hours. The reaction mixture is then concentrated in vacuo and the residue dissolved in dichloromethane (75 mL). The solution is washed with an equal volume of saturated NaHCO$_3$. The aqueous layer is washed with dichloromethane (20 mL) and the combined organic layers washed with an equal volume of saturated NaCl. The aqueous layer is washed with dichloromethane (20 mL) and the combined organic layers dried over MgSO$_4$ and concentrated. The residue is chromatographed on a silica gel column, eluting with a gradient of 50% ethyl acetate in hexanes to 92% ethyl acetate. The desired product elutes with 100% ethyl acetate.

AI. Preparation of 5'-O-(dimethoxytrityl)-2'-O-{hexyl-N-[2-methoxy-6-chloro-9-(Ω-aminocaproyl)acridine]amino}uridine-3'-O-(succinyl aminopropyl) controlled pore glass Succinylated and capped controlled pore glass (0.3 grams) is added to 3 ml anhydrous pyridine in a 50 ml round-bottom flask. DEC (0.12 grams, 0.67 mmol), TEA (25 μl, distilled over CaH$_2$), DMAP (0.005 grams, 0.04 mmol) and 5'-O-dimethoxytrityl-2'-O-{hexyl-N-[2-methoxy-6-chloro-9-(Ω-aminocaproyl)acridine]amino}uridine (0.21 grams, 0.17 mmol) are added under argon and the mixture shaken mechanically for 19 hours. More nucleoside (0.025 grams) is added and the mixture shaken an additional 5.5 hours. Pentachlorophenol (0.045 grams, 0.17 mmol) is added and the mixture shaken 18 hours. CPG is filtered off and washed successively with dichloromethane, triethylamine, and dichloromethane. CPG is then dried under vacuum, suspended in 15 ml piperidine and shaken 15 minutes. CPG is filtered off, washed thoroughly with dichloromethane and again dried under vacuum. The extent of loading is determined by spectrophotometric assay of dimethoxytrityl cation in 0.3 M p-toluenesulfonic acid at 498 nm. to be approximately 27 μmol/g.

AJ. Preparation of 5'-O-(dimethoxytrityl)-2'-O-[(hexyl-N,N-dimethyl)amino]uridine 5'-O-(dimethoxytrityl)-2'-O-(hexylamino)uridine (0.19 grams, 0.29 mmol) is dissolved in 4 ml methanol. Sodium acetate pH 4.0 (2 ml), sodium cyanoborohydride (0.02 grams, 0.3 mmol) and 37% formaldehyde in water (300 μl) are added to the reaction mixture, which is stirred 2 hours, after which it is concentrated in vacuo. The residue is dissolved in dichloromethane (50 mL) and washed with an equal volume saturated NaHCO$_3$. The aqueous layer is washed with dichloromethane and the combined organic extracts washed with an equal volume saturated NaCl. The aqueous layer is washed with dichloromethane and the combined organic layers dried over MgSO$_4$ and concentrated. The residue is chromatographed on a silica gel column, eluting with a gradient of 50% ethyl acetate in hexanes to 100% ethyl acetate. The desired product (0.15 grams, 80%) elutes with 10% Methanol-90% ethyl acetate.

Example 5

Oligonucleotides Having a 3'-alkylamino Group

3'-O-Hexyl-(N-phthalimido)-aminouridine-CPG, i.e. the 5'-O-dimethoxytrityl-3'-O-[hexyl-(Ω-N-phthalimido amino)]-uridine-2'-O-(succinyl-aminopropyl) controlled pore glass from Example 4(C), was used to synthesize the following oligonucleotides:

Oligomer 49: 5'-GACU*
Oligomer 50: 5'-GCC-TTT-CGC-GAC-CCA-ACA-CU (SEQ ID NO:13)
Oligomer 51: 5'-GCC-TTT-CGC-GAC-CCA-ACA-CU* (SEQ ID NO:13), wherein "*" denotes the 3'-O hexylamino-modified nucleoside. Standard commercial phosphoramidites were used with the synthesis cycle times specified by the manufacturer in a 380B ABI instrument (Applied Biosystems).

Oligomer 49 was used for structural proof of 3'-O-alkylamine-bearing oligonucleotides at the 3'-terminal end. It showed the expected three $^{31}$P NMR signals (−0.5 ppm, −0.25 ppm, −0,2 ppm) and seven lines in the trace aromatic base region in $^1$H NMR its spectrum.

Oligomer 51 was used to demonstrate the nuclease resistance offered by this the alkylamino group and also for further conjugation. The oligomer was treated with pyrenebutyric acid-N-hydroxy succinimide ester in 0.2 M NaHCO$_3$ buffer/DMF. The product, Conjugate 1, was purified by HPLC and size exclusion methods. HPLC retention times (eluting with a gradient of 5% CH$_3$CN for 10 minutes then 5%–40% CH$_3$CN for 50 minutes) were as follows: Oligomer 50, 25.99 min.; Oligomer 51, 25.91 min.; and Conjugate 1, 49.35 min.

The nuclease stability of Oligomer 51 and the conjugate were tested against Oligomer 50 in HeLa cytoplasmic/nuclear extracts. The cell extract was diluted 1.4 times. The final concentration of oligonucleotide was 20 μM. The half lives of the oligonucleotides were as follows: Oligomer 50, 1.0 hrs.; Oligomer 51, 3.5 hrs.; and Conjugate 1, 3.6 hrs.

The half life of phosphodiester Oligomer 50 increased 3–4 times by simple modification at the 3'-end with the hexylamino group by itself, an attribute that was unaffected by further conjugation.

Example 6

2'-O-Modified Oligonucleotides

A. GCGTGU*CTGCG where U* is hexyl-(Ω-N-phthalimido)amino]-uridine

The phosphoramidite from Example 4(B), 5'-O-(dimethoxytrityl)-2'-O-[hexyl-(Ω-N-phthalimido)amino]-uridine-3'-O-[(2-cyanoethyl)-N,N-diisopropyl] phosphoramidite was made as a 0.2 M solution in anhydrous CH$_3$CN and used to synthesize the following oligonucleotides in an ABI DNA synthesizer, model 380 B. During the modified amidite coupling, the reaction time was increased to 10 minutes. A coupling efficiency of approximately 90% was observed. After deprotection with concentrated ammonium hydroxide (55° C., 16 hours) the following oligonucleotides were purified by reverse phase HPLC and desalting column (Sephadex G-25):

Oligomer 52: 5'-GCG-TGU*-CTG-CG (SEQ ID NO:14); and

Oligomer 53: 5'-GAU*CT.

B. GCGTGTU'CTGCG where U' is 2'-O-[hexyl-N-(1-pyrene-propyl-carbonyl)amino uridine, Conjugate 2 (Oligomer 52—pyrene butyrate conjugate).

To 20 O.D. of Oligomer 52 in 200 μL of 0.2 M NaHCO$_3$ buffer, 5 ml of pyrene-butyric acid-N-hydroxy succinimide ester in an Eppendorf tube was added followed by 200 μL of DMF. The tube was shaken overnight. The reaction was purified by size exclusion and HPLC to yield 18 O.D. of product.

C. GCGTGTU*CTGCG where U* is 2'-O-[6-bromoacetymido-hex-1yl]-uridine, Conjugate 3 (Oligomer 52—bromoacetate conjugate).

To 12 O.D. of Oligomer 52 in 100 μL of 0.2 M NaHCO$_3$ buffer, 2 mg bromoacetic acid-NHS ester (N-hydroxy succinimidyl bromoacetate) was added. After leaving the reaction to stand overnight, it was purified by size exclusion and HPLC to yield 7.5 O.D. of product.

D. GCGTGTU^CTGCG where U^ is 2'-O-[hexyl-N-(polyethylene glycol)-propionoyl]amino uridine, Conjugate 4 (Oligomer 52—PEG conjugate).

To 24 O.D. of Oligomer 52 in 200 μL of 0.2 M NaHCO$_3$ buffer, 20 mg of Polyethylene glycol propionic acid-N-hydroxy succinimide ester was added. The reaction was mechanically shaken overnight and purified by Sephadex G-25 size exclusion and chromatography to yield 22 O.D. of product.

HPLC retention times (eluting with a gradient of 5% CH$_3$CN for 10 minutes then 5%–40% CH$_3$CN for 50 minutes in a C-18 Delta-Pak reverse phase column) were as follows: Oligomer 52, 24.05 min.; Conjugate 2, 40.80 min.; Conjugate 3, 26.04 min.; and Conjugate 4, 55.58 min.

Changes in T$_m$ due to pyrene conjugation were evaluated against both DNA and RNA. T$_m$ was measured in 100 mM Na$^+$, 10 nM phosphate, 0.1 mM EDTA, pH 7 at 4 μM strand concentration.

The results were as follows:

TABLE 5

MELTING TEMPERATURE OF THE HYBRIDIZATION COMPLEX OF OLIGONUCLEOTIDE AND ITS COMPLEMENTARY STRAND

|  | T$_m$ v, DNA (° C.) | T$_m$ v, RNA (° C.) |
| --- | --- | --- |
| Oligomer 52 | 50.9 | 55.5 |
| Conjugate 2 | 55.3 | 55.5 |
| Δ$_{o52-C2}$ | (4.4) | (0.0) |

The values in parentheses are changes in T$_m$ compared to amino linker in oligomer 52 as a control.

Example 7

Oligonucleotide Synthesis Using 2'-O-Hexylamino-functionalized Uridine Phosphoramidites A. 2'-O-hexylamino(pyrenebutyrate)uridine phosphoramidite The amidite 5'-O-(dimethoxytrityl)-2'-O-[hexyl-N-(1-pyrene propyl carbonyl)amino]uridine-3'-O-(2-cyanoethyl-N,N-diisopropyl) phosphoramidite (0.2 M in anhydrous acetonitrile) was used to synthesize the following oligomers, both for NMR studies:

Oligomer 54: 5'-GAU*CT, and
Oligomer 55: 5'-GCC-GU*G-TCG,
where U* is a 2'-O-modified phosphoramidite.

These oligomers were purified trityl-on reverse-phase HPLC, detritylated in 80% acetic acid for one hour and then repurified by RP-HPLC and desalted by size-exclusion chromatography. NMR analysis showed the presence of pyrene peaks.

B. 2'-O-hexylamino(dinitrophenyl)uridine phosphoramidite

The amidite 5'-O-(dimethoxytrityl)-2'-O-[hexyl-N-(2,4-dinitrophenyl)amino]uridine-3'-O-(2-cyanoethyl-N,N,-diiso-propyl)phosphoramidite (0.18 M in anhydrous acetonitrile) was used to synthesize the oligonucleotides, Oligomers 56 to 63. All are analogues of an ICAM antisense sequence. These oligomers were purified trityl-on by RP-HPLC (Waters Delta-Pak C$_{18}$ column, 300 Å, 7.8 mm×30 cm, linear 50-min gradient of 5–60% acetonitrile in 0.05 M TEAA pH 7.3), detritylated in 80% acetic acid for one hour and then purified by RP-HPLC and desalted by size-exclusion chromatography. Data are summarized below in Table 6:

TABLE 6

HPLC RETENTION TIMES OF OLIGONUCLEOTIDES

|  | Backbone | Total (O.D.) | Retention Time (min.) |
| --- | --- | --- | --- |
| Oligomer 56; GAU*CT | P=O | 40 | 39.16 |
| Oligomer 57 (SEQ ID NO:15): U*GG-GAG-CCA-TAG-CGA-GGC# | P=S | 64 | 39.19 |
| Oligomer 58 (SEQ ID NO:15): U*GG-GAG-CCA-TAG-CGA-GGC | P=S | 45 | 39.21 |
| Oligomer 59 (SEQ ID NO:15): U*GG GAG CCA TAG CGA GGC | P=O | 60 | 37.68 |
| Oligomer 60 (SEQ ID NO:5): U*GG GAG CCA U*AG CGA GGC | P=O | 69 | 38.58 |
| Oligomer 61 (SEQ ID NO:16): TGG GAG CCA U*AG CGA GGC | P=O | 86 | 32.38 |
| Oligomer 62 (SEQ ID NO:17): | P=O | 34 | 35.76 |
| Oligomer 63 (SEQ ID MO:S): U*GG GAG CCA U*AG CGA GGC# | P=S | 72 | 43.37 |

=Non-nucleoside 6-carbon amino linker (Glen Research) and Bold indicates nucleotides having 2'-O-methyl substitutions C. Oligonucleotide synthesis using 2'-O-[hexylamino-(cholesterol)]uridine phosphoramidite The amidite 5'-O-dimethoxytrityl-2'-O-[hexyl-N-(3-oxycarbonyl-cholesteryl)amino]uridine-3'-O-[2-cyanoethyl-N,N,-diisopropyl]-phosphoramidite (0.2 M in anhydrous aceto-nitrile/dichloromethane 2:1 v/v) was used to synthesize Oligomers 67–74. These oligomers are purified trityl-on by reverse-phase HPLC (Waters Delta-Pak C$_{18}$, 300 Å, 7.8 mm×30 cm, linear 55-min gradient of 5–80% acetonitrile in 0.05 M TEAA pH 7.3), detritylated in 80% acetic acid for one hour and then repurified by RP-HPLC and desalted by size-exclusion chromatography. Data are summarized below in Table 7.

TABLE 7

HPLC RETENTION TIMES OF OLIGONUCLEOTIDES

|  | Backbone | Target (use) | Retention Time (min.) |
| --- | --- | --- | --- |
| Oligomer 67; GAU*CT | P=O | (NMR) | 52.73 |
| Oligomer 68 (SEQ ID NO:15): U*GG-GAG-CCA-TAG- CGA-GGC | P#O | ICAM | 49.64 |
| Oligomer 69 (SEQ ID NO:1S): U*GC-CCA-AGC-TGG-CAT-CCG-TCA | P=S | ICAM | 51.98 |
| Oligomer 70 (SEQ ID NO:19): U*GC-GTT-TGC-TCT-TCT-TCT-TGC-G | P=S | CMV | 52.57 |
| Oligomer 71 (SEQ ID NO:20): U*GC-ATC-CCC-CAG-GCC-ACC-AT | P=S ICAM | mse- | 53.24 |
| Oligomer 72 (SEQ ID NO:21): U*CC-CGC-CTG-TGA-CAT-GCA-TT | p=S | Raf | 53.95 |
| Oligomer 73 (SEQ ID NO:22): GU*T-CT-GCT-GGT-GAG-TTT-CA | p=S | PKCcx | 51.04 |
| Oligomer 74 (SEQ ID NO:23): Fl-UU*GG-GAG-CCA-TAG-CGA-GGC | P=S | ICAM | 52.75 |

(Fl-U = U 2'-modified with fluorescein; see Example 8(A))

D. Synthesis of oligonucleotides using 2'-O-[hexylamino-(fluorescein)] amidite

The amidite 5'-O-dimethoxytrityl-2'-O-[hexyl-N-(5-thiocarbonyl-3,6-dipivolyl fluorescein)amino]uridine-3'-O-

(cyanoethyl-N,N-diisopropyl phosphoramidite) (0.2 M in anhydrous acetonitrile) was used to synthesize Oligomer 74 (above) and Oligomers 75–82 on a 1×10$^5$ (Oligomer 75) or 1×10$^2$ (remaining Oligomers) μmol scale. These oligomers are purified trityl-on by reverse phase HPLC (Waters Delta-Pak C$_{18}$, 300 Å, 7.8 mm×30 cm, linear gradient of acetonitrile in 0.05 M TEAA pH 7.3), detritylated in 80% acetic acid for one hour and then repurified by RP-HPLC and desalted by size-exclusion chromatography.

TABLE 8

STRUCTURES OF OLIGOMHRS 75 To 82

| | Backbone | Target |
|---|---|---|
| oligomer 75: GAU*CT | P=O | (NMR) |
| Oligomer 76 (SEQ ID NO:15): U*GG-GAG-CCA-TAG-CGA-GGC | P=O | ICAM |
| Oligomer 77 (SEQ ID NO:6): U*GC-CCA-AGC-TGG-CAT-CCG-TCA 33 | P=S | ICAM |
| Oligomer 78 (SEQ ID NO:6): U*GC-CCA-AGC-TGG-CAT-CCG-TCA# | P=S | ICAM |
| Oligomer 79 (SEQ ID NO:19): U*GC-GTT-TGC-TCT-TCT-TCT-TGC-G | P=S | CMV |
| Oligomer 80 (SEQ ID NO:20): U-GC-ATC-CCC-CAG-GCC-ACC-AT | P=S | mseICAM |
| Oligomer 81 (SEQ ID NO:20): U*GC-ATC-CCC-CAG-GCC-ACC-A(U-CPG) where (U-CPG)=2'-O-hexylphthalimido U 6 | P=S | mseICAM, |
| Oligomer 82 (SEQ ID NO:22): GU*T-CTC-GCT-GGT-GAG-TTT-CA where U* is U modified with fluorescein. | P=S | PKC, |

Example 8

Preparation of Derivatized Thymidine Phosphoramidites

A. 3-Benzyloxymethyl-3'-benzyloxymethyl-5'-O-tert-butyldiphenyl silylthymidine

To a mechanically stirred solution of 5'-O-tertbutyl-diphenylsilylthymidine (170 g, 350 mmol) and diisopropy-lethylamine (200 g, 1547 mmol) in methylene chloride (1000 ml) was added dropwise benzyl chloromethylether (171 g, 1092 mmol). Upon completion of a mild exotherm, the reaction was heated to 40° C. for 16 h. Whereupon the reaction was washed with cold 5% HCl, H$_2$O, sat. NaHCO$_3$, dried (MgSO$_4$) and concentrated in vacuo. The resulting oil was chromatographed on silica gel (EtOAc/hexane, 8/2) to afford the product as a viscous oil, 251 g (71%). $^1$H NMR (CDCl$_3$) 1.09 (s, 9H, (CH$_3$)$_3$), 1.60 (s, 3H, C5-CH$_3$), 2.05 (ddd, 1H, C2'b), 2.52 (ddd, 1H, C2'a), 3.81 (dd, 1H, C5'HH), 3.94 (dd, 1H, C5'HH), 4.08 (m, 1H, C4'H), 4.5 (m, 1H, C3'H), 4.61 (s, 2H, OCH$_2$Ph), 4.72 (s, 2H, OCH$_3$Ph), 4.80 (s, 2H, OCH$_2$O), 5.51 (s, 2H, NCH$_2$O), 6.39 (m, 1H, C1'H), 7.26–7.5 (m, 21H, CH═,ArH). Anal. Calcd. for C$_{42}$H$_{48}$N$_2$O$_7$Si: C, 69.97; H, 6.71; N, 3.89. Found: C, 69.81; H, 6.42; N, 3.91.

B. 3-Benzyloxymethyl-3'-benzyloxymethylthymidine

A solution of 3-benzyloxymethyl-3'-benzyloxymethyl-5'-O-tert-butyldiphenylsilylthymidine (20 g, 28 mmol) in THF (200 ml) was treated with tert-butyl ammonium fluoride 1 M/THF (40 ml, 40 mmol) at room temperature for 16 hrs. The solution was concentrated in vacuo and the resulting oil chromatographed on silica gel (EtOAc/hexane, 7/3→8/2) to afford the product, 10 g (75%). m.p. 83–84° C.; $^1$H NMR (CDCl$_3$), 1.92 (s, 3H, C5-CH$_3$), 2.20–2.50 (m, 3H, C2'H, C5'OH), 3.73 (dd, 1H, C5'HH), 3.89 (dd, 1H, C5'HH) 4.09 (m, 1H, C4'H), 4.49 (m, 1H, C3'H) 4.62 (s, 2H, OCH$_2$Ph), 4.70 (s, 2H, OCH$_2$Ph), 4.81 (s, 2H, OCH$_2$O), 5.49 (s, 2H, NCH$_2$O), 6.19 (t, 1H, C1'H), 7.26–7.37 (m, 5H, CH═,ArH). Anal. Calcd. for C$_{26}$H$_{30}$N$_2$O$_7$: C, 64.94; H, 6.26; N, 5.75. Found: C, 64.71; H, 6.27; N, 5.81.

C. 3-Benzyloxymethyl-3'-benzyloxymethylthymidine-5'-aldehyde

A solution of 3-benzyloxymethyl-3'-benzyloxymethylthymidine (14.5 g, 30 mmol) in DMSO (200 ml) was treated with DCC (33 g, 160 mmol) and phosphoric acid 85% (2.0 g) for 16 h. The reaction mixture was filtered and concentrated in vacuo. The resultant oil was chromatographed on silica gel (EtOAc/hexane, 7/3) to afford the product as a viscous oil, 11 g (76%). $^1$H NMR (CDCl$_3$) 1.92 (s, 3H, C5-CH$_3$), 2.20–2.52 (m, 2H, C2'H), 4.09 (m, 1H, C4'H), 4.49 (m, 1H, C3'H), 4.62 (s, 2H, NCH$_2$O), 6.28 (t, 1H, C1'H) 7.24–7.51 (M, 11H, ArH, CH═), 9.65 (s, 1H, CHO). Anal. Calcd. for C$_{26}$H$_{28}$N$_2$O$_7$: C, 64.99; H, 5.87; N, 5.83. Found: C, 64.68; H, 5.95; N, 6.01.

D. 3-Benzyloxymethyl-3'-O-benzyloxymethyl-5'-deoxy-5'-N-(octa-decylamino)thymidine A suspension of 3-benzyloxymethyl-3'-benzyloxymethylthymidine-5'-aldehyde (11 g, 23 mmol) and molecular sieve-4a (12 g) in tetrahydrofuran (250 ml) was treated with octadecylamine (8 g, 30 mmol) for 16 hrs at room temperature. The mixture was then treated with sodium cyanoborohydride (95%, 2.2 g, 33 mmol) and let stir an additional 16 hrs. The reaction mixture was filtered, concentrated in vacuo, partitioned between EtOAc/H$_2$O, separated, dried and reconcentrated in vacuo. The resultant gum was chromatographed on silica gel to afford a white powder. Recrystallization (MeOH) yielded the product, 3.8 g (23%). m.p. 60–62° C., $^1$NMR (CDCl$_3$) 0.88 (m, 3H, CH$_3$), 1.22–1.51 (m, 35H, CH$_2$), 1.93 (s, 3H, C5-CH$_3$), 2.07 (ddd, 1H, C2'a), 2.46 (ddd, 1H, C2'b), 2.51–2.94 (m, 4h, CH$_2$NH, C5'H), 4.07 (m, 1H, C4'H), 4.28 (m, 1H, C3'H), 4.62 (s, 2H, OCH$_2$Ph), 4.70 (s, 2H, OCH$_2$Pb), 4.80 (s, 2H, OCH$_2$O), 5.50 (s, 2H, NCH$_2$O), 6.28 (t, 1H, C1'H), 7.25–7.40 (m, 11H, CH═, ArH). Anal. Calcd. for C$_{44}$H$_{45}$N$_3$O$_6$: C, 72.19; H, 8.95; N, 5.74. Found: C, 71.88; H, 8.72; N, 6.01.

E. 3-Benzyloxymethyl-3'-O-benzyloxymethyl-5'-deoxy-5'-N-(octa-decylaminotrifluoroacetyl)thymidine To a solution of 3-benzyloxymethyl-3'-O-benzyloxymethyl-5'-deoxy-5'-N-(octadecylamino) thymidine (5.8 g, 79 mmol) and TEA (4.0 ml, 28 mmol) in CH$_2$H$_2$ (150 ml) was added trifluoroacetic anhydride (1.2 ml, 85 mmol). After 2h, TLC indicated completeness of reaction. The reaction was concentrated in vacuo <40° C. and coevaporated with MeOH (2×25 ml). Chromatography on silica gel (EtOAc/hexane, 1/1) afforded the product, 6.4 g (98%). $^1$H NMR (CDCl$_3$) 0.88 (m, 3H), CH$_3$), 1.25 (m, 32H, CH$_2$), 1.55 (m, 2H, CH$_2$CH$_2$NH), 1.93 (s, 3H, C5-CH$_3$), 2.10–2.51 (m, 4H, C2'H, CH$_2$NH), 3.22–3.82 (m, 2H, C5'H), 4.21 (m, 2H, C3'H, C4'H), 4.63 (s, 2H, OCH$_2$Ph), 4.70 (s, 2H, OCH$_2$Ph), 4.80 (s, 2H, OCH$_2$O), 5.50 (s, 2H, NCH$_2$O), 6.27 (t, 1H, C1'H), 7.23–7.41 (m, 11H, ArH); $^{19}$F NMR (CDCl$_3$) −74.68, (DMSO-d$_6$) −69.36. Anal. Calcd. for C$_{46}$H$_{66}$F$_3$N$_3$O$_7$: C, 66.56; H, 8.01; H, 5.06. Found: C, 66.41; H, 7.74; N, 5.29.

F. 5'-Deoxy-5-N-(octadecylaminotrifluoroacetyl)thymidine

A suspension of 3-benzyloxymethyl-3'-O-benzyloxymethyl-5'-deoxy-5-N-(octadecylaminotrifluoroacetyl)thymidine (5.5 g, 66 mmol) in methanol (250 ml), acetone (35 ml), acetic acid (0.5 ml) and palladium hydroxide/carbon (Pearlman's catalyst, 5.5 g) was hydrogenated in a paar bottle for 48 hrs at 50 psi. The catalyst was filtered off on a celite bed and the celite washed carefully with hot acetone (4×200 ml). The filtrates were combined, concentrated in vacuo to a solid and recrystallized (MeOH) to afford the product, 3.2 g (82%). m.p. 170–172° C. $^1$H NMR (DMSO-$d_6$) 88 (m, 3H, CH$_3$), 1.23 (m, 32H, CH$_2$), 1.55 (m, 2H, CH$_2$CH$_2$NH), 1.80 (s, 3H, C5-CH$_3$), 2.07 (ddd, 1H, C2'a), 2.45 (ddd, 1H, C2'b), 3.30–3.87 (m, 6H, C2'H, CH$_2$CH$_2$NH, C5'CH$_2$), 3.96 (m, 1H, C4'H), 4.15 (m, 1H, C3'H), 5.20 (m, 1H, C3'OH), 6.18 (t, 1H, C1'H), (20° C.) 7.50 (s, 1H, CH=) and 7.55 (s, 1H, CH=), (90° C.) 7.40 (s, 1H, CH=), 11.31 (s, 1H, ArNH), $^{19}$F NMR (DMSO) –69.2. Anal. Calcd. for $C_{30}H_{50}N_3O_5F_3$: C, 61.10; H, 8.54; N, 7.12. Found: C, 60.93; H, 8.51; N, 7.34.

G. 5'-deoxy-5'-N-(octadecylaminotrifluoroacetyl) thymidine-3'-O-(2-cyanoethyl N,N-diisopropyl) phosphoramidite A solution of 5'-deoxy-5'-N-(octadecylaminotrifluoroacetyl)thymidine (5.9 g, 10 mmol) in dry THF (1000 ml) was treated with bis-N,N-diisopropylaminocyanoethyl phosphite (8.0 g, mmol) and N,N-diisopropylaminotetrazolide (0.5 g, cat. amount) at rm. temp. for 16 h. The reaction was concentrated in vacuo and the residue was chromatography on silica gel (hexane/EtOAc, 6/4) to afforded the product as a foam (5.1 g). $^{19}$F NMR (CDCl$_3$) –74.65; $^{31}$P NMR (CDCL$_3$) 149.63, 149.56.

Example 9

Synthesis of Cholesterol-Oligonucleotide Conjugates Targeted to MDR1

Mammalian cells selected for resistance to certain antitumor drugs often display cross resistance to other apparently unrelated drugs and are thus said to display a multidrug resistant (MDR) phenotype (Bradley et al., *Cancer Metastasis Rev.,* 1994, 13, 223). One form of MDR is based on overexpression of one or more members of a family of membrane proteins (P-glycoproteins) which serve as ATP driven drug efflux pumps (Bradley et al., *Cancer Metastasis Rev.,* 1994, 13, 223; Gottesman et al., *J. Biol. Chem.,* 1988, 263, 12163; Roninson, *Biochem. Pharmacol.,* 1992, 43, 95). The human MDR (P-glycoprotein) gene family has two members, only one of which (P170, encoded by the MDR1 gene) appears to be responsible for resistance to cytotoxic drugs (Roninson, *Biochem. Pharmacol.,* 1992, 43, 95). In highly drug-resistant cells, P-glycoprotein message and protein levels can be many times greater than in their drug sensitive counterparts. Although MDR can be modulated by using a variety of agents that competitively inhibit P-glycoprotein mediated antitumor drug efflux (Kaji et al., *Biochem.,* 1994, 33, 5041), several of these agents have proven less than ideal in clinical trials (Chabner et al., *J. Clin. Oncol.,* 1991, 9, 4).

A. Synthesis

5'-cholesterol conjugated oligonucleotides to the MDR1 sequence (Chen et al., *Cell,* 1986, 47, 381; Genbank accession No. AF016535) were synthesized as follows. Cholesterol-3-carboxyaminohexyl-B-cyanoethyl-N,N-diisiopropyl-phosphoramidite was synthesized according to the procedure reported by MacKellar et al. (*Nucl. Acids Res.,* 1992, 20, 3411). 7.25 grams of this amidite was dissolved in anhydrous dichloromethane to bring the concentration to 0.1 M. Using this solution, ISIS 11073, a 5' cholesterol conjugated version of ISIS 5995, was synthesized by standard phosphorothioate backbone. For the cholesterol amidite coupling step, reaction time was extended to 45 minutes. This resulted in 85% coupling for the cholesterol amidite. After standard deprotection, the oligonucleotide-cholesterol conjugate was purified on a C-4 reverse-phase HPLC column (Manoharan et al., *Tetrahedron Lett.,* 1995, 36, 3651). ISIS 12064, a 5' cholesterol conjugated version of ISIS 10221, was synthesized and purified in the same manner.

Oligonucleotides comprising a 3'-O-alkylamino cholesterol moiety were prepared in the following manner. 3'-O-(propylthalimide)-cytidine was prepared essentially according to Examples 75 and 104 of WO 95/06659 (PCT/US94/10131, published Mar. 9, 1995), with the exception that N-(5-bromopentyl)phthalimide was used in place of N-(3-bromopropyl)phthalimide in order to generate 3'-O-(pentylphthlamide)-cytidine. From this compound, 5'-O-[dimethoxytrityl]-3'-O-[pentylamino]-cytidine was prepared by refluxing with hydrazine in methanol solvent. The product was purified in a silica column using 98% methanol/ammonium hydroxide 2% solvent. 5'-O-[dimethoxytrityl]-3'-O-[pentylamino]-cytidine (1.5 g) was then treated with cholesterol choloformate (1.1 g) in a mixture of 10 ml pyridine in 30 ml methylene chloride. After overnight stirring another 600 mg of cholesterol chloroformate was added and the reaction mixture was stirred for another four hours. Thin layer chromatography analysis showed reaction products at exocyclic amine and at 3'-O-pentylamine side chain. The desired product, 3'-O-[pentylamino-carbonyl-oxy cholesterol]-cytidine was obtained as the slower moving product in 43% yield.

600 mg of 3'-O-[pentylamino-carbonyl-oxy cholesteryl]-cytidine was coevaporated with pyridine (2×10 ml) and then dissolved in 10 ml of anhydrous pyridine. With external cooling using a ice bath, trimethylsilyl chloride (1 ml) was added using a syringe over a period of 5 minutes and the solution was stirred for 30 minutes. Then benzoylchloride (1 ml) was added followed by 10 ml of pyridine. The reaction mixture was stirred at room temperature overnight. 4 ml of water was added with external cooling and after 30 minutes 4 ml of concentrated ammonium hydroxide (30%) was added. Stirring was continued for another 1 hour. The reaction mixture was then evaporated and extracted between methylene chloride and water. The methylene chloride layer was evaporated to give 1.2 g of crude $N^4$-benzoyl-3-O-[pentylamino carbonyl-oxy-cholesteryl]-cytidine which was then purified in a silica column using 2.5% methanol in chloroform. The product identity and homogeneity were confirmed by $^{13}$C and $^1$H NMR spectral studies.

$N^4$-benzoyl-3-O-[pentylamino carbonyl-oxy-cholesteryl]-cytidine (450 mg) was added to 2 g of controlled pore glass (CPG, succinylated and capped), and to this mixture 200 mg of dimethylaminopyridine, 1 g of EDC [1-ethyl-3-dimethylaminopropyl)carbodiimide hydrochloride), 400 µl of triethylamine and 10 ml pyridine were added. The mixture was shaken in a wrist-action shaker overnight. The CPG was then filtered, washed with methylene chloride, methanol, methylene chloride and then ether. Then, 1.5 g of pentochlorophenol, 1 g EDC, 1 ml of triethylamine and 10 ml of pyridine were added to the CPG and the shaking was continued for 16 hours. Then 3 ml of pyperidine was added and shaking continued for 5 minutes. The CPG was filtered, washed and dried. 9 mg of the derivatized CPG was treated with 25 ml of 2% dichloroacetic acid in methylenechloride and the loading was determined to be 27.16 µm ol/g using colorimetric assays. ISIS 13328 (GATCC*, where "C*" indicates the 3'-O-alkylamino cholesterol cytidine residue; used for NMR studies), ISIS 13329, ISIS 13330, ISIS 13331 and ISIS 13332 were synthesized using this CPG. Other 3'-O-alkylamino cholesterol derivatives, and 5'-fluorescein isothiocyanate (FITC)

conjugates of the oligonucleotides of the invention are prepared in like manner using the methods disclosed in WO 95/06659 and the above protocols.

TABLE 9

Phouphorothioate oligonucleotides targeted to MDR1

| ISIS # | SEQUENCES* (DESCRIPTION) | SEQ ID NO: | TARGET REGION |
|---|---|---|---|
| 5990 | GAG-CCG-CTA-CTC-GAA-TGA-GC | 27 | 5' Untranslated |
| 5993 | GTT-CTG-GCT-TCC-GTT-GCA-CC | 29 | 5' Untranslated |
| 5994 | CCC-GGC-CCG-GAT-TGA-CTG-AA | 29 | 5' Untranslated |
| 5995 | CCA-TCC-CGA-CCT-CGC-GCT-CC | 30 | Start codon |
| 10440 | CGG-TCC-CCT-TCA-AGA-TCC-AT | 31 | Start codon |
| 10441 | CCC-CTT-CM-GAT-CCA-TCC-CG | 32 | Start codon |
| 10442 | CAA-GAT-CCA-TCC-CGA-CCT-CG | 33 | Start codon |
| 5996 | CCT-GGT-CAT-GTC-TTC-CTC-CA | 34 | ORF** (splice junction) |
| 5997 | CTT-TGC-CCA-GAC-AGC-AGC-TO | 35 | ORF (splice junction) |
| 5998 | GTT-CAC-TGG-CGC-TTT-GTT-CC | 36 | ORF / Stop codon |
| 5999 | TGA-ACT-TGA-CTG-AGG-AAA-TG | 37 | 3' Untranslated |
| 6002 | CTT-GGA-AGA-GCC-GCT-ACT-CG | 38 | 5' Cap region |
| 6003 | GCC-CCT-ACT-CCA-ATG-AGC-GC | 39 | 5' Cap region |
| 6004 | GGA-AGA-GCC-GCT-ACT-CGA-AT | 40 | 3' Untranslated |
| 6005 | CTC-TGT-TCC-TTT-AAT-TAC-GA | 41 | 3' Untranslated |
| 6006 | TCC-ACT-TGA-TCA-TGT-CTC-TC | 42 | 3' Untranslated |
| 6007 | CTA-TGA-TTT-CTC-TCC-ACT-TG | 43 | 3' Untranslated |
| 6010 | GGC-AGT-CAG-TTA-CAG-TCC-M | 44 | 3' Untranslated |
| 6011 | TTT-TAG-CAA-GGC-AGT-CAG-TT | 45 | 3' Untranslated |
| 6012 | TGC-AAA-CAT-TTC-AAT-ACT-TT | 46 | 3' Untranslated |
| 6013 | AAG-TTT-AGT-TTT-ATT-ATA-GA | 47 | 3' Untranslated |
| 10221 | CAC-CAC-CCC-CCT-CGC-TGG-TC | 48 | Scrambled * 5995 |
| 10222 | CTC-CCG-CAC-ATC-TCC-GCG-CC | 49 | Scrambled * 5995 |
| 11432 | GCC-ACC-GTC-TGC-CCA-CTC-TG | 50 | ORF |
| 11433 | GGC-ACG-TGC-AAT-GGC-GAT-CC | 51 | ORF |
| 1434 | CGG-AGC-CGC-TTG-GTG-AGG-AT | 52 | ORP |
| 1435 | AGC-AGC-ATC-ATT-GGC-GAG-CC | 53 | ORP |
| 11436 | CGG-CCA-TGG-CAC-CAA-AGA-CA | 54 | ORF |
| 11437 | TGA-ACT-GAC-TTG-CCC-CAC-GG | 55 | ORF |
| 11438 | GGG-ATG-TCC-GGT-CGG-CTG-GG | 56 | ORF |
| 11439 | TGC-CCA-CCA-GAG-CCA-GCG-TC | 57 | ORF |
| 11440 | ATG-CCC-AGG-TGT-GCT-CGG-AG | 58 | |
| 11441 | GCC-TCC-TTT-GCT-GCC-CTC-AC | 59 | ORF |
| 11442 | TGG-TGG-ACA-GGC-GGT-GAG-CA | 60 | ORP |
| 10443 | 2'-o-Methyl analog of # 5995 | 30 | Start codon |
| 11073 | 5'-Cholesterol analog of # 5995 | 30 | Start codon |
| 12064 | 5'-Cholesterol analog of # 10221 | 48 | Scrambled control for # 11073 |
| 13758 | 2'-O-Methoxyethoxy analog of # 5995 | 30 | Start codon |
| 13753 | 2'-Methoxyethoxy analog of # 10221 | 48 | Scrambled control far # 13758 |
| 13755 | 2'-Methoxyethoxy analog of # 5998 | 36 | ORF / Stop codon |
| 14429 | 2'-o-Methoxyethoxy CTT-ACC-CCC-TTG-TGT-TGC-TG | 63 | Scrambled control for # 13755 |
| 13756 | 2'-Methoxyethoxy analog of # 6011 | 45 | 3' Untranslated |
| 13757 | 2'-Methoxyethoxy analog of # 6006 | 42 | 3' Untranslated |
| 12065 | Analog of # 5995 comprising FITC at 3' end | 30 | Start codon |
| 13329 | Analog of # 5995 comprising 3'-O-pentylamino cholesterol | 30 | Start codon |
| 13330 | Analog of # 5995 w/ 5' -C6 amino linker & 3'-O-pentylamino cholesterol | 30 | Start codon |
| 13331 | Analog of # 5995 comprising 5 ' FITC & 3'-O-pentylamino cholesterol | 30 | Start codon |
| 13332 | Analog of # 10221 comprising 3'-O-pentylamino cholesterol | 48 | Scrambled control |
| 13409 | Analog of # 5995 comprising 5'-C6 amino linker | 30 | Start codon |
| 13434 | Analog of # 5995 comprising FITC at 5' end | 30 | Start codon |

*From left to right, sequences are written from 5' to 3'.
All oligonucleotides contain fully substituted phosphorothioate backbones unless otherwise indicated.
**ORF, open reading frame.

B. Oligonucleotide-mediated inhibition of MDR1 mRNA

NIH 3T3 cells transfected with a plasmid containing the human MDR1 gene (pSK1 MDR) have been previously described (Kane et al., Gene, 1989, 84, 439). These cells have proven to be useful models for the study of multi-drug resistance phenomena. Cells were grown in DMEM media containing 10% fetal bovine serum (FBS) and 60 ng/ml colchicine in an atmosphere of 95% air, 5% $CO_2$.

In most cases, the multi-drug resistant 3T3 cells were exposed to oligonucleotides administered as a complex with cationic liposomes (Lipofectin$^R$). However, all studies with cholesterol conjugated oligonucleotides were performed in the absence of cationic liposomes. Cells were treated with oligonucleotides according to the following procedure. Cells were grown in 162 mm flasks. When 95% confluency was reached, cells were seeded onto 100 mm dishes at $5\times10^5$/dish in 10 ml of 10% FBS/DMEM and incubated for 24 hours. At this stage, the cells were washed two times with phosphate buffered saline (PBS) and then 8 ml of serum-free medium was added. For phosphorothioate oligonucleotides, 20 ug/ml LIPOFECTIN$^R$ (GIBCO/BRL, Gaithersburg, Md.) and various amounts of oligonucleotide were mixed, pre-incubated at room temperature for 30 minutes, and then incubated with the cells at 37° C. in a $CO_2$ incubator for various periods. Similar methods were used for 2'-O-methyl phosphorothioate oligonucleotides. For treatments with cholesterol-phosphorothioate oligonucleotides, the compounds were simply added to the cells in serum free medium (in the absence of LIPOFECTIN$^R$) with antibiotics and incubated at 37° C. in a $CO_2$ incubator for various periods. The cytotoxicity of the various treatments used in the oligonucleotide experiments were evaluated in preliminary experiments by using a vital dye assay. Unless otherwise noted, conditions were chosen such that there was usually less than a 10% difference in the number of viable cells in samples treated with oligonucleotides versus control samples maintained in medium alone. The MDR-3T3 cells maintained a high level of viability during extended incubation in serum free medium, although cell division was largely suppressed.

To measure MDR1 mRNA expression by Northern blotting, total cellular RNA was isolated by lysis in 4 M guanidium isothiocyanate followed by a cesium chloride gradient, and the RNA was resolved on 1.2% agarose gels containing 1.2% formaldehyde and transferred to nitrocellulose membranes (Dean et al., J. Biol. Chem., 1994, 269, 16416). The blots were hybridized with a $^{32}P$ radiolabeled human MDR1 cDNA probe. The MDR1 cDNA probe was isolated by performing a polymerase chain reaction on the pSK1 MDR plasmid, as described previously (Alahari et al., *Nucl. Acids Res.*, 1993, 21, 4079). The following oligonucleotide primers were used for PCR:

5'-GGATCTTGAAGGGGACCGCAATGGAGGAGC (SEQ ID NO: 61), and
5'-GTCCAACACTAAAAGCCCCAATTAATACAG (SEQ ID NO: 62).

The resulting fragment was checked on an agarose gel and was radiolabeled with $^{32}$P-dCTP using a commercially available random primer labeling kit (Amersham, Arlington Heights, Ill.) according to the manufacturer's instructions. The filters were hybridized overnight in hybridization buffer (25 mM KPO$_4$, pH 7.4; 5×SSC; 5×Denhardt's solution, 100 ug/ml Salmon sperm DNA and 50% formamide) (Alahari et al., *Nucl. Acids Res.*, 1993, 21, 4079). This was followed by two washes with 1×SSC, 0.1% SDS and two washes with 0.25×SSC, 0.1% SDS. Hybridizing bands were visualized by exposure to X-OMAT AR film and quantitated using a PhosphorImager™ (Molecular Dynamics, Sunnyvale, Calif.). To confirm equal loading of RNA, the blots were stripped and reprobed with a $^{32}$P-labeled beta-actin probe (Clontech, Palo Alto, Calif.).

1. Identification of an antisense oligonucleotide that specifically reduces MDR1 message expression RNA isolated from MDR 3T3 cells was probed with a 1.0 kb PCR-based MDR1 probe; this revealed a transcript of 4.4 kb. In initial experiments, the MDR 3T3 cells were exposed to 1.0 µm concentrations of several different antisense oligonucleotides, or control oligonucleotides, in the presence of 20 ug/ml LIPOFECTIN$^R$ for 24 hours. One oligonucleotide, ISIS 5995, which was targeted to a region overlapping the AUG codon, caused about 50% reduction in MDR1 message levels (Table 10). Oligonucleotides ISIS 10221 and ISIS 10222 have the same base composition as ISIS 5995, but are "scrambled" sequences that were used as specificity controls. NIH 3T3 cells transfected with pSK1 MDR plasmid were grown to 90% confluence and treated with oligonucleotide (1 µm) for 24 hours in the presence of Lipofectin$^R$ in serum free medium. Total RNA was isolated and fractionated on agarose formaldehyde gels and blotted onto nitrocellulose membranes. These membranes were probed with a $^{32}$P radiolabeled 1.0 kb MDR1 cDNA, and then stripped and reprobed with a $^{32}$P radiolabeled beta-actin cDNA probe to confirm equal loading of RNA, allowing the levels of MDR1 transcripts to be normalized with regard to the beta-actin bands. Transcript levels were quantitated using a PHOSPHORIMAGER™ (Molecular Dynamics, Sunnyvale, Calif.); the values are expressed in arbitrary units (the beta-actin transcripts were essentially constant).

TABLE 10

MODULATION OF MDR1 MRNA BY ANTISENSE OLIGONUCLEOTIDES

| ISIS NO. | SEQ ID NO: | MDR1 mRNA Level (arbitrary units) | % Control |
|---|---|---|---|
| None* | — | 473,913 | 100% |
| LIPOFECTIN$^R$ | — | 430,435 | 91% |
| 5990 | 27 | 4431478 | 94% |
| 5995 | 30 | 226,087 | 48% |
| 10221 | 48 | 456,522 | 96% |
| 10222 | 49 | 406,522 | 86% |

*Control = untreated cells

This experiment was repeated several times, and the MDR1 and beta-actin bands on non-saturated autoradiograms were compared by laser densitometry. The MDR1/beta-actin ratios for the ISIS 5995 and ISIS 10221 oligonucleotides were 0.49 and 1.01, respectively, indicating specific inhibition of MDR1 message levels by ISIS 5995.

2. Time course of inhibition of MDR1 message levels by oligonucleotide ISIS 5995

In order to evaluate the time course of ISIS 5995-mediated MDR1 modulation, transfected cells were treated with 1 µm ISIS 5995, or 1 µm ISIS 10221, for 24, 48 and 72 hours. MDR1 and beta-actin RNA levels were examined as described above. Maximum specific reduction of MDR1 mRNA was observed after 24 hours treatment of cells with ISIS 5995; longer treatment did not result in lower mRNA levels. With these unmodified oligonucleotides, reduction of MDR1 mRNA levels was attained only when oligonucleotide treatment was performed in serum free medium, and when cationic liposomes were used. This result is consistent with previous observations on antisense actions of phosphorothioate oligonucleotides in cell culture (Bennett et al., *Mol. Pharm.*, 1992, 41, 1023; Manoharan et al., *Tetrahedron Lett.*, 1995, 36, 3651). Multiple treatments with ISIS 5995 oligonucleotide did not cause any greater specific reduction in MDR1 message levels than a single treatment, while greater cytotoxicity was observed. The reduction in MDR1 mRNA expression was reversible, since, after 24 hours exposure to ISIS 5995, cells returned to culture medium without oligonucleotide demonstrated normal levels of MDR1 mRNA within 24 hours.

3. Concentration dependence of MDR1 message reduction

Treatment of multi-drug resistant 3T3 cells with oligonucleotide ISIS 5995 resulted in a concentration-dependent inhibition of MDR1 message (FIG. 1). Some reduction in message levels was observed with concentrations as low as 100 nM. Maximal specific effects were observed at approximately 1.0 µm; this entailed an approximately 60% reduction in MDR1 message. Use of higher concentrations of oligonucleotides (5–10 µm) with Lipofectin$^R$ resulted in greater non-specific effects, i.e., reduced beta-actin message levels and increased cytotoxicity, which were observed with both ISIS 5995 and ISIS 10221 (the scrambled control).

C. Oligonucleotide-mediated inhibition of P-glycoprotein

Transfected MDR NIH 3T3 cells were grown and treated with oligonucleotides as described in Example (9)(B). In order to measure P-glycoprotein expression by Western blotting, cells were seeded in 60 mm dishes at 1.2×10$^6$ per dish and incubated for 24 hours in serum containing medium. The cells were treated with the oligomers for various times in serum free medium as described above. Cells were then extracted in lysis buffer (20 mM Tris, pH 7.5, 2 mM EDTA, 500 mM EGTA, 2 mM PMSF, 1 mM DTT, aprotonin (10 ug/ml), 0.5% Triton-X) and sonicated briefly. The lysate was spun in a microfuge tube for 20 minutes at 4° C. and the resulting supernatant was checked for protein content. Equal amounts of protein (usually 20 ug) were mixed with SDS sample buffer and boiled. Protein samples were separated by 8% SDS PAGE and the resolved proteins were electrophoretically transferred onto polyvinylidene fluoride membranes (Millipore, Bedford, Mass.). The membranes were blocked (with 3% BSA, 2% non fat dry milk in PBS) and then treated with 2 ug/ml C219 anti-P-glycoprotein antibody (Signet, Dedham, Mass.). After washing three times with 0.1% Tween 20, the membranes were incubated with rabbit anti-mouse antibody (Cappel, Durham, N.C.). Immunoreactive proteins were visualized either by ECL (Enhanced Chemiluminescence, Amersham, Arlington Heights, Ill.) or with $^{125}$I secondary antibodies.

Expression of the P-glycoprotein was reduced upon treatment of the multidrug resistant 3T3 cells with the ISIS 5995 oligomer, consistent with the Northern blot analyses of mRNA levels. In the Western assays, P-glycoprotein was reduced at least 80% by treatment with ISIS 5995 and about 50% by ISIS 10440. In contrast, scrambled control oligomer ISIS 10221 did not reduce P-glycoprotein expression. The decrease in P-glycoprotein expression was minimal after 24 hours, readily detectable by 48 hours, and reached a maximum only after 72 hours exposure. Thus, effects at the protein level lag behind the observed reduction in message levels. This observation is consistent with the fact that the P-glycoprotein is quite stable and normally turns over rather slowly with a $t^{1/2}$ of 48–72 hours (Richert et al., *Biochem.*, 1988, 28, 7607).

D. Effects of a cholesterol derivative of oligonucleotide 5995 on MDR1 message levels and P-glycoprotein expression A 5'-cholesterol derivative of ISIS 5995 (ISIS 11073), as well as a 5'-cholesterol derivative of the scrambled control oligonucleotide ISIS 10221 (ISIS 12064), were synthesized and their effects on MDR1 message and P-glycoprotein levels were examined. As is explained below, 3'-cholesterol derivitives were also prepared and tested.

Transfected MDR NIH 3T3 cells were grown and treated with oligonucleotides as described in Example (9)(B). MDR1 mRNA expression was measured by Northern blotting as described in Example (9)(C). In order to measure cell surface P-glycoprotein levels by flow cytometry, cells were seeded in 60 mm dishes at $1.2 \times 10^6$/plate in 5 ml of medium, grown for one day in 10% FBS/DMEM, and exposed to the oligomers in serum free medium. After treatment with the oligonucleotides, cells were washed twice in PBS, 0.25 ml of pancreatin was added to remove cells from the plate, and the dispersed cells were resuspended in 10% FBS/DMEM and incubated at 37° C. for 2 hours. After the incubation, cells were washed in PBS, and 50 µl of 20 ug/ml MRK16 anti-P-glycoprotein antibody (Kamiya, Thousand Oaks, Calif.) was added (Ishida et al., *Jpn. J. Cancer Res.*, 1989, 80, 1006). This mixture was incubated for 45 minutes on ice and cells were washed three times in 10% FBS/PBS. Cells were then incubated for 30 minutes with 20 µl of ten times diluted secondary antibody, a R-phycoerythrin (R-PE) conjugated goat anti-mouse IgG (Sigma, St. Louis, Mo.). After the incubation, cells were washed two times in 10% FBS/PBS. Finally, the cells were resuspended in 500 µl of PBS. The level of R-PE fluorescence in viable cells (as determined by light scatter) was wuantitated using the Cicero software application (Cytomation, Fort Collins, Colo.) on a Becton Dickinson flow cytometer.

Table 11 shows the effect of cholesterol-conjugated phosphothioate oligonucleotides on MDR1 mRNA expression. MDR-3T3 cells were treated with various concentrations of oligonucleotides ISIS 11073 (5'-cholesterol 5995) or ISIS 12064 (5'-cholesterol 10221; scrambled control) for 24 hours in serum free medium. Total RNA was isolated, fractionated and probed with a MDR1 cDNA fragment; the same blot was stripped and reprobed with a beta-actin probe. The results were quantitated using a PHOSPHORIM-AGER™; the ratio of MDR1 to beta-actin message is indicated in the table. As shown in Table 11, treatment with concentrations of ISIS 11073 (cholesterol 5995) in the 250 nM to 2.5 µm range, resulted in a specific decrease in levels of MDR1 message. It is important to note that at least about 60% inhibition of MDR1 mRNA expression was attained with ISIS 11073 without the use of cationic liposomes.

TABLE 11

MODULATION OF MDR1 MRNA BY CHOLESTEROL-CONJUGATED ANTISENSE OLIGONUCLEOTIDES

| ISIS No. | SEQ ID NO: | Conc. | Ratio of MDR1 mRNA to beta-actin mRNA |
|---|---|---|---|
| None* | — | — | 1.00 |
| 12064 | 48 | 2.5 µM | 1.10 |
| 11073 | 30 | 250 nM | 0.48 |
| 11073 | 30 | 500 nM | 0.38 |
| 11073 | 30 | 1.0 uM | 0.45 |
| 11073 | 30 | 2.S uM | 0.59 |

*Control = untreated cells

Lane 1, untreated cells; lane 2, cells treated with 2.5 µm 5' ISIS 12064; lanes 3–6, cells treated with ISIS 11073 at concentrations of 250 nM, 500 nM, 1.0 µm and 2.5 µm, respectively.

To observe the effects of the 5'-cholesterol 5995 (ISIS 11073) oligonucleotide on the expression of P-glycoprotein at the cell surface, immunofluorescent staining and flow cytometry were utilized. Treatment of multidrug resistant 3T3 cells with increasing concentrations of ISIS 11073 over the range of 0.5–2.5 um resulted in a progressive reduction in surface expression of P-glycoprotein to about 40% of control levels. Some non-specific reduction of P-glycoprotein expression was also observed with the scrambled control oligomer (5'-cholesterol 10221, ISIS 12064), but the effect of the antisense compound was greater at all concentrations tested. In a parallel experiment, the effect of 1 µm ISIS 5995 or ISIS 10221 administered with LIPOFECTIN$^R$ on P-glcoprotein surface expression was examined. The test concentrations of antisense (ISIS 5995) or scrambled 5'-cholesterol (ISIS 10221) phosphorothioate oligonucleotides, administered with LIPOFECTIN$^R$, were less effective than an equivalent concentration of the cholesterol-conjugated analogs. Thus, the cholesterol phosphorothioate antisense compound given along is at least as effective as the phosphorothioate antisense compound administered with cationic liposomes. Moreover, the cholesterol oligonucleotides showed less experiment-to-experiment variation than did the standard phosphorothioate oligonucleotides when administered with cationic lipids.

To observe the effects of the 3'-cholesterol 5995 oligonucleotide (ISIS 13329) on the expression of P-glycoprotein at the cell surface, immunofluorescent staining and flow cytometry were utilized as described above. Treatment of multidrug resistant 3T3 cells with increasing concentrations of ISIS 13329 over the range of 0.5–2.5 µm resulted in a progressive reduction in surface expression of P-glycoprotein to about 50% of control levels. In a parallel experiment, the effect of 1 µm ISIS 5995 or ISIS 13332 administered with LIPOFECTIN$^R$ on P-glycoprotein surface expression was examined. The test concentrations of antisense (ISIS 5995) or scrambled 3'-cholesterol (ISIS 13332) phosphorothioate oligonucleotides administered with LIPOFECTIN$^R$, were less effective than an equivalent concentration of the cholesterol-conjugated analogs. Thus, the cholesterol phosphorothioate antisense compound given alone is at least as effective as the phosphorothioate antisense compound administered with cationic liposomes. However, the cholesterol oligonucleotides showed less experiment-to-experiment variation than did the standard phosphorothioate oligonucleotides when administered with cationic lipids and are thus preferred. A further advantage of the 3'-cholesterol oligonucleotide is stability to 3'-exonucleases.

E. Effects of oligonucleotides on Rh 123 accumulation

Rhodamine 123 is fluorescent dye that is a substrate for P-glycoprotein and is rapidly transported out of multi-drug resistant cells. Thus, Rh 123 uptake can be employed as a simple and convenient way of assessing the impact of various treatments on the multi-drug resistance phenotype. In order to measure Rhodamine 123 uptake by flow cytometry, the procedure described by Twentyman et al. (*Eur. J. Cancer*, 1994, 30, 1360) was followed with minor changes. Briefly, $7.5 \times 10^5$ cells were seeded on 6 well plates, incubated for one day, and treated with oligomers as described above. Cells were removed with pancreatin and resuspended in 10% FBS/DMEM. Rhodamine 123 (Sigma, St. Louis, Mo.) was dissolved in water, added to a final concentration of 1.0 ug/ml; 500 µl samples were taken at several points, washed with medium once, and resuspended in 500 µl of media. Viable cells were analyzed for the accumulation of Rhodamine 123 on a Becton Dickinson flow cytometer using Cicero software.

Figure 2:
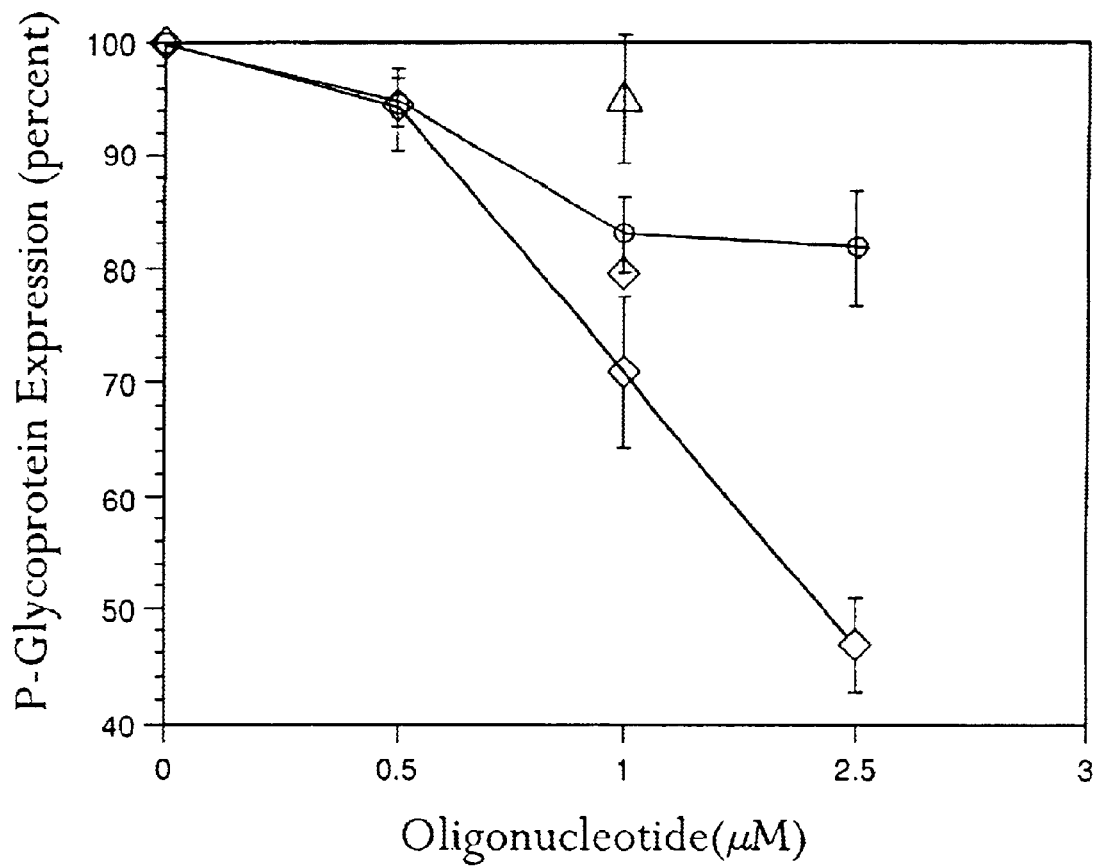
FIG. 2 shows the effect of cholesterol-conjugated phosphothioate oligonucleotides on P-glycoprotein surface expression. MDR 3T3 cells were treated with various concentrations of oligonucleotides ISIS 11073 (5'-cholesterol 5995), or ISIS 12064 (5'-cholesterol 10221; scrambled control) for 48 hours in serum free medium. The cells were recovered and stained with an anti-P-glycoprotein monoclonal antibody directed against a surface epitope, followed by a phycoerythrin-conjugated second antibody. The level of cell surface fluorescence in viable cells was quantitated using a flow cytometer; light scatter parameters were set so as to exclude non-viable cells. A parallel experiment was done with cells treated with oligonucleotides ISIS 5995 and ISIS 10221 at 1 μm, in the presence of LIPOFECTIN$^R$. The data are presented as percent inhibition of P-glycoprotein expression, with the 100% level taken as that for untreated MDR 3T3 cells. The results represent means and standard errors for 6 determinations. Filled diamonds, ISIS 11073 (cholesterol-conjugated ISIS 5995); filled circles, ISIS 12064 (cholesterol-conjugated ISIS 10221; scrambled control); open diamonds, ISIS 5995; open triangles, ISIS 10221.
Figure 3:
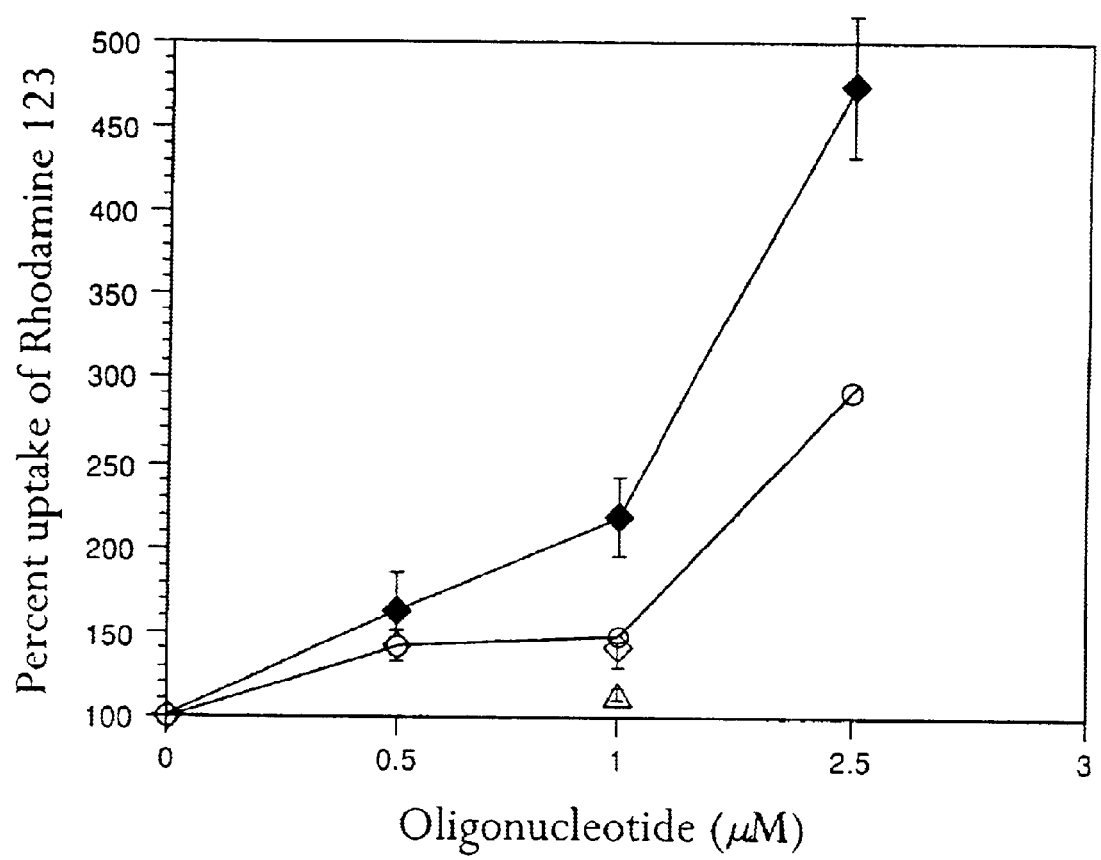
FIG. 3 shows the results of experiments in which cells treated as described in FIG. 2 were analyzed for Rhodamine 123 uptake. Subsequent to oligonucleotide treatment the cells were washed and then exposed to 1 ug/ml Rh 123 in serum free medium at 37° C. After 1 hour the cells were washed and the amount of Rh 123 accumulated by viable cells was quantitated using a flow cytometer. The results represent means and standard errors for 3 determinations. Symbols, as in FIG. 2.

Treatment of multi-drug resistant 3T3 cells with increasing concentrations of ISIS 11073 (cholesterol-conjugated ISIS 5995) resulted in a progressive decrease in P-glycoprotein expression (FIG. 2) that paralleled an increase in Rh 123 accumulation (FIG. 3). As in the case of P-glycoprotein expression, some non-specific effect was also observed with the scrambled control oligomer (ISIS 12064; cholesterol-conjugated ISIS 10221); however, the effect of the antisense compound was significantly greater.

Example 10

Uptake and Intracellular Distribution of Cholesterol-Conjugated Oligonucleotides As Example 9 demonstrates, experiments indicated that the 3'-cholesterol derivative of ISIS 5995 (ISIS 13329) had an equivalent effect on P-glycoprotein expression as 5'-cholesterol 5995 (ISIS 11073). To determine the rate of cellular uptake and intracellular distribution of MDR1 antisense oligonucleotides, the following experiments were performed with 5'-FITC, 3'-cholesterol oligonucleotides.

The cellular accumulation of FITC labeled oligonucleotides was quantitated by flow cytometry. The cell uptake and intracellular distribution was visualized on a cell-by-cell basis using digitized fluorescence microscopy, essentially as described previously (Shoji et al., *Nucl. Acids Res.*, 1991, 19, 5543), except that a confocal microscope system was used. Intracellular fluorescence was visualized by taking optical sections through the cell body; a section approximately half way between the top surface of the cells and the surface of the cover slip was examined in each case. Phase contrast images of the same cells were also obtained. A Nikon Fluor 40/1.3 Oil Ph4DL objective was used, with Comos software controlling a Biorad MRC600 scanner/laser. In digitized images, gain and black level settings were optimized on cells treated with free FITC 5995 oligomer and were unchanged thererafter.

Incubation conditions for the flow cytometry and confocal microscopy experiments were as follows. MDR 3T3 cells were treated with 1 µm ISIS 13331 (5'-FITC, 3'-cholesterol 5995), or with 1 µm ISIS 13434 (5'-FITC 5995) with or without LIPOFECTIN$^R$, for either 2 hours (FIG. 4) or 18 hours (FIG. 5) in serum free medium at 37° C. Cells were harvested and the fluorescence profiles were determined using a flow cytometer; light scatter parameters were set so as to exclude non-viable cells. In the case of the 18 hour treatment with LIPOFECTIN$^R$ there were some cells with very high levels (above $10^4$ units) of fluorescence; these were accumulated in one channel and are shown as a vertical line at the right hand margin of the plot (FIG. 5). Cells plated on glass coverslips were treated as above for 18 hour and then examined by confocal microscopy as described above.

Figure 4:
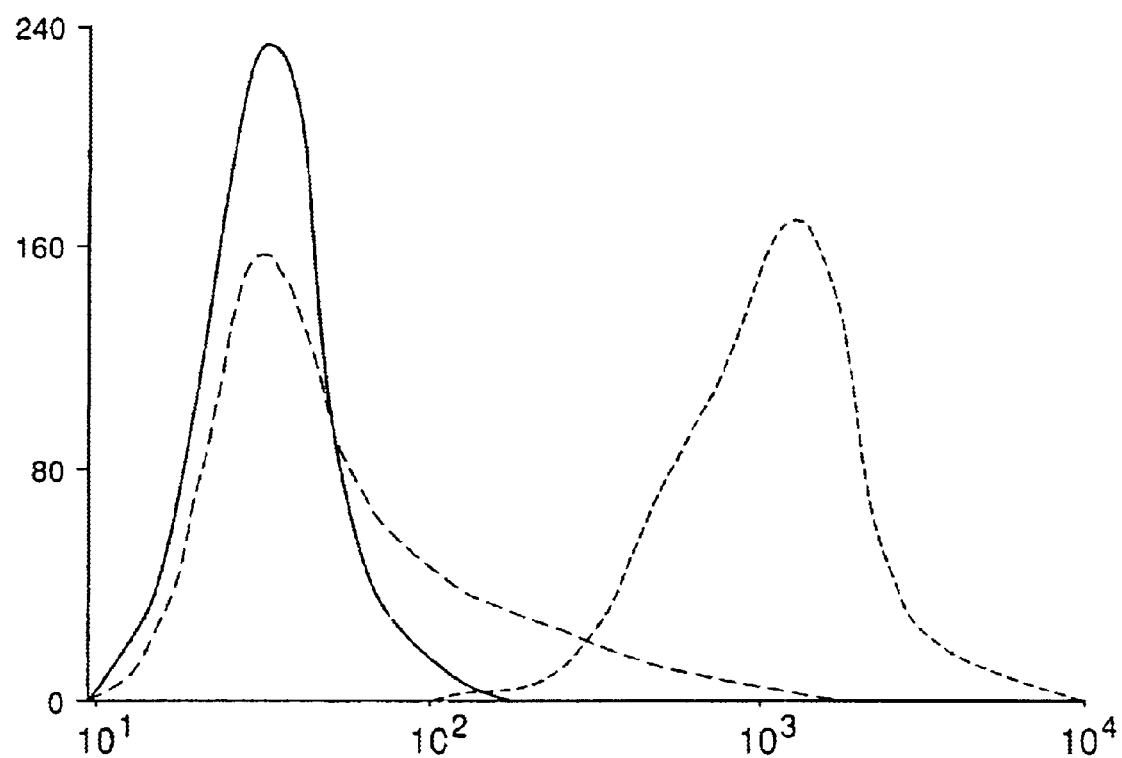
FIG. 4 shows the uptake and intracellular distribution of effect of cholesterol-conjugated phosphothioate MDR1 oligonucleotides. MDR-3T3 cells were treated with 1 μm ISIS 13331 (5'-FITC, 3'-cholesterol 5995), or with 1 μm ISIS 13434 (5'-FITC 5995) for 2 hours in serum free medium at 37° C. Cells were harvested and the fluorescence profiles were determined using a flow cytometer; light scatter parameters were set so as to exclude non-viable cells. Solid line, free ISIS 13434 (5'-FITC 5995); dashed line, ISIS 13434 with Lipofectin$^R$; dotted line, ISIS 13331 (5'-FITC, 3'-cholesterol 5995).
Figure 5:
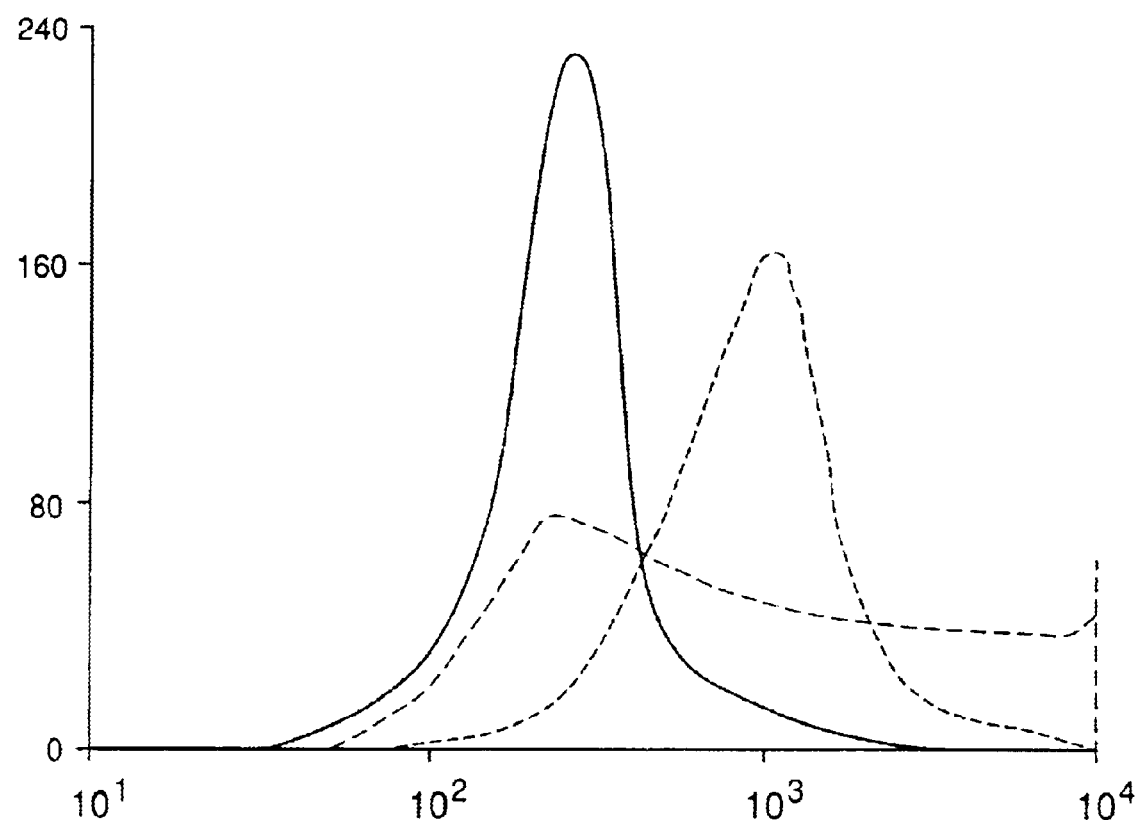
FIG. 5 shows the uptake and intracellular distribution of effect of cholesterol-conjugated phosphothioate MDR1 oligonucleotides of cells treated as in FIG. 4 but for 18 hours instead of 2 hours. The 18 hour treatment with LIPOFECTIN$^R$ resulted in some cells with very high levels (above $10^4$ units) of fluorescence; these were accumulated in one channel and are shown as a vertical line at the right hand margin of the plot.

As seen in FIG. 4, during a 2 hour incubation period the cholesterol conjugated oligonucleotide (ISIS 13331) was rapidly accumulated by cells, while both free ISIS 13434, and ISIS 13434 complexed with LIPOFECTIN$^R$, accumulated to a far lesser degree. The cellular accumulation of the 3'-cholesterol conjugated 5995 (ISIS 13331) was approximately 40 fold greater than ISIS 13434 at 2 hours. After overnight incubation (FIG. 5), the free ISIS 13434 still displayed significantly less cell accumulation than ISIS 13331. The LIPOFECTIN$^R$ complexed ISIS 13434 displayed substantial, but very heterogeneous, cell uptake after overnight incubation. Based on previous experience with stability of phosphorothioates (Akhtar et al., *Trends in Cell Biology*, 1992, 2, 139) it is believed that most of the fluorescence accumulated represents FITC-conjugated oligonucleotide rather than free FITC.

Confocal microscopic images essentially confirmed and extended the flow cytometry observations. Very little intracellular accumulation was seen with ISIS 13434. The cells treated with ISIS 13434 complexed with Lipofectin$^R$ showed extensive, but very heterogeneous, cellular uptake, with some cells heavily stained and others essentially blank; there was also a background of LIPOFECTIN$^R$ particles plus associated oligonucleotide bound to the cover slip. Some of the cells treated with Lipofectin$^R$ showed nuclear accumulation of the fluorescence. The cells treated with ISIS 13331 (5'-FITC, 3'-cholesterol) oligonucleotide uniformly displayed extensive fluorescence in both the cytoplasm and nucleus. These observations demonstrate that the cholesterol conjugation has enhanced the rapidity, amount, and uniformity of cellular uptake of the oligonucleotide, and leads to substantial cytoplasmic and nuclear accumulation.

Example 11

Effects of 3'-Cholesterol, 2'-Methoxyethoxy Gapmer Oligonucleotides on P-glycoprotein Expression A. Effects of 2'-methoxyethoxyoligonucleotides on P-glycoprotein expression 2'-Methoxyethoxy derivatives of ISIS 5995 (ISIS 13758, targeted to the start codon region of MDR1), ISIS 5998 (ISIS 13755, targeted to the stop codon region of MDR1) and ISIS 10221 (ISIS 13753, a scrambled control for ISIS 5995) were prepared and examined for their ability to modulate P-glycoprotein expression. To assay activity, experiments were conducted essentially as described for FIG. 2 (Example 9). These oligonucleotides are "chimeric" or "gapped" compounds having 2'-methoxyethoxy modifications on the five 5' and five 3' nucleotides, wherein each methoxyethoxy cytosine is a 5-methyl cytosine, and phosphorothioate deoxynucleotides in the center ten nucleotides of the molecules. This configuration allows the oligonucleotide to have nuclease-resistant "wings" while retaining a central portion that supports the action of RNase H.

Figure 6:
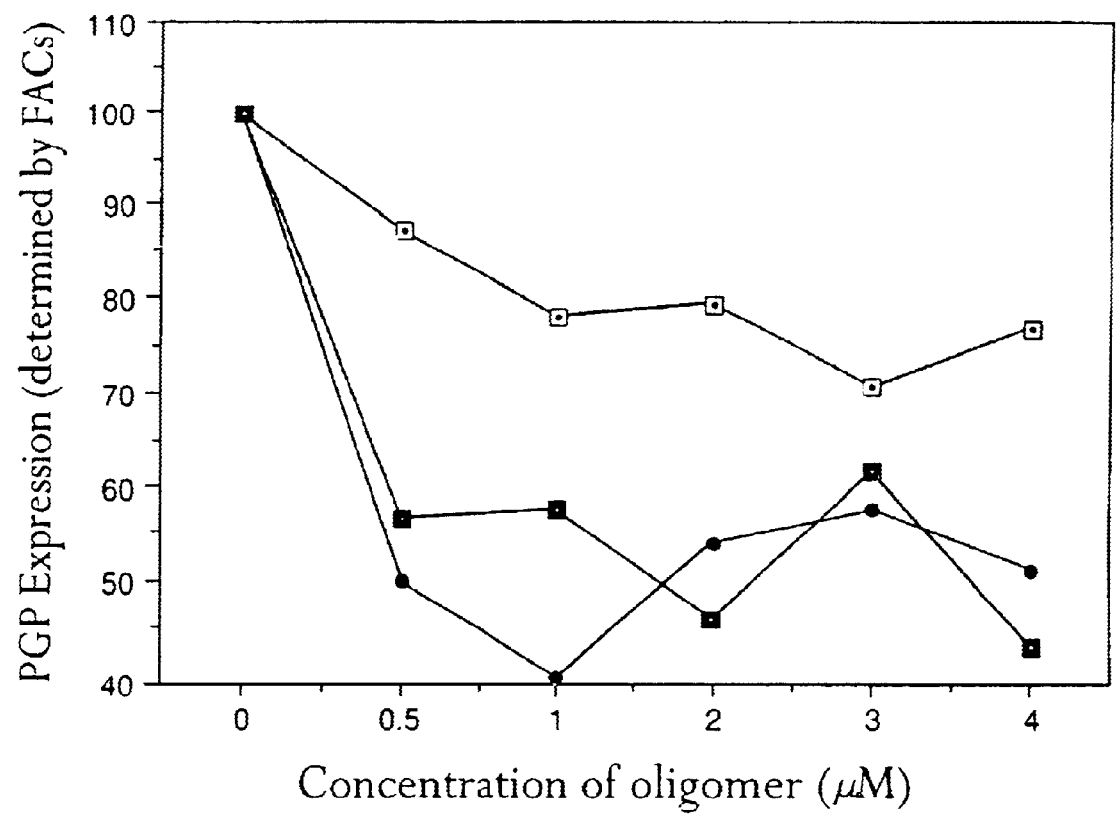
FIG. 6 shows modulation of P-glycoprotein (PGP) expression by 2'-methoxyethoxy oligonucleotides as determined by flow cytometry essentially as described in FIG. 2. Open boxes, ISIS 13753 (2'-methoxyethoxy derivative of ISIS 10221); closed circles, ISIS 13755 (2'-methoxyethoxy derivative of ISIS 5998); closed boxes, ISIS 13758 (2'-methoxyethoxy derivative of ISIS 5995).

As is shown in FIG. 6, the 2'-methoxyethoxy derivative of ISIS 5995 (ISIS 13758) exhibited an enhanced ability to inhibit P-glycoprotein expression (compare with FIG. 2). Furthermore, ISIS 13755, the 2'-methoxyethoxy derivative of ISIS 5998, exhibited significant activity in these assays, even though the parent compound had an unpromising effect on MDR1 mRNA expression (Example 9(B)). These results are an example of the enhanced efficacy of oligonucleotide activity that can be achieved by incorporating methoxyethoxy modifications into oligonucleotides. Although not wishing to be bound by any particular theory, these results are believed to demonstrate the enhanced activity resulting from the ability of methoxyethoxy modifications to render oligonucleotides resistant to many nucleases, as well as their ability to increase the hybridization affinity of oligonucleotides to their targeted nucleic acid (i.e., RNA or DNA) molecules.

B. Cholesterol-conjugated 2'-methoxyethoxy oligonucleotides

Cholesterol is conjugated to ISIS 13758 (2'-methoxyethoxy targeted to the translation start codon region), ISIS 13753 (2'-methoxyethoxy scrambled control for ISIS 13758), ISIS 13755 (2'-methoxyethoxy targeted to the translation termination codon region) and ISIS 14429 (2'-methoxyethoxy scrambled control for ISIS 13755) using 3'-O-[pentylamino-carbonyl-oxy-cholesteryl]-cytidine CPG as described above. Biological assays are conducted as described in Example 9. These phosphorothioate oligonucleotides are chimeric compounds having a 3'-cholesterol (for cellular uptake and nuclease resistance), 2'-methoxyethoxy modifications in their flanks (for better binding to the target nucleic acid and for nuclease resistance), and 2'-deoxy nucleotides in the center 10 nucleotide region (the "gap"). This configuration allows the chimeric oligonucleotide to have nuclease-resistant, high affinity "wings" while retaining an unmodified central "gap" that supports the action of RNase H when the oligonucleotide is bound to a target RNA molecule. Placing the cholesterol moiety at the 3'-terminus of the 3' oligonucleotide ensures resistance to 3' exonucleases, enhances cellular uptake, and leaves the 5'-terminus available for conjugation of additional functional groups.

Example 12

Plasma Uptake and Tissue Distribution of Active Oligonucleotides in Mice

The oligonucleotide Oligomer 71 (SEQ ID NO:20) from Example 7(C) was used as a first test oligonucleotide. This olignucleotides is identified in the figures as ISIS 8005. Further oligonucleotide of the same sequence were prepared in the same manner. These further oligonucleotides include a phosphorothioate oligonucleotide identified in the figures as ISIS 3082 and an oligonucleotide incorporating a $C_{18}$ alkyl group linked to the 5' position of the nucleotides via a 5' amino group (prepared utilizing the compound of Example 8(G) in the same manner as per the procedure of Example 7(C)) identified in the figures as ISIS 9047. The oligonucleotides were tritiated as per the procedure of Graham et al. (*Nuc. Acids Res.*, 1993, 16, 3737–3743).

A. Animals and Experimental Procedure

For each oligonucleotide studied, twenty male Balb/c mice (Charles River Laboratories, Inc., Wilmington, Mass.), weighing about 25 gm, were randomly assigned into one of four treatment groups. Following a one-week acclimation, mice received a single tail vein injection of $^3$H-radiolabeled oligonucleotide (approximately 750 nmoles/kg; ranging from 124–170 µCi/kg) administered in phosphate buffered saline, pH 7.0. The concentration of oligonucleotide in the dosing solution was approximately 60 µM. One retro-orbital bleed (at either 0.25, 0.5, 2, or 4 hours post-dose) and a terminal bleed (at either 1, 3, 8 or 24 hours post-dose) was collected from each group. The terminal bleed was collected by cardiac puncture following ketamine/xylazine anesthesia. An aliquot of each blood sample was reserved for radioactivity determination and the remaining blood was transferred to an EDTA-coated collection tube and centrifuged to obtain plasma. Urine and feces were collected at intervals (0–4, 4–8 and 8–24 hours) from the group terminated at 24 hours.

At termination, the liver, kidneys, spleen, lungs, heart, brain, sample of skeletal muscle, portion of the small intestine, sample of skin, pancreas, bone (both femurs containing marrow) and two lymph nodes were collected from each mouse and weighed. Feces were weighed, then homogenized 1:1 with distilled water using a Brinkmann Polytron homogenizer (Westbury, N.Y.). Plasma, tissues, urine and feces homogenate were divided for the analysis of radioactivity by combustion and for determination of intact oligonucleotide content. All samples were immediately frozen on dry ice after collection and stored at −80° C. until analysis.

B. Analysis of Radioactivity in Plasma, Tissue, and Excreta

Plasma and urine samples were weighed directly into scintillation vials and analyzed directly by liquid scintillation counting after the addition of 15 ml of BetaBlend (ICN Biomedicals, Costa Mesa, Calif.). All other samples (tissues, blood and homogenized feces) were weighed into combustion boats and oxidized in a Biological Materials Oxidizer (Model OX-100; R. J. Harvey Instrument Corp., Hillsdale, N.J.). The $^3$H$_2$O was collected in 20 ml of cocktail, composed of 15 ml of BetaBlend and 5 ml of Harvey Tritium Cocktail (R. J. Harvey Instrument Corp., Hillsdale, N.J.). The combustion efficiency was determined daily by combustion of samples spiked with a solution of $^3$H-mannitol and ranged between 73.9–88.3%. Liquid scintillation counting was performed using a Beckman LS 9800 or LS 6500 Liquid Scintillation System (Beckman Instruments, Fullerton, Calif.). Samples were counted for 10 minutes with automatic quench correction. Disintergration per minute values were corrected for the efficiency of the combustion process.

C. Analysis of Data

Radioactivity in samples was expressed as disintergrations per minute per gram of sample. These values were divided by the specific activity of the radiolabel to express the data in nanomole-equivalents of total oligonucleotide per gram of sample, then converted to percent of dose administered per organ or tissue. Assuming a tissue density of 1 gm/ml, the nmole/gram data were converted to a total µM concentration. To calculate the concentration of intact oligonucleotide in plasma, liver or kidney at each time point, the mean total µM concentrations were divided by the percent of intact oligonucleotide in the dosing solution (82–97%), then multiplied by the mean percentage of intact oligonucleotide at each time point as determined by CGE or HPLC. These data was then used for the calculation of tissue half-lives by linear regression and to compare the plasma pharmacokinetics of the different modified oligonucleotides. The pharmacokinetic parameters were determined using PCNONLIN 4.0 (Statistical Consultants, Inc., Apex, N.C.). After examination of the data, a one-compartment bolus input, first order output model (library model 1) was selected for use.

D. Plasma Uptake and Biodistribution Results

Figure 7:
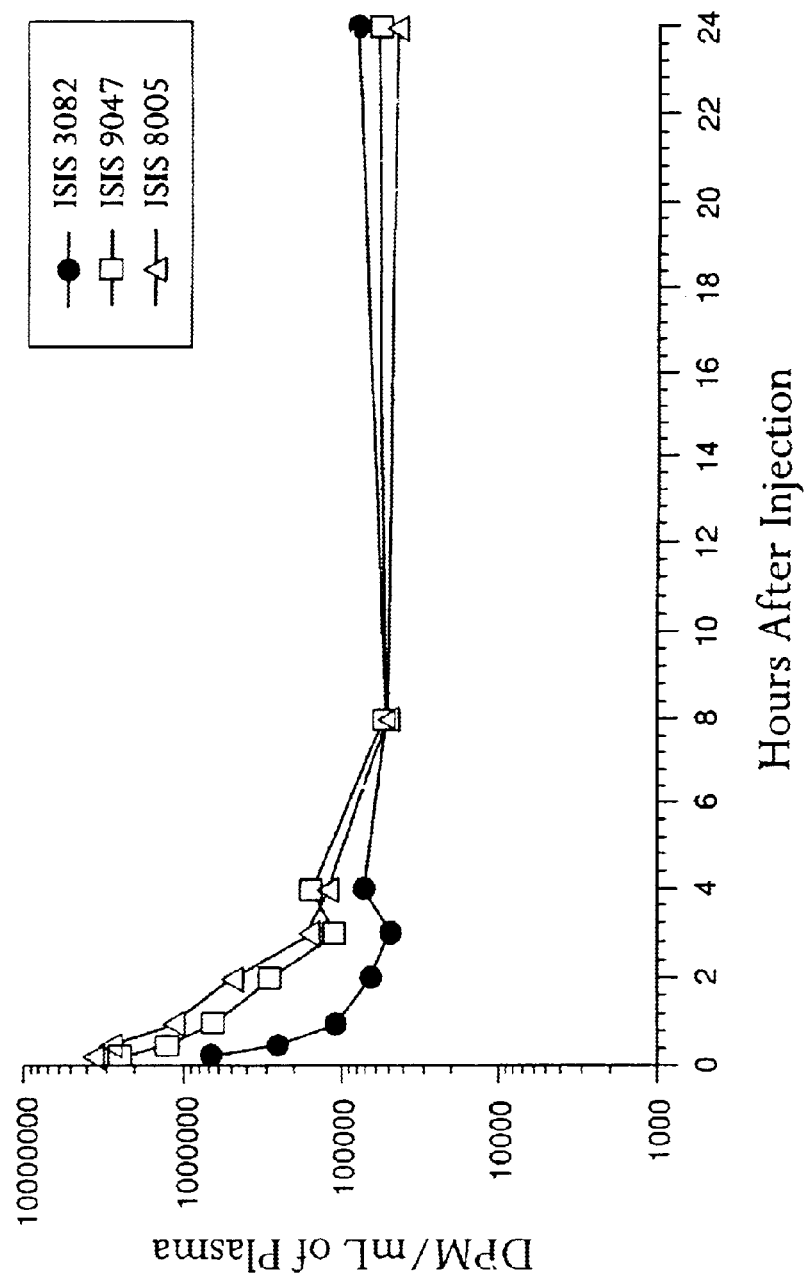
FIG. 7 is a graph showing mouse plasma concentrations of a control compound and two of the compounds of the invention. The plasma concentration is plotted versus time.
Figure 8:
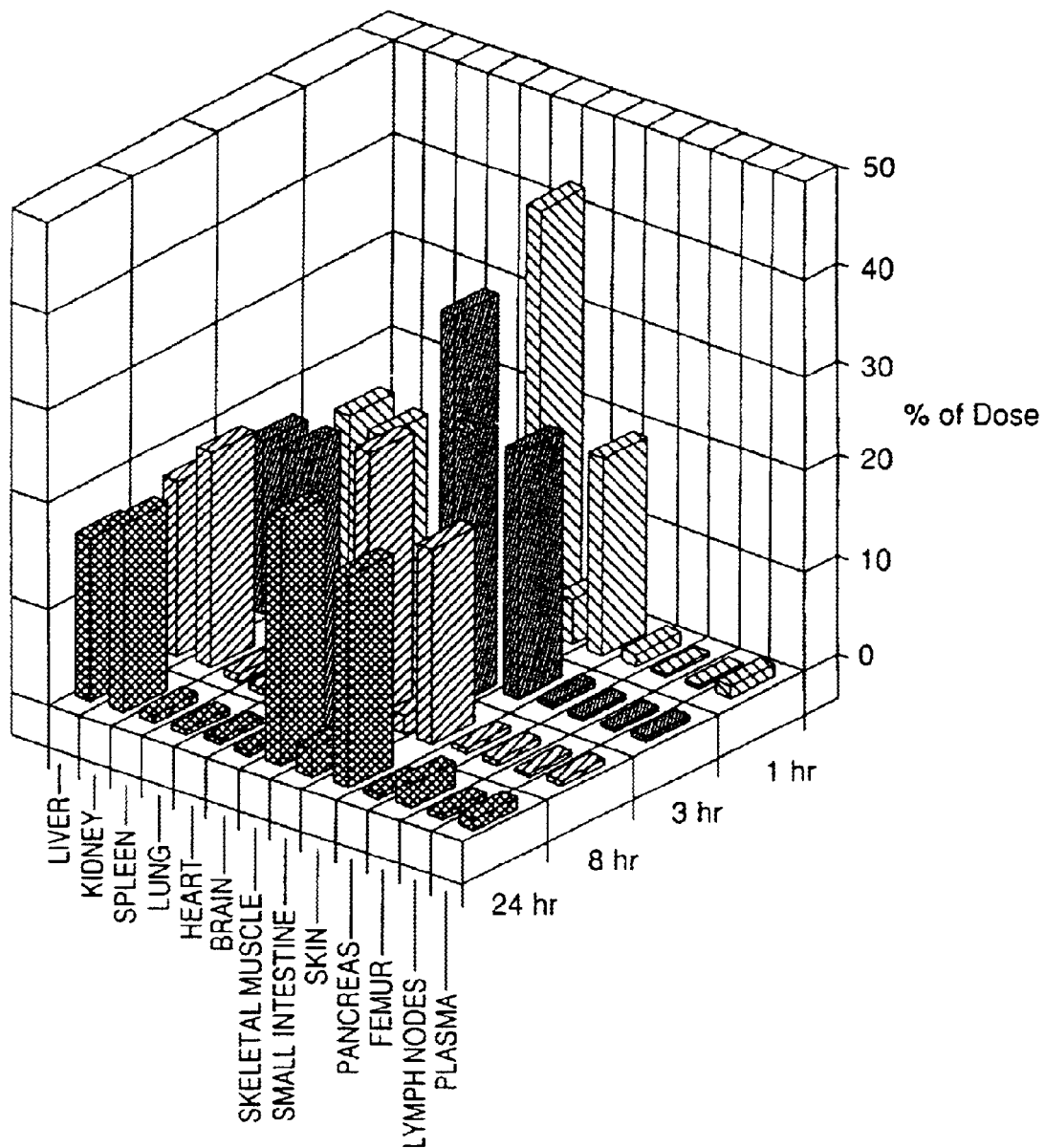
FIG. 8 is a three dimensional graph showing distribution of a control compound, ISIS 3082, among various tissues in the mouse. Specific tissues are shown on one axis, time on a second axis and percent of dose on the third axis. The compound was delivered by intravenous injection.
Figure 9:
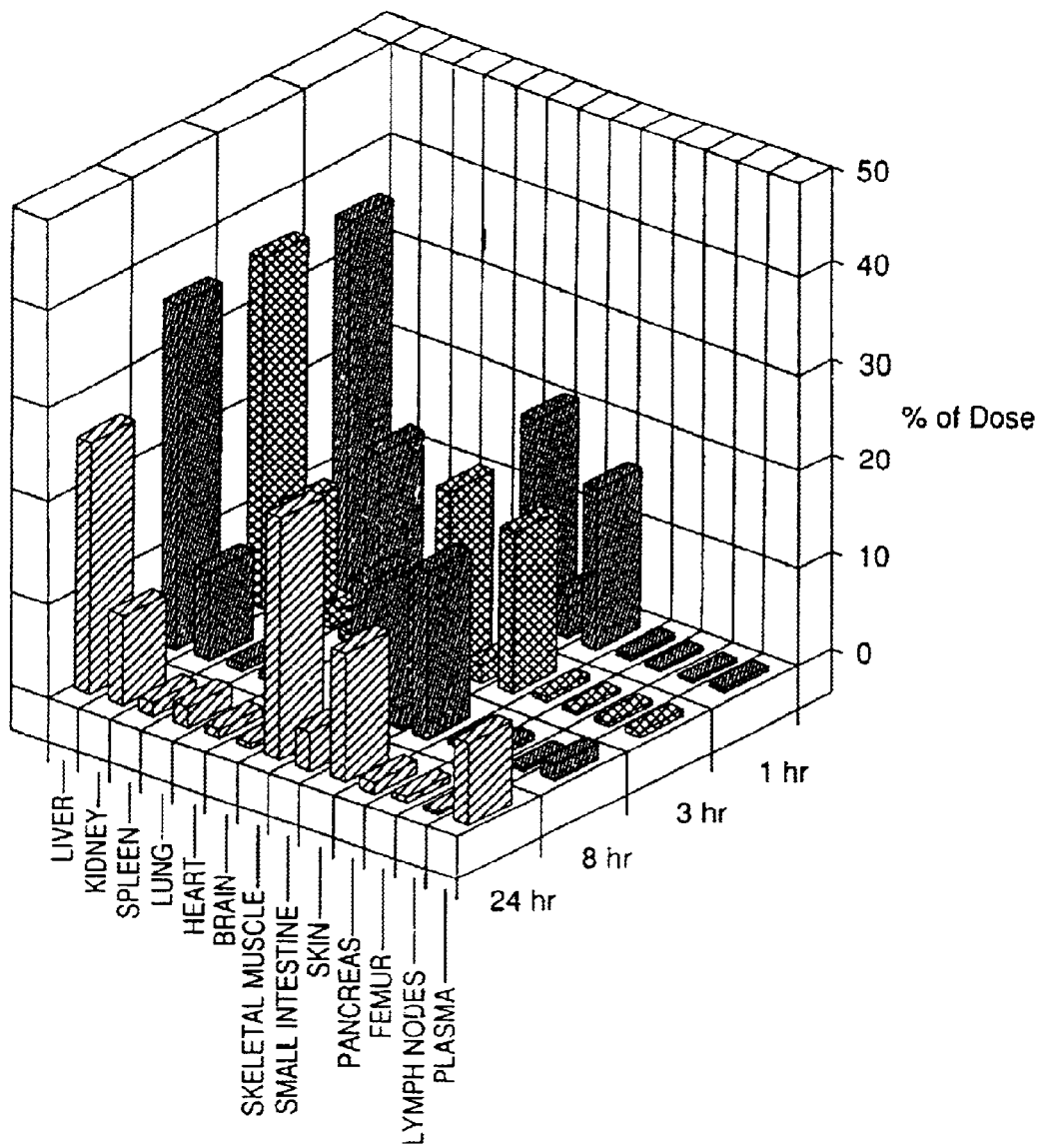
FIG. 9 is a three dimensional graph showing distribution of a compound of the invention, ISIS 9047, among various tissues in the mouse. Specific tissues are shown on one axis, time on a second axis and percent of dose on the third axis. The compound was delivered by intravenous injection.
Figure 10:
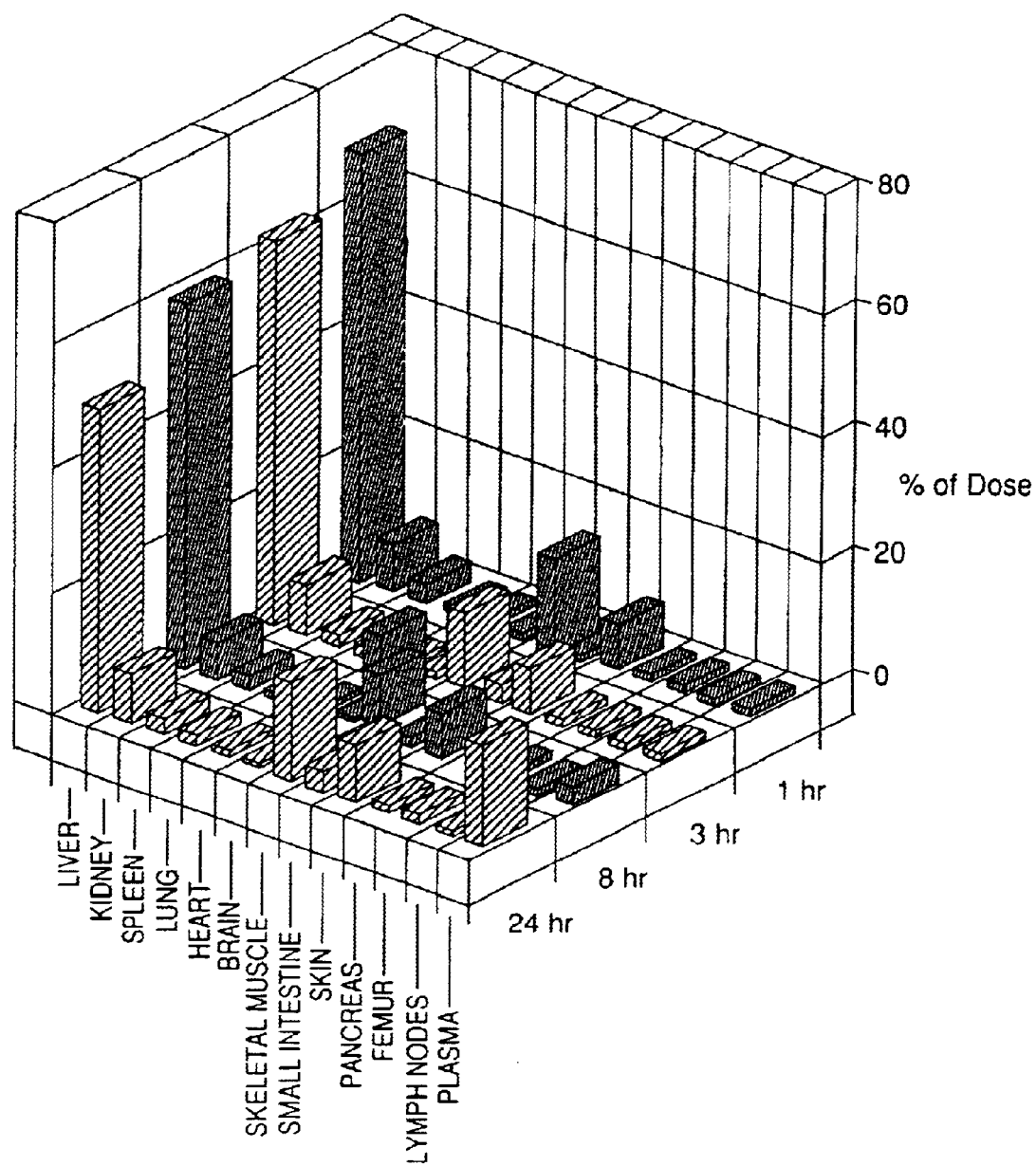
FIG. 10 is a three dimensional graph showing distribution of a further compound of the invention, ISIS 8005, among various tissues in the mouse. Specific tissues are shown on one axis, time on a second axis and percent of dose on the third axis. The compound was delivered by intravenous injection.

The result of the animal plasma uptake and tissue distribution tests are illustrated graphically in FIGS. 7 to 10. As is seen in FIG. 7, plasma concentration of each of the test oligonucleotides decrease from the initial injection levels to lower levels over the twenty-four hour test period. Plasma concentrations of the two oligonucleotides bearing conjugate groups of the invention were maintained at a higher level for a longer period than were those of the non-conjugate bearing phosphorothioate. All of the test compounds were taken up from the plasma to tissues as is shown in FIGS. 8, 9 and 10. The two compounds of the invention had different distribution between the various tissues. FIG. 8 shows the tissue distribution of the unconjugated phosphorothioate oligonucleotide, ISIS 3082. FIG. 9 shows the tissue distribution of oligonucleotide ISIS 9047 (identical to ISIS 3082 but having a $C_{18}$ amine moiety conjugated to the 5' terminal residue), while FIG. 10 shows the tissue distribution of oligonucleotide ISIS 8005 (also derived from ISIS 3082 and having a cholesteryl moiety conjugated to the 5' terminal residue). The distribution of 5'-$C_{18}$ amine antisense oligonucleotide (ISIS 9047) was similar to that of parent compiund ISIS 3082 except for an increase in distribution to the liver and a somewhat longer retention in plamsa. Both of these attributes were further enhanced in the case of the 5'-cholesteryl antisense oligonucleotide, with the amount of hepatic signal continuing to increase for at least 24 hours after dosing.

E. Modulation of ICAM-1 Expression in the Mammalian Liver by 5'-Cholesterol-Conjugated Antisense Oligonucleotides The results from the animal plasma uptake and tissue distribution studies indicate that ISIS 8005, a 5'-cholesterol-conjugated antisense oligonucleotide targeted to murine ICAM-1, preferentially accumulates in murine livers following i.v. administration. In order to determine if this preferential accumulation results in enhanced modulation of ICAM-1 in the mammalian liver, the following experiments were done.

Figure 11:
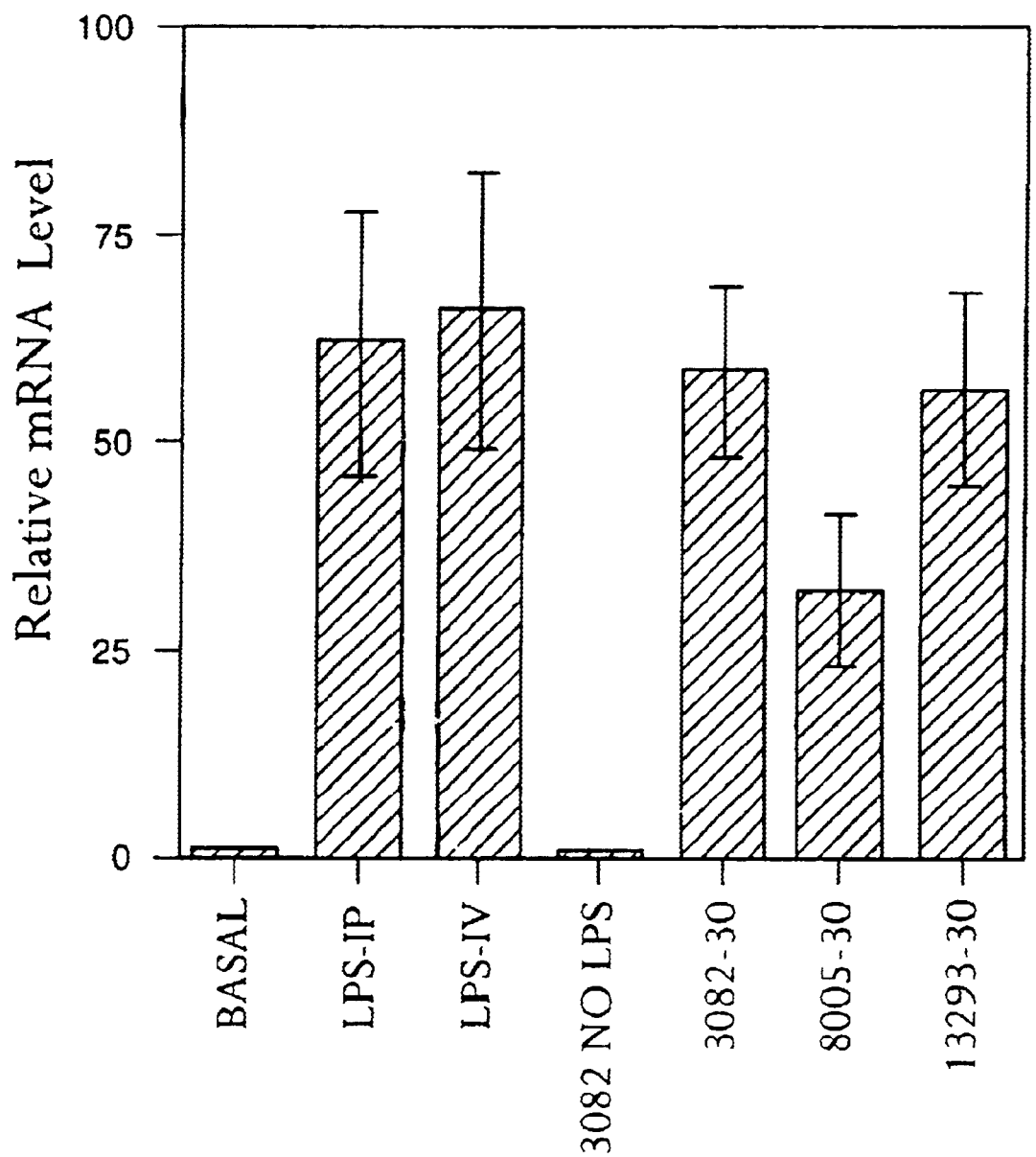
FIG. 11 shows data demonstrating the modulation of ICAM-1 mRNA levels in the livers of Balb/c mice by cholesterol-conjugated oligonucleotides. Terms: BASAL, untreated cells; LPS, lipopolysaccharide (ICAM-1 inducing agent); ISIS 3082, antisense phosphorothioate oligonucleotide targeted to mouse ICAM1 sequences; ISIS 8005, 5'-cholesterol conjugate of ISIS 3082; ISIS 13293, 5'-cholesterol-conjugated scrambled control oligonucleotide for ISIS 8005; the suffix "–30" indicates the dose (30 mg/kg) of oligonucleotide.

Mice were treated with oligonucleotides and examined as follows. First, 10 to 30 mg/kg of oligonucleotide (or a control solution) were administered (i.v.) to each mouse 24 and 2 hours prior to LPS treatment (FIG. 11 shows results with 30 mg/kg doses). Then, to induce ICAM-1 expression, bacterial lipopolysaccharide (LPS) was injected into the mice. After 2 hours, the mice were sacrificed, and particular organs, or specific portion thereof, were removed for further study. RNA was prepared from isolated, homogenized tissues essentially according to the guanidinium/CsCl purification method of Chirgwin et al. (*Biochemistry*, 979, 18, 5294), electrophoresed and transferred to nylon membranes for hybridization studies (Northern analysis) according to methods well known in the art. In order to detect mouse ICAM-1 mRNA, a radiolabelled probe was prepared by random oligonucleotide-primed synthesis using a mouse ICAM-1 clone as a template. The blots were stripped and reprobed with a $^{32}$P-labeled glyceraldehyde 3-phosphate dehydrogenase (G3PDH) probe (Clontech Laboratories, Inc., Palo Alto, Calif.) in order to confirm equal loading of RNA and to allow the levels of ICAM-1 transcripts to be normalized with regard to the G3PDH signals. Hybridizing bands were visualized by exposure to X-OMAT AR film and quantitated using a PHOSPHORIMAGER™ essentially according to the manufacturer's instructions (Molecular Dynamics, Sunnyvale, Calif.).

As shown in FIG. 11, LPS induced ICAM-1 mRNA levels in the murine liver by at least one order of magnitude relative to untreated animals ("BASAL") whether administered i.v. ("LPS-IV") or i.p. ("LPS-IP"). At the given dosages, in the absence of an uptake facilitator, ISIS 3082 ("3082-30," indicating 30 mg/kg of ISIS 3082) was unable to reverse the LPS-mediated induction of ICAM-1 mRNA in the liver. In contrast, under these conditions, ISIS 8005 ("8005-30"), a 5'-conjugated cholesterol derivative of ISIS 3082, reduced the amount of hepatic ICAM-1 mRNA by about 50% relative to the amount present in the livers of animals to which LPS, but not oligonucleotide, was administered. A control 5'-cholesterol conjugated scrambled oligonucleotide, ISIS 13293, had no apparent effect on induced ICAM-1 levels.

Figure 12:
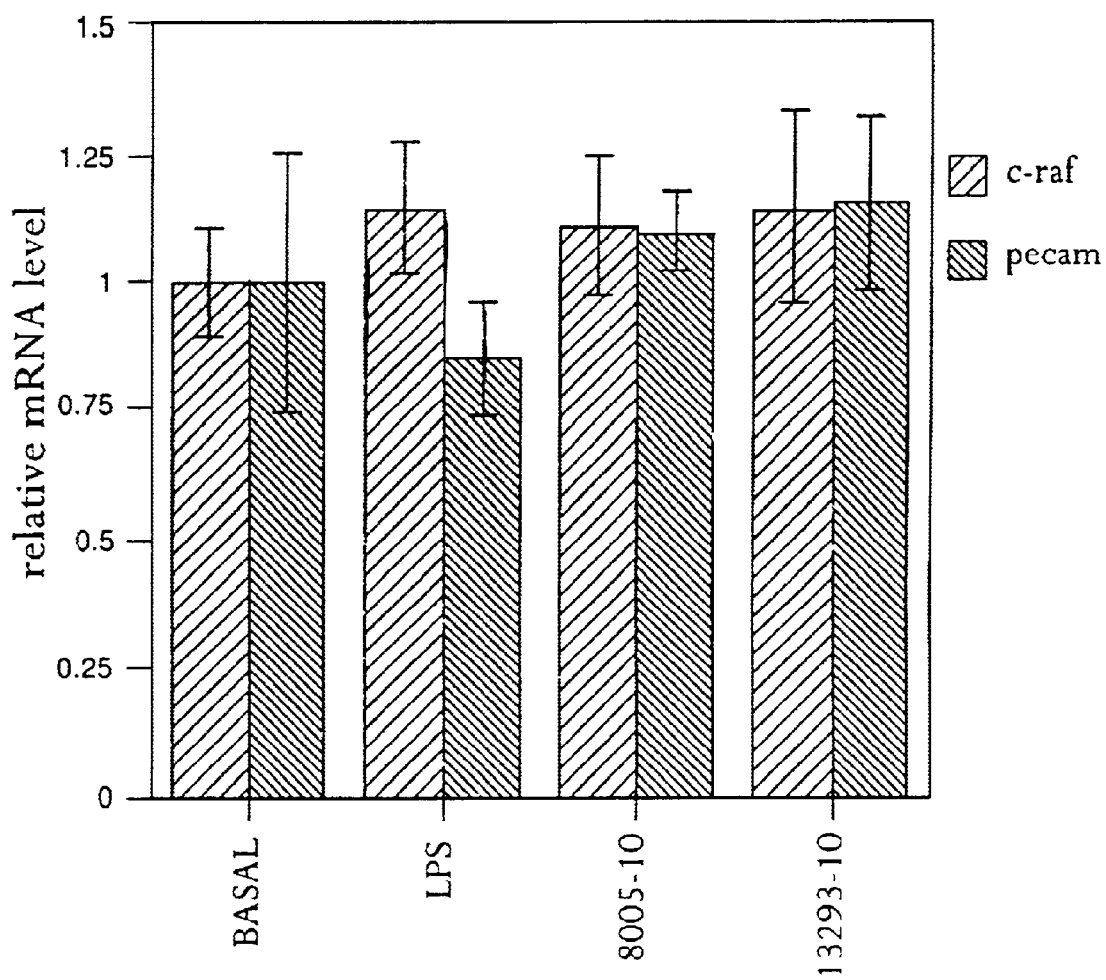
FIG. 12 shows that the 5'-cholesterol ISIS 3082 analog (ISIS 8005) has no effect on c-raf and PECAM-1 mRNA levels in the murine liver. Terms: basal, untreated cells; lps, lipopolysaccharide (ICAM-1 inducing agent); ISIS 8005, 5'-cholesterol conjugated phosphorothioate antisense oligonucleotide targeted to mouse ICAM-1; ISIS 13293, 5'-cholesterol-conjugated scrambled control oligonucleotide for ISIS 8005; the suffix "–10" indicates the dose (10 mg/kg) of oligonucleotide.

In similar experiments, the sequence (gene target) specificity of the 4'-cholesterol antisense oligonucleotide ISIS 8005 was examined. ISIS 8005, which is targeted to ICAM-1, had no effect on the levels of mRNA derived from the oncogene c-raf or encoding the cellular adhesion molecule PECAM-1 which is related to, yet distinct from, ICAM-1. As shown in FIG. 12, the 5'-cholesterol 3082 analog had no discernable effect on c-raf or PECAM-1 mRNA levels.

Figure 13:
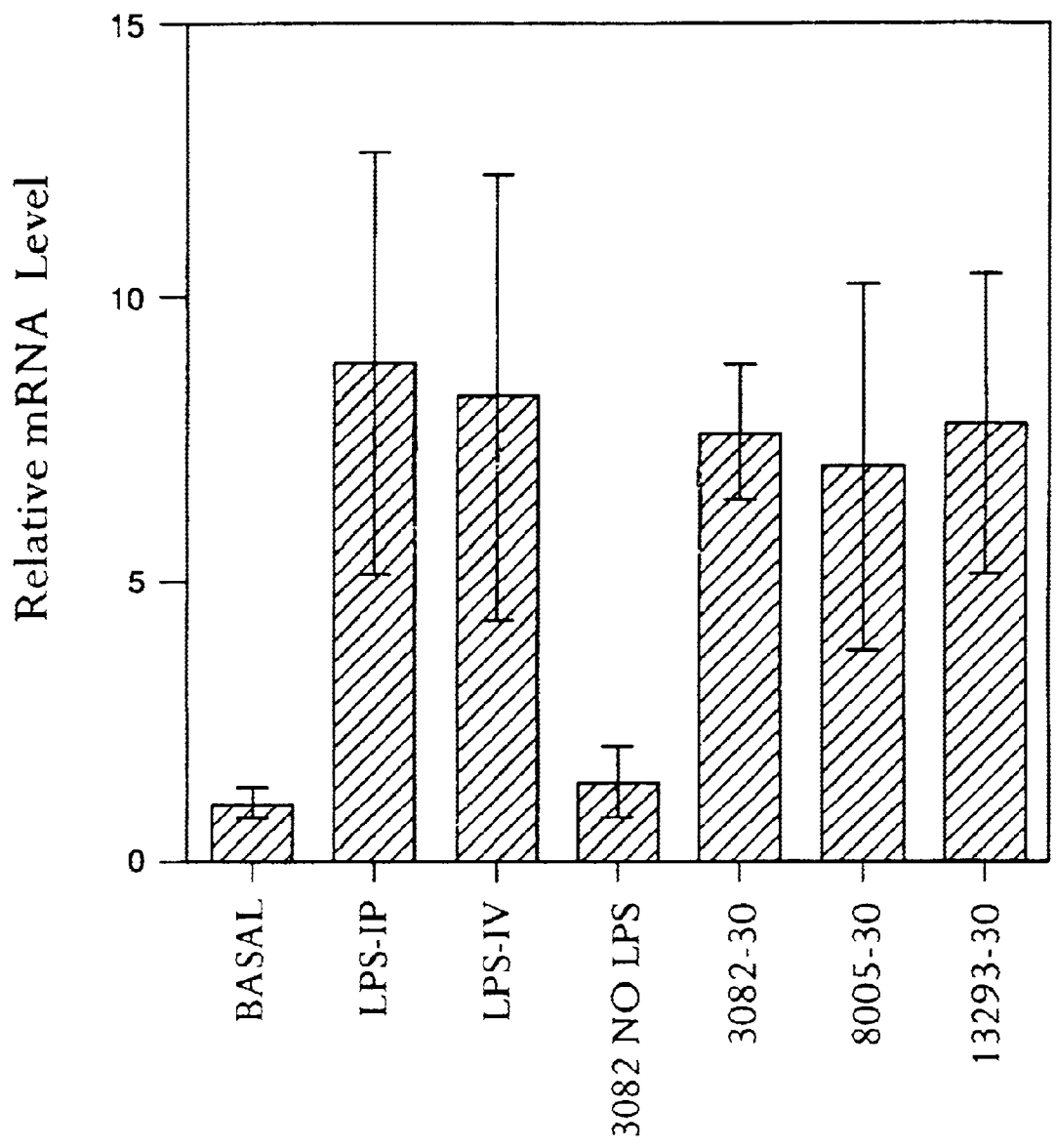
FIG. 13 shows that the 5'-cholesterol ISIS 3082 analog (ISIS 8005) has little effect on ICAM-1 levels in murine lungs. Terms: BASAL, untreated cells; LPS, lipopolysaccharide (ICAM-1 inducing agent); ISIS 3082, antisense phosphorothioate oligonucleotide targeted to mouse ICAM1 sequences; ISIS 8005, 5'-cholesterol conjugate of ISIS 3082; ISIS 13293, 5'-cholesterol-conjugated scrambled control oligonucleotide for ISIS 8005; the suffix "–30" indicates the dose (30 mg/kg) of oligonucleotide.

To determine if the antisense-mediated inhibition of ICAM-1 mRNA in the mammalian liver is organ-specific, levels of ICAM-1 mRNA in lung samples from the sacrificed animals used in the experiments described above were examined by Northern assays. As is shown in FIG. 13, administration of LPS induced ICAM-1 mRNA levels in the lung, albeit to a lesser degree than seen in liver samples. In any event, neither ISIS 3082 nor its 5'-cholesterol conjugate ISIS 8005 was able to reverse the LPS-mediated induction of ICAM-1 to any great degree under these conditions.

Figure 14:
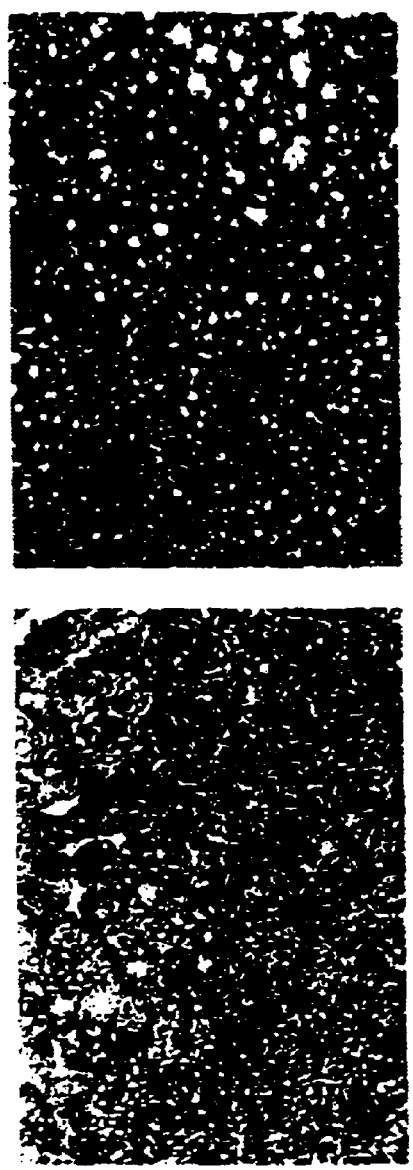
FIG. 14 shows the histology of reversal of LPS-mediated ICAM-1 induction by cholesterol-conjugated antisense oligonucleotides.
Figure 14:
Figure 14:

Immunohistological sections of isolated liver samples were prepared and stained using primary antibodies specific for ICAM-1 and secondary antibodies conjugated to horse radish peroxidase (HRP). As shown in FIG. 14, the cross-section from untreated livers ("Basal") is virtually indistinguishable from livers treated with the ICAM-1 inducer LPS and the 5'-cholesterol conjugated ICAM-1-targeted antisense oligonucleotide ISIS 8005 (two left panels). In contrast, livers induced by LPS and treated with ISIS 13293, a 5'-cholesterol conjugated scrambled control (5'-GCG-TTG-CTC-TTC-TTC-TTG-CG, SEQ ID NO:64) phosphorothioate oligonucleotide for ISIS 8005 appear quite dark (two panels on right) due to the signal resulting from HRP bound (via a series of antibodies) to ICAM-1. These results indicate that levels of the ICAM-1 protein in the mammalian liver can, like the levels of ICAM-1 mRNA in livers, be modulated by a cholesterol-conjugated antisense oligonucleotide in a sequence-specific manner. Moreover, comparison of the overall cellular structure in the untreated ("basal") livers to LPS- and ISIS 8005-treated reveals that there are no gross cellular defects resulting from antisense-mediated reversal of ICAM-1 induction.

Figure 15:
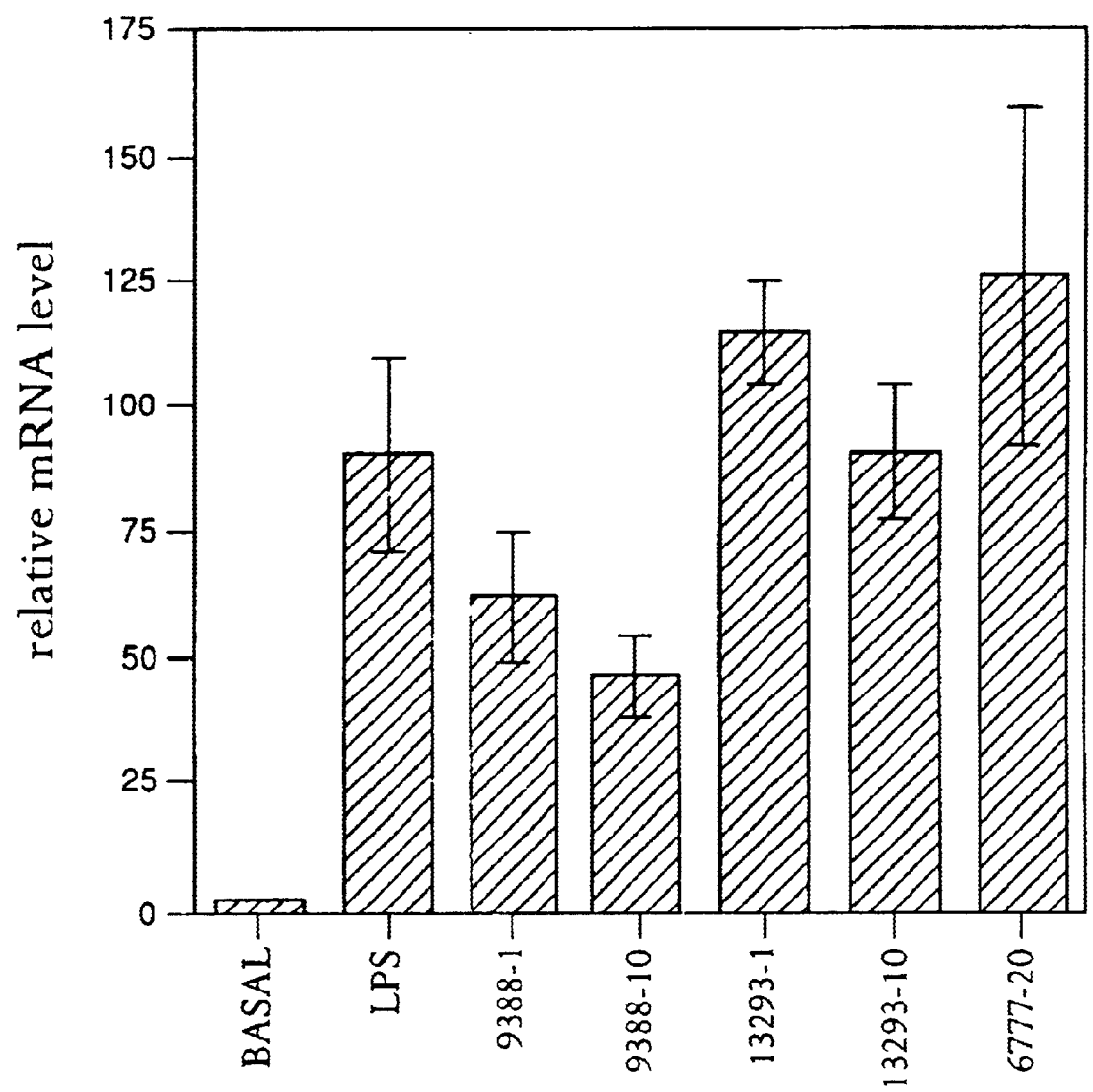
FIG. 15 shows that Balb/c mouse liver ICAM-1 mRNA levels can be modulated by a 3'-cholesterol-conjugated antisense oligonucleotide. Terms: basal, untreated cells; lps, lipopolysaccharide (ICAM-1 inducing agent); ISIS 9388, 3'-cholesterol conjugated phosphorothioate antisense oligonucleotide targeted to mouse ICAM-1; ISIS 13293, 5'-cholesterol-conjugated scrambled control oligonucleotide for ISIS 8005; ISIS 6777, control oligonucleotide targeted to VCAM-1; the suffixes "–1", "–10" and "–20" indicate the dose (1, 10 or 10 mg/kg, respectively) of oligonucleotide.

For comparison's sake, ISIS 9388, a 3'-cholesterol-conjugated derivative of ISIS 3082 (SEQ ID NO:20), was also prepared. Specifically, ISIS 9388 contains a 3' terminal 3'-O-hexylamino cholesteryl moiety introduced into the oligonucelotide during synthesis using the phosphoramidite from Example 4(B) and other methods disclosed herein. ISIS 9388, and some associated control compounds, were tested for their ability to modulate ICAM-1 mRNA levels in murine livers according to the preceding methods. The results, shown in FIG. 15, demonstrate that, like the 5'-cholesterol conjugate (ISIS 8005), the 3'-cholesterol conjugate (ISIS 9388) is able to reduce ICAM-1 mRNA levels by about 50% under these conditions (i.e., a dosage of 10 mg/kg of oligonucleotide).

The results in this Example demonstrate that cholesterol-conjugated antisense oligonucleotides are preferentially taken up by cultured mammalian cells in vitro and targeted to the mammalian liver in vivo. Furthermore, the oligonucleotides that are targeted to the liver in vivo effect sequence-specific antisense modulation of their target gene in the liver in vivo, irregardless of the point of attachment of the cholesteryl moiety. Taken together, these findings provide the basis for a method of preferentially targeting a biologically active antisense oligonucleotide to hepatic tissues in mammals, and thereby modulating the expression of a gene in the liver of a mammal, by conjugating the oligonucleotide to a cholesteryl moiety and administering the cholesterol-oligonucleotide conjugate to a mammal.

What is claimed is:

1. A method of preferentially targeting a biologically active antisense oligonucleotide to hepatic tissues in a mammal to modulate the expression of a gene in the liver of a mammal, comprising the step of conjugating the oligonucleotide to a cholesteryl moiety and administering the cholesterol-oligonucleotide conjugate to said mammal to achieve said preferential targeting.

2. A method of modulating the expression of a nucleic acid in the hepatic system of a mammal, comprising the step of administering to said mammal a compound to modulate the expression of said nucleic acid, said compound comprising a plurality of linked nucleosides, wherein:

each nucleoside includes a ribofuranosyl sugar portion and a base portion; and
   at least one of said nucleosides bears at a 2'-O-position, a 3'-O-position, or a 5'-O-position a substituent having formula:

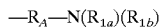

where:

$R_A$ is alkyl having from 1 to about 10 carbon atoms or $(CH_2-CH_2-Q)_x$;

$R_{1a}$ and $R_{1b}$, independently, are H, $R_2$, an amine protecting group or have formula $C(X)-R_2$, $C(X)-R_A-R_2$, $C(X)-Q-R_A-R_2$, $C(X)-Q-R_2$; and $R_2$ is cholesterol;

X is O or S;

each Q is, independently, NH, O, or S;

x is 1 to about 200;

$R_3$ is H, $R_A$, C(O)OH, C(O)OR$_A$, C(O)R$_4$, $R_A-N_3$, or $R_A-NH_2$;

$R_4$ is Cl, Br, I, $SO_2R_5$ or has structure;

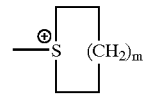

m is 2 to 7; and $R_5$ alkyl having 1 to about 10 carbon atoms;

wherein at least one of $R_{1a}$ and $R_{1b}$ are $R_2$.

3. A method of preferentially targeting an oligonucleotide to hepatic tissues in a mammal comprising administering to said mammal an oligonucleotide having a cholesteryl moiety conjugated thereto, to preferentially target said oligonucleotide to hepatic tissues in said mammal.

4. The method of claim 3 wherein said cholesteryl moiety is conjugated to said oligonucleotide through an alkylamine tether.

5. The method of claim 3 wherein said cholesteryl moiety is conjugated to said oligonucleotide at the terminal 5'-hydroxyl group of said oligonucleotide.

6. The method of claim 3 wherein said cholesteryl moiety is conjugated to said oligonucleotide at the terminal 3'-hydroxyl group of said oligonucleotide.

7. The method of claim 3 wherein said cholesteryl moiety is conjugated to said oligonucleotide at a 2'-hydroxyl group of said oligonucleotide.

\* \* \* \* \*

UNITED STATES PATENT AND TRADEMARK OFFICE
CERTIFICATE OF CORRECTION

| | | |
|---|---|---|
| PATENT NO. | : 6,753,423 B1 | Page 1 of 1 |
| APPLICATION NO. | : 09/546596 | |
| DATED | : June 22, 2004 | |
| INVENTOR(S) | : Phillip Dan Cook et al. | |

It is certified that error appears in the above-identified patent and that said Letters Patent is hereby corrected as shown below:

1) Title Page:
Item [63], Related U.S. Application data, please delete "Continuation of application No. 08/928,823, filed on Sep. 12, 1997, and a continuation-in-part of application No. 08/731,299, filed on Oct. 4, 1996, now Pat. No. 6,078,785, which is a continuation-in-part of application No. 08/464,953, filed on Jun. 5, 1995, and a continuation-in-part of application No. 08/344,155, filed on Nov. 23, 1994, now Pat. No. 5,883,082, which is a continuation-in-part of application No. 08/117,363, filed on Sep. 3, 1993, which is a continuation-in-part of application no. 08/063,167, filed on May 17, 1993, now Pat. No. 5,514,788, which is a continuation-in-part of application No. 08/007,997, filed on Jan. 21, 1993, now Pat. No. 5,591,623, which is a continuation-in-part of application No. PCT/US92/09196, filed on Oct. 23, 1992, which is a continuation-in-part of application No. 07/782,374, filed on Oct. 24, 1991, now abandoned, which is a continuation-in-part of application No. 07/567,286, filed on Aug. 14, 1990, now abandoned, and a continuation-in-part of application No. 07/566,977, filed on Aug. 13, 1990, now abandoned, which is a continuation-in-part of application No. 07/463,358, filed on Jan. 11, 1990, now abandoned" and insert therefor -- Continuation of application No. 08/928,823, filed on Sep. 12, 1997, which is a continuation-in-part of application No. 08/731,199, filed on Oct. 4, 1996; and a continuation-in-part of application No. 08/344,155, filed on Nov. 23, 1994, now Pat. No. 5,883,082; and a continuation-in-part of application No. 08/464,953, filed on Jun. 5, 1995, now Pat. No. 6,900,297, which is a continuation-in-part of application No. 08/117,363, filed on Sep. 3, 1993, now Pat. No. 6,783,931, which is a continuation-in-part of application No. 07/782,374, filed on Oct. 24, 1991, now abandoned, which is a continuation-in-part of application No. PCT/US91/00243, filed on Jan. 11, 1991, which is a continuation-in-part of application No. 07/463,358, filed on Jan. 11, 1990, now abandoned, and is a continuation-in-part of application No. 07/566,977, filed on Aug. 13, 1990, now abandoned --.

Signed and Sealed this

Twenty-second Day of August, 2006

JON W. DUDAS
*Director of the United States Patent and Trademark Office*

SEQUENCE LISTING (1) GENERAL INFORMATION:

(iii) NUMBER OF SEQUENCES: 63

(2) INFORMATION FOR SEQ ID NO: 1:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

GGCTGACTGC G                                                  11

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

CTGTCTCCAT CCTCTTCACT                                     20

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

TTGCTTCCAT CTTCCTCGTC                                     20

(2) INFORMATION FOR SEQ ID NO: 4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

TGGGAGCCAT AGCGAGGC                                         18

(2) INFORMATION FOR SEQ ID NO: 5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

UGGGAGCCAU AGCGAGGC                                         18

(2) INFORMATION FOR SEQ ID NO: 6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

TCCAGGTGTC CGCATC                                           16

(2) INFORMATION FOR SEQ ID NO: 7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

GGACCGGAAG GTACGAG                                          17

(2) INFORMATION FOR SEQ ID NO: 8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

CCTGGCCTTC CATGCTC                                          17

(2) INFORMATION FOR SEQ ID NO: 9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO: 9:

CCUGGCCUUC CAUGCUC                                          17

(2) INFORMATION FOR SEQ ID NO: 10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

CCCAGGCTCA GA                                               12

(2) INFORMATION FOR SEQ ID NO: 11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

GAGCUCCCAG GC                                                     12

(2) INFORMATION FOR SEQ ID NO: 12:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

CAUGCUGCAG CC                                                     12

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

GCCTTTCGCG ACCCAACACU                                             20

(2) INFORMATION FOR SEQ ID NO: 14:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

GCGTGUCTGC G                                                      11

(2) INFORMATION FOR SEQ ID NO: 15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

UGGGAGCCAT AGCGAGGC                                               18

(2) INFORMATION FOR SEQ ID NO: 16:

(i) SEQUENCE CHARACTERISTICS:
        (A) LENGTH: 18 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

TGGGAGCCAU AGCGAGGC                                                 18

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

UCTGAGTAGC AGAGGAGCTC                                               20

(2) INFORMATION FOR SEQ ID NO: 18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

UGCCCAAGCT GGCATCCGTC A                                             21

(2) INFORMATION FOR SEQ ID NO: 19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

UGCGTTTGCT CTTCTTCTTG CG                                            22

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

UGCATCCCCC AGGCCACCAT                                               20

(2) INFORMATION FOR SEQ ID NO: 21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO: 21:

UCCCGCCTGT GACATGCATT                                               20

(2) INFORMATION FOR SEQ ID NO: 22:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 22:

GUTCTCGCTG GTGAGTTTCA                                               20

(2) INFORMATION FOR SEQ ID NO: 23:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 23:

UUGGGAGCCA TAGCGAGGC                                                19

(2) INFORMATION FOR SEQ ID NO: 24:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 24:

CCAAGCCUCA GA                                                       12

(2) INFORMATION FOR SEQ ID NO: 25:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 25:

CCAGGCUCAG AT                                                       12

(2) INFORMATION FOR SEQ ID NO: 26:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 26:

```
UGCCCAAGCT GGCATCCGTC A                                              21

(2) INFORMATION FOR SEQ ID NO: 27:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 27:

GAGCCGCTAC TCGAATGAGC                                                20

(2) INFORMATION FOR SEQ ID NO: 28:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 28:

GTTCTGGCTT CCGTTGCACC                                                20

(2) INFORMATION FOR SEQ ID NO: 29:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 29:

CCCGGCCCGG ATTGACTGAA                                                20

(2) INFORMATION FOR SEQ ID NO: 30:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 30:

CCATCCCGAC CTCGCGCTCC                                                20

(2) INFORMATION FOR SEQ ID NO: 31:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 31:

CGGTCCCCTT CAAGATCCAT                                                20

(2) INFORMATION FOR SEQ ID NO: 32:
```

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 32:

CCCCTTCAAG ATCCATCCCG                                                   20

(2) INFORMATION FOR SEQ ID NO: 33:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 33:

CAAGATCCAT CCCGACCTCG                                                   20

(2) INFORMATION FOR SEQ ID NO: 34:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 34:

CCTGGTCATG TCTTCCTCCA                                                   20

(2) INFORMATION FOR SEQ ID NO: 35:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 35:

CTTTGCCCAG ACAGCAGCTG                                                   20

(2) INFORMATION FOR SEQ ID NO: 36:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 36:

GTTCACTGGC GCTTTGTTCC                                                   20

(2) INFORMATION FOR SEQ ID NO: 37:

(i) SEQUENCE CHARACTERISTICS:
        (A) LENGTH: 20
        (B) TYPE: Nucleic Acid

```
        (C) STRANDEDNESS: Single
        (D) TOPOLOGY: Linear (iv) ANTI-SENSE: Yes (xi) SEQUENCE DESCRIPTION: SEQ ID NO: 37:

TGAACTTGAC TGAGGAAATG                                              20

(2) INFORMATION FOR SEQ ID NO: 38:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 38:

CTTGGAAGAG CCGCTACTCG                                              20

(2) INFORMATION FOR SEQ ID NO: 39:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 39:

GCCGCTACTC GAATGAGCGC                                              20

(2) INFORMATION FOR SEQ ID NO: 40:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 40:

GGAAGAGCCG CTACTCGAAT                                              20

(2) INFORMATION FOR SEQ ID NO: 41:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 41:

CTCTGTTCCT TTAATTACGA                                              20

(2) INFORMATION FOR SEQ ID NO: 42:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes
```

(xi) SEQUENCE DESCRIPTION: SEQ ID NO: 42:

TCCACTTGAT GATGTCTCTC                                                       20

(2) INFORMATION FOR SEQ ID NO: 43:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 43:

CTATGATTTC TCTCCACTTG                                                       20

(2) INFORMATION FOR SEQ ID NO: 44:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 44:

GGCAGTCAGT TACAGTCCAA                                                       20

(2) INFORMATION FOR SEQ ID NO: 45:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 45:

TTTTAGCAAG GCAGTCAGTT                                                       20

(2) INFORMATION FOR SEQ ID NO: 46:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 46:

TGCAAACATT TCAATACTTT                                                       20

(2) INFORMATION FOR SEQ ID NO: 47:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 47:

AAGTTTAGTT TTATTATAGA                                                       20

(2) INFORMATION FOR SEQ ID NO: 48:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 48:

CACCACCCCC CTCGCTGGTC                                                 20

(2) INFORMATION FOR SEQ ID NO: 49:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 49:

CTCCCGCACA TCTCCGCGCC                                                 20

(2) INFORMATION FOR SEQ ID NO: 50:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 50:

GCCACCGTCT GCCCACTCTG                                                 20

(2) INFORMATION FOR SEQ ID NO: 51:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 51:

GGCACGTGCA ATGGCGATCC                                                 20

(2) INFORMATION FOR SEQ ID NO: 52:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 52:

CGGAGCCGCT TGGTGAGGAT                                                 20

(2) INFORMATION FOR SEQ ID NO: 53:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 53:

AGCAGCATCA TTGGCGAGCC                                                   20

(2) INFORMATION FOR SEQ ID NO: 54:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 54:

CGGCCATGGC ACCAAAGACA                                                   20

(2) INFORMATION FOR SEQ ID NO: 55:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 55:

TGAACTGACT TGCCCCACGG                                                   20

(2) INFORMATION FOR SEQ ID NO: 56:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 56:

GGGATGTCCG GTCGGGTGGG                                                   20

(2) INFORMATION FOR SEQ ID NO: 57:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 57:

TGCCCACCAG AGCCAGCGTC                                                   20

(2) INFORMATION FOR SEQ ID NO: 58:

(i) SEQUENCE CHARACTERISTICS:
        (A) LENGTH: 20
        (B) TYPE: Nucleic Acid
        (C) STRANDEDNESS: Single -continued (D) TOPOLOGY: Linear (iv) ANTI-SENSE: Yes (xi) SEQUENCE DESCRIPTION: SEQ ID NO: 58:

ATGCCCAGGT GTGCTCGGAG                                           20

(2) INFORMATION FOR SEQ ID NO: 59:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 59:

GCCTCCTTTG CTGCCCTCAC                                           20

(2) INFORMATION FOR SEQ ID NO: 60:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 60:

TGGTGGACAG GCGGTGAGCA                                           20

(2) INFORMATION FOR SEQ ID NO: 61:

(i) SEQUENCE CHARACTERISTICS:
        (A) LENGTH: 30
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 61:

GGATCTTGAA GGGGACCGCA ATGGAGGAGC                                30

(2) INFORMATION FOR SEQ ID NO: 62:

(i) SEQUENCE CHARACTERISTICS:
        (A) LENGTH: 30
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 62:

GTCCAACACT AAAAGCCCCA ATTAATACAG                                30

(2) INFORMATION FOR SEQ ID NO: 63:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes

```
            (xi) SEQUENCE DESCRIPTION: SEQ ID NO: 63:

CTTACCCGCT TGTGTTGCTG                                                          20
```